US009617584B2

(12) United States Patent
Rabbani et al.

(10) Patent No.: US 9,617,584 B2
(45) Date of Patent: Apr. 11, 2017

(54) PROCESSES FOR DETECTING OR QUANTIFYING NUCLEIC ACIDS USING AN ARRAY OF FIXED OR IMMOBILIZED NUCLEIC ACIDS

(71) Applicant: Enzo Biochem, Inc., New York, NY (US)

(72) Inventors: Elazar Rabbani, New York, NY (US); Jannis G. Stavrianopoulos, Bay Shore, NY (US); James J. Donegan, Long Beach, NY (US); Jack Coleman, East Northport, NY (US)

(73) Assignee: Enzo Biochem, Inc., New York, NY (US)

( * ) Notice: Subject to any disclaimer, the term of this patent is extended or adjusted under 35 U.S.C. 154(b) by 42 days.

(21) Appl. No.: 14/812,293

(22) Filed: Jul. 29, 2015

(65) Prior Publication Data

US 2015/0368699 A1    Dec. 24, 2015

Related U.S. Application Data

(62) Division of application No. 10/902,641, filed on Jul. 29, 2004, now Pat. No. 9,234,235, which is a division of application No. 09/896,897, filed on Jun. 30, 2001, now abandoned.

(51) Int. Cl.
| | |
|---|---|
| C12P 19/34 | (2006.01) |
| C12Q 1/68 | (2006.01) |
| C07H 21/00 | (2006.01) |
| C12N 15/10 | (2006.01) |
| B01J 19/00 | (2006.01) |
| C40B 40/00 | (2006.01) |

(52) U.S. Cl.
CPC ........ *C12Q 1/6837* (2013.01); *B01J 19/0046* (2013.01); *C07H 21/00* (2013.01); *C12N 15/1058* (2013.01); *C12Q 1/6809* (2013.01); *C12Q 1/6825* (2013.01); *B01J 2219/00599* (2013.01); *B01J 2219/00648* (2013.01); *B01J 2219/00722* (2013.01); *C07B 2200/11* (2013.01); *C40B 40/00* (2013.01)

(58) Field of Classification Search
USPC ...................................... 435/6.12, 91.1, 91.2
See application file for complete search history.

(56) References Cited

U.S. PATENT DOCUMENTS

| | | |
|---|---|---|
| 4,563,417 A | 1/1986 | Albarella et al. |
| 4,724,202 A | 2/1988 | Dattagupta et al. |
| 4,732,847 A | 3/1988 | Stuart |
| 4,868,104 A | 9/1989 | Kurn et al. |
| 4,994,373 A | 2/1991 | Stavrianopoulos |
| 5,143,854 A | 9/1992 | Pirrung |
| 5,227,292 A | 7/1993 | White et al. |
| 5,241,060 A | 8/1993 | Engelhardt |
| 5,270,184 A | 12/1993 | Walker |
| 5,399,491 A | 3/1995 | Kacian |
| 5,409,818 A | 4/1995 | Davey |
| 5,432,065 A | 7/1995 | Fuller |
| 5,491,063 A | 2/1996 | Fisher |
| 5,523,217 A | 6/1996 | Lupski |
| 5,545,540 A | 8/1996 | Mian |
| 5,605,662 A | 2/1997 | Heller |
| 5,616,478 A | 4/1997 | Chetverin et al. |
| 5,641,658 A | 6/1997 | Adams et al. |
| 5,695,926 A | 12/1997 | Cros et al. |
| 5,716,785 A | 2/1998 | Van Gelder |
| 5,744,311 A | 4/1998 | Fraiser et al. |
| 5,824,517 A | 10/1998 | Cleuziat |
| 5,849,546 A | 12/1998 | Sousa |
| 5,853,993 A | 12/1998 | Dellinger et al. |
| 5,856,092 A | 1/1999 | Dale et al. |
| 5,891,636 A | 4/1999 | Van Gelder |
| 5,919,523 A | 7/1999 | Sundberg |
| 5,932,451 A | 8/1999 | Wang et al. |
| 5,972,607 A | 10/1999 | Kondo |
| 5,985,549 A | 11/1999 | Singer et al. |
| 5,994,056 A | 11/1999 | Higuchi |
| 6,017,738 A | 1/2000 | Morris |
| 6,040,138 A | 3/2000 | Lockhart |
| 6,103,474 A | 8/2000 | Dellinger et al. |
| 6,114,152 A | 9/2000 | Serafini et al. |
| 6,197,554 B1 | 3/2001 | Lin |
| 6,204,326 B1 | 3/2001 | Cook |
| 6,214,553 B1 | 4/2001 | Szostak et al. |
| 6,238,868 B1 | 5/2001 | Carrino et al. |

(Continued)

FOREIGN PATENT DOCUMENTS

| | | |
|---|---|---|
| EP | 0 231 495 | 12/1986 |
| EP | 0478319 | 4/1992 |

(Continued)

OTHER PUBLICATIONS

Beaudoing, E. et al., Genome Res. 2000;10:1001-1010.
Bouck, J. et al., Nucleic Acids Research, 1998;26:4516-4523.
Schwartz, S. et al., Genes Chromosomes Cancer, 2006;45:770-780.
Jones et al., Genome Research 2001;11:1346-1352.
Gregory et al., Molecular and Biochemical Parasitology 1997;87:85-95.
Forghani et al., J. Clin. Microbiology, 1991;29(BO3):583-591.
Baugh, L.R., et al., Quantitative Analysis of MNRA Amplification by In Vitro Transcription, Nucl. Acids Res. 29:E29 (2001).
Boule, J.B., et al., Terminal Deoxynucleotidyl Transferase Indiscriminately Incorporates . . . J. Biol. Chem. 276:31388-31393 (2001).

(Continued)

*Primary Examiner* — Kenneth Horlick
(74) *Attorney, Agent, or Firm* — Paul Diamond, Esq.

(57) ABSTRACT

This invention provides novel compositions and processes for analyte detection, quantification and amplification. Nucleic acid arrays and libraries of analytes are usefully incorporated into such compositions and processes. Universal detection elements, signaling entities and the like are employed to detect and if necessary or desirable, to quantify analytes. Amplification of target analytes are also provided by the compositions and processes of this invention.

32 Claims, 32 Drawing Sheets

(56) References Cited

U.S. PATENT DOCUMENTS

| | | | |
|---|---|---|---|
| 6,242,189 B1 | 6/2001 | Kustu et al. |
| 6,251,639 B1 | 6/2001 | Kurn |
| 6,261,782 B1 | 7/2001 | Lizardi |
| 6,268,147 B1 | 7/2001 | Beattie et al. |
| 6,268,171 B1 | 7/2001 | Meyer et al. |
| 6,277,579 B1 | 8/2001 | Lazar et al. |
| 6,280,954 B1 | 8/2001 | Ulfendahl |
| 6,326,489 B1 | 12/2001 | Church et al. |
| 6,344,317 B2 | 2/2002 | Urnovitz et al. |
| 6,376,191 B1 | 4/2002 | Yu |
| 6,379,932 B1 | 4/2002 | Arnold |
| 6,423,552 B1 | 7/2002 | Lu |
| 6,451,588 B1 | 9/2002 | Egholm |
| 6,479,650 B1 | 11/2002 | Kool |
| 6,485,944 B1 | 11/2002 | Church et al. |
| 6,500,620 B2 | 12/2002 | Yu |
| 6,531,300 B1 | 3/2003 | Haydock |
| 6,537,747 B1 | 3/2003 | Mills |
| 6,586,569 B1 | 7/2003 | Starzinski-Powitz |
| 6,696,256 B1 | 2/2004 | Li |
| 6,730,517 B1 | 5/2004 | Koster et al. |
| 6,743,605 B1 | 6/2004 | Rabbani et al. |
| 6,858,412 B2 | 2/2005 | Willis |
| 7,064,197 B1 | 6/2006 | Rabbani |
| 8,742,090 B2 | 6/2014 | Rabbani et al. |
| 2002/0004204 A1 | 1/2002 | O'Keefe |
| 2002/0110828 A1 | 8/2002 | Ferea et al. |
| 2002/0168640 A1 | 11/2002 | Li |
| 2003/0044817 A1 | 3/2003 | Laird |
| 2003/0050444 A1 | 3/2003 | Haydock |
| 2003/0077609 A1 | 4/2003 | Jakobsen |
| 2003/0082566 A1 | 5/2003 | Sylvan |
| 2003/0104460 A1 | 6/2003 | Rabbani et al. |
| 2003/0118595 A1 | 6/2003 | Niemeyer et al. |
| 2004/0110177 A1 | 6/2004 | Ullrich |
| 2004/0161741 A1 | 8/2004 | Rabani et al. |
| 2004/0197779 A1 | 10/2004 | Apffel |
| 2005/0100932 A1 | 5/2005 | Lapidus et al. |
| 2005/0202455 A1 | 9/2005 | Rabbani |
| 2005/0233343 A1 | 10/2005 | Rabbani |
| 2005/0238658 A1 | 10/2005 | Maskell et al. |
| 2006/0014156 A1 | 1/2006 | Rabbani |
| 2006/0099601 A1 | 5/2006 | Rabbani et al. |
| 2006/0257906 A1 | 11/2006 | Rabbani |
| 2007/0134707 A1 | 6/2007 | Gan et al. |

FOREIGN PATENT DOCUMENTS

| | | |
|---|---|---|
| EP | 0231495 | 8/1994 |
| EP | 0 667 393 A2 | 8/1995 |
| EP | 0667393 | 8/1995 |
| EP | 0846776 | 6/1998 |
| EP | 1041160 | 10/2000 |
| EP | 1201768 | 5/2002 |
| WO | WO92/08800 | 5/1992 |
| WO | WO 97/10365 | 3/1997 |
| WO | WO97/10385 | 3/1997 |
| WO | WO 98/45474 | 4/1998 |
| WO | WO 99/19510 | 4/1999 |
| WO | WO99/51773 | 10/1999 |
| WO | WO 99/58718 | 11/1999 |
| WO | WO 00/24936 | 5/2000 |
| WO | WO00/26406 | 5/2000 |
| WO | WO 00/32823 | 6/2000 |
| WO | WO 0075356 | 12/2000 |
| WO | WO 01/05835 | 1/2001 |
| WO | WO 01/36681 | 5/2001 |
| WO | WO 01/40803 | 6/2001 |

OTHER PUBLICATIONS

Komura, J., et al., Terminal Transferase-Dependent PGR: A Versatile and Sensitive Method . . . Nucl Acids Res.26:1807-1811 (1998).

Krupp, G. et al., Unusual Promoter-Independent Transcription Reactionswith Bacteriophage . . . Nucl. Acids Res. 17:3023-3036 (1989).

McGiness, K.E. et al., Substitution of Ribonucleotides in the T7 RNA Polymerase . . . J. Biol. Chem. 277:2987-2991 (2002).

Schenborn, E.T., et al., A Novel Transcription Property of SP6 and T7 RNA Polymerases . . . Nucl. Acids Res. 13:6223-6236 (1985).

Schmidt, W.M. et al., Controlled Ribonucleotide Tailing of CDNA Ends (CRTC) by Terminal . . . Nucl. Acids. Res. 24:1789-1791(1996).

Van Gelder, R.N. et al., Amplified RNA Synthesized From Limited Quantities Heterogenous CDNA, Proc. Natl. Acad Sci. USA 87:1663-1667 (1990).

Walker, G.T. et al., Isothermal In Vitro Amplification of DNA by a Restriction Enzyme . . . Proc. Natl. Acad. Sci. USA 89:392-396 (1992).

Adams., et al. Complementary DNA Sequencing: Expressed Sequence Tags . . . Science 252:1651-1656 (1991).

Afanassiev et al.,Preparation of DNA and Protein Micro Assays on Glass . . . Nucl. Acids Res. 28:E66 (2000).

Antopolsky, M. et al., Solid-Phase Synthesis of Peptide-Oligonucleotide . . . Helv. Chim Acta 82:2130-2140 (1999).

Arar, K., et al., Synthesis of Oligonucleotide-Peptide Conjugates . . . Tetrahedron Letter 34:8087-8090 (1993).

Arenkov, P., et al., Protein Microchips: Use for Immunoassay . . . Analytical Biochemistry 278:123-131 (2000).

Bazin, et al., Innovation and Perspectives in Solid Phase Synthesis . . . R. Epton, Mayflower Sci. Ltd. Birmingham, UK (1999).

Bergmann, F. et al., Solid Phase Synthesis of Directly Linked Peptide-Oligo . . . Tetrahedron Letters 36:1839-1842 (1995).

Brenner, S., et al., Encoded Combinatorial Chemistry, Proc. Natl. Acad. Sci. USA 89:5381-5383 (1992).

Cho, R.J., et al., A Genome-Wild Transcriptional Analysis . . . Mol. Cell 2:65-73 (1998).

De La Torre, B.G., et al., Stepwise Solid-Phase Synthesis . . . Tetrahedron Letters 35:2733-2736 (1994).

De La Torre, B.G., et al., Synthesis and Bonding Properties of Oligonucleotide-Peptide . . . Bioconjugate Chem. 10:1005-1012 (1999).

De Wildt, R.M., et al., Antibody Arrays for High-Output Screening . . . Nature Biotechnology 18:989-994 (2000).

Ede, N.J., et al., Routine Preparation of Thiol Oligonucleotides . . . Bioconjugate Chemistry 5:373-378 (1994).

Edwards, J.B.D.M., et al., Oligodeoxyribonucleotide Ligation . . . Nucl. Acids. Res. 19:5227-5232 (1991).

Endege, W.O., et al., Representative CDNA Libraries and Their Utility . . . Biotechniques 26:542-550 (1999).

Eritja, R., et al., Synthesis of Defined Peptide-Oligonucleotide Hybrids . . . Tetrahedron 47:4113-4120 (1991).

Gentalen, E. et al., A Novel Method for Determining Linkage Between DNA Sequences . . . , Nucl. Acid. Res.27:1485-1491 (1999).

Haab, B.B., et al.,Protein Microarrays for Highly Parallel Detection . . . Genome Biology 2:1-13 (2001).

Hirschhorn, J.N., et al., SBE-TAGS: An Array-Based Method for Efficient . . . Proc. Natl. Acad. Sci. USA 97:12164-12169 (2000).

Kwoh, D.Y., et al., Transcription-Based Amplification System and Detection . . . Proc. Natl. Acad. Sci. USA 86:1173-1177 (1989).

Koonin, E.V., et al., The Phyology of RNA-Dependent RNA Polymerase . . . J. Gen. Virol. 72:2197-2206 (1991).

Lakobashvill, R., et al., Low Temperature Cycled PCR Protocol . . . Nucl. Acids. Res. 27:1566-1568 (1999).

Lockhart, D.J., et al., Expression Monitoring by Hybridization to High-Density . . . ,Nature Biotechnology14:1675-1680 (1996).

Lueking, A., et al., Protein Microarrays for Gene Expression . . . ,Anal. Biochem 279:103-111 (1999).

Matz, M., et al., Amplification of CDNA Ends Based on Template-Switching . . . ,Nucleic Acids Res. 27:1558-1560 (1999).

Mendoza, L.G., et al., High-Throughput Microarray-Based Enzyme-Linked . . . Biotechniques 27:778-788 (1999).

(56) References Cited

OTHER PUBLICATIONS

Needels, M.C., et al., Generation and Screening of an Oligonucleotide-Encoded . . . ,Proc. Natl. Acad.Sci. USA 90:10700-10704 (1993).
Okamoto, T., et al., Microarray Fabrication With Covalent Attachment of DNA . . . Nature Biotechnology 18:438-441 (2000).
Pastinen, T., et al., A System for Specific, High Throughput Genotyping . . . , Genome Research 10:1031-1042 (2000).
Pergolizzi, et al., U.S. Appl. No. 08/479,995, filed Jun. 7, 1995 Based on Priority U.S. Appl. No. 06/491,929, filed May 5, 1983.
Perou, C.M., et al., Distinctive Gene Expression Patterns in Human Mammary . . . ,Proc. Natl. Acad. Sci. USA 96:9212-9217 (1999).
Rabbani et al., U.S. Appl. No. 08/574,443, filed Dec. 15, 1995 Abandoned in Favor for U.S. Appl. No. 08/976,632, filed Nov. 25, 1997 and Published as U.S. 2003-0104620.
Robles, J., et al., Towards Nucloepeptides Containing Any Trifunctional . . . Tetrahedron 55:13251-13264 (1999).
Spellman, et al., Comprehensive Identification of Cell Cycle-Regulated . . . Mol. Biol. Cell 9:3273-3297 (1998).
Stetsenko, D.A., et al., Efficient Conjugation of Peptides to Oligonucleotides . . . J. Org. Chem. 65:4900-4908 (2000).
Taton, T.A. et al., Scanometric DNA Array Detection With Nanoparticle Probes, Science 289:1757-1760 (2000).
Tung, C.H., et al., Preparation and Applications of Peptide . . . Bioconjugate Chemistry 11:605-618 (2000).
Wang, E., et al., High-Fidelity MRNA Amplification for Gene Profiling . . . Nature Biotechnology 18:457-459 (2000).
Weslin, L., et al., Anchored Multiplex Amplification on a Microelectric . . . Biotechnology 18:199-204 (2000).
Yershov, G., et al., DNA Analysis and Diagnostics on Oligonucleotide . . . Proc. Natl. Acad. Sci. USA 93:4913-4918 (1996).
Ying-S-Y., et al., Generation of Full-Length CDNA Library From Single Human . . . ,Biotechniques 27:140-414 (1999).
Borson et al., A Lock-Docking Oligo (DT)Primer for 5' and 3' Race PCR . . . , Methods and Applications (1992) 2:144-148.
Moran et al., Non-Hydrogen Bonding 'Terminator' Nucleosides Increase . . . Nucl. Acid. Res. (1996) 24(11):2044-2052.
Steffens, et al., An Infrared Fluorescent DATP for Labeling DNA, Genome Research (1995) 5:393-399.
Bulyk, et al., Exploring the DNA-Binding Specificities of Zinc Fingers . . . , Proc. Natl. Acad. Sci. USA vol. 98, No. 13, Jun. 19, 2001, 7158-7163.
Morrissey et al., Nucleic Acid Hybridization Assays Employing DA-Tailed Capture Probes . . . , Mol. and Cell. Probes, vol. 3, Jan. 1989, 189-207.
Austermann et al., Biochemical Pharmacology, 1992, vol. 43(12) pp. 2581-2589.
U.S. Appl. No. 08/574,443, filed Dec. 15, 1995, Rabbani et al.
Dietrich et al., "Gene assmbly based on blunt-ended double-stranded DNA-molecules," *Biotechnology Techniques*, vol. 12, No. 1, pp. 49-54 (1998).
Drygin, "Natural covalent complexes of nucleic acids and proteins: some comments on practice and theory on the path from well-known complexes to new ones," *Nucleic Acid Research*, vol. 26, No. 21, pp. 4791-4796 (1998).
Giller et al., "Incorporation of reporter molecule-labled nucleotides by DNA polymerases. I. Chemical synthesis of various reporter group-labled 2'deoxyribonucleoside-5'-triphosphates," *Nucleic Acids Research*, vol. 31, No. 10, pp. 2630-2635 (2003).
Nam et al., "Oligo(dT) primer generates a high frequency of truncated cDNAs through internal poly(A) priming during reverse transcription," *Proceedings of the National Academy of Sciences*, vol. 99, No. 9, pp. 6152-6156 (2002).
Petrik et al., "High throughput PCR detection of HCV based on semiautomated multisample RNA capture," *Journal of Virological Methods*, vol. 64, pp. 147-159 (1997).
Stinear et al., "Detection of a single viable Cryptosporidium parvum oocyst in environmental water concentrates by reverse transription-PCR," *Applied and Environmental Microbiology*, vol. 62, No. 9, pp. 3385-3390 (1996).
Eisen et al., "Cluster analysis and display of genome-wide expression patterns," *Proc. Natl. Acad. Sci.*, vol. 95, pp. 14863-14868 (1998).
Armour, "Isolation of human minisatellite loci detected by synthetic tandem repeal probes: direct comparison with cloned DNA fingerprinting probes," *Human Molecular Genetics*, vol. 1, No. 5, pp. 319-323 (1992).
Jones et al., Changes in Gene Expression Associated With Developmental Arrest and Longevity in . . . Genome Research, 2001, 11:1346-1352.
Gregory et al., Differentially Expressed Abundant Trans-Spliced CDNAs From Larval Brugia Malayi, Molecular and Biochemical Parasitology, 1997, 87:85-95.
Forghani et al., 1991, J. Clin. Microbiol. vol. 29, BO 3, pp. 583-591.
Morrissey, D.V., Colins, M.L., Nucleic Acid Hybridization Assays Employing dA-Tailed Capture Probes . . . , Molecular Cellular Probes, 1989, Jun. 1989, 3(2):189-207.
Austermann et al., Biological Pharmacology, 1992, vol. 43(12), pp. 2581-2589.
Van Gelder, R.N., Amplified RNA Synthesized From Limited Quantities of Heterogenous CDNA, Proc. Natl. Acad Sci. USA 87:1663-1667 (1990).
Walker, G.T., et.al., Isothermal In Vitro Amplification of DNA by a Restriction . . . Proc. Natl. Acad. Sci. USA 89:392-396 (1992).
Baugh, L.R., et al., Quantitative Analysis of MRNA Amplification by In Vitro Transcription, Nucleic Acid Research 29; E29 (2001).
Boule, J-B., et al., Terminal Deoxynucleotidyl Transferase Indiscriminately Incorporates Ribonucleotides . . . , J. Biol. Chem. 276:31388-31393 (2001).
Komura., et al., Terminal Transferase-Dependent PCR: A Versatile and Sensitive . . . Nucleic Acid Research 26:1807-1811 (1998).
Krupp, G., et al., Unusual Promoter-Independent Transcription Reactions With . . . Nucleic Acids Research 17:3023-3036 (1989).
McGuinness, K.E., et al.,Substition of Ribonucleotides in the T7 RNA Polymerase Promoter . . . ,J. Biol. Chem. 277:2987-2991 (1992).
Schenborn, E.T., et al., A Novel Transcription Property of SP6 and T7 RNA Polymerases . . . , Nucleic Acids Research 13:6223-6236 (1985).
Schmidt, W.M., et al., Controlled Ribonucleotide Tailing of CDNA Ends (CRTC) by Terminal . . . , Nucleic Acids Research 24:1789-1791 (1996).

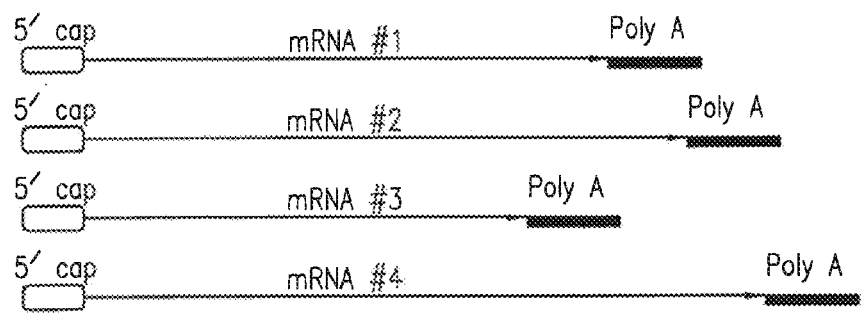
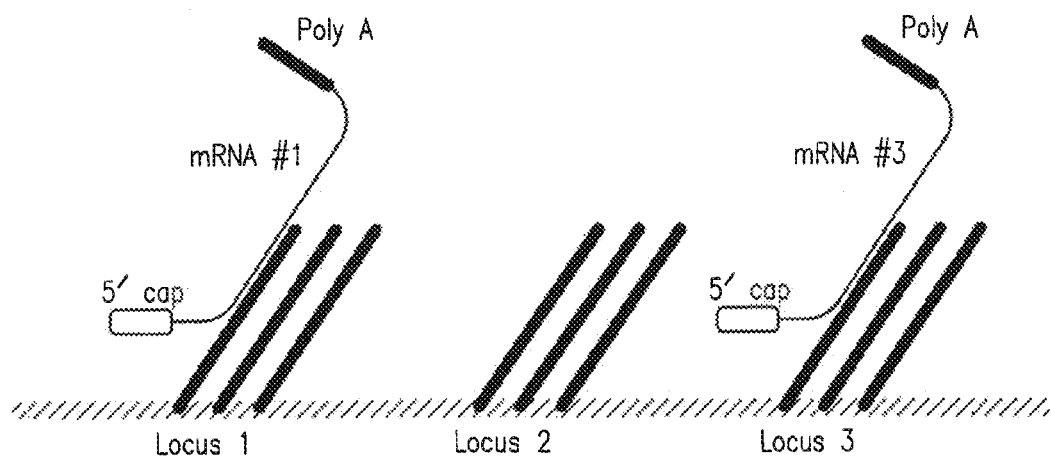
FIG. 1

(A) RNA substrate
5'                                                                    3'
(B) Fragmentation of RNA substrate
(C) addition of tails (UDTs) to RNA fragments
(D) Detection of tails (UDTs) on RNA fragments by binding a reagent containing signal groups (S)
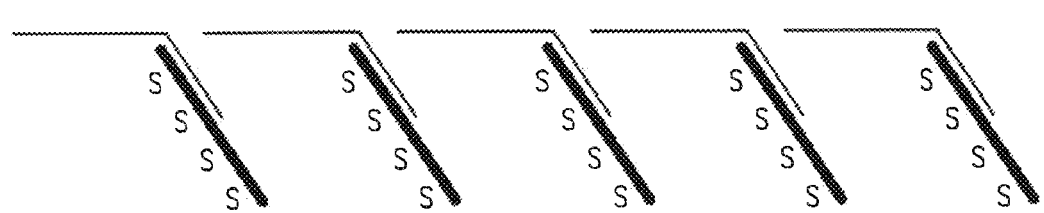
FIG. 2

(A) RNA Substrate
(B) Binding of Primer to RNA Substrate
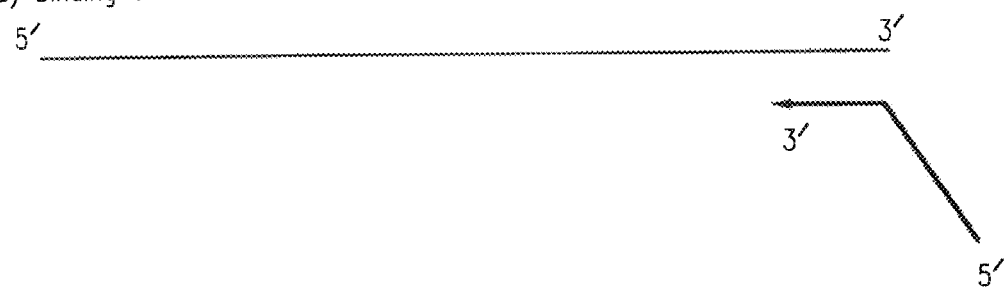
(C) Extension of Primer using RNA as template
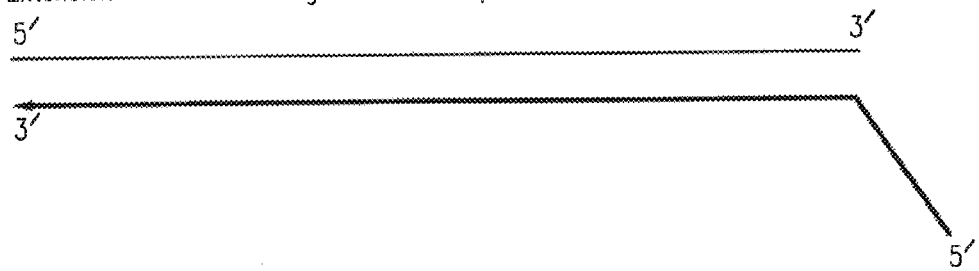
(D) Template Independent Extension of Primer
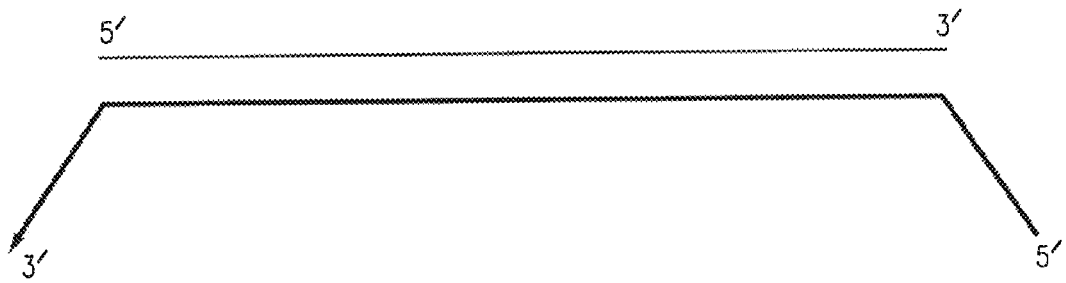
FIG. 3

(A) RNA substrate
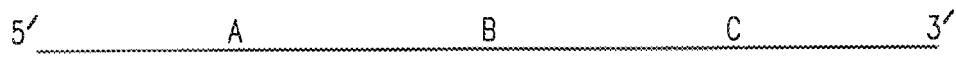
(B) Binding of Primer to RNA Substrate
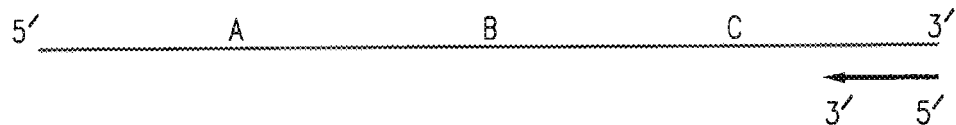
(C) Extension of Primer using RNA as template
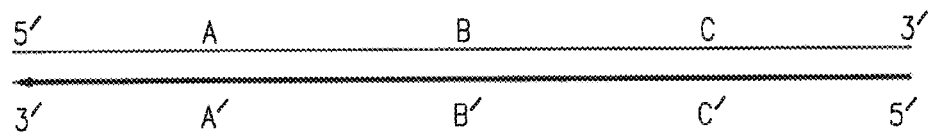
(D) Binding of random primers to 1st cDNA strand
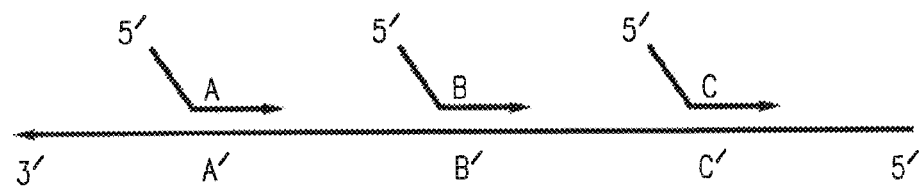
(E) Extension and strand displacement of random primers
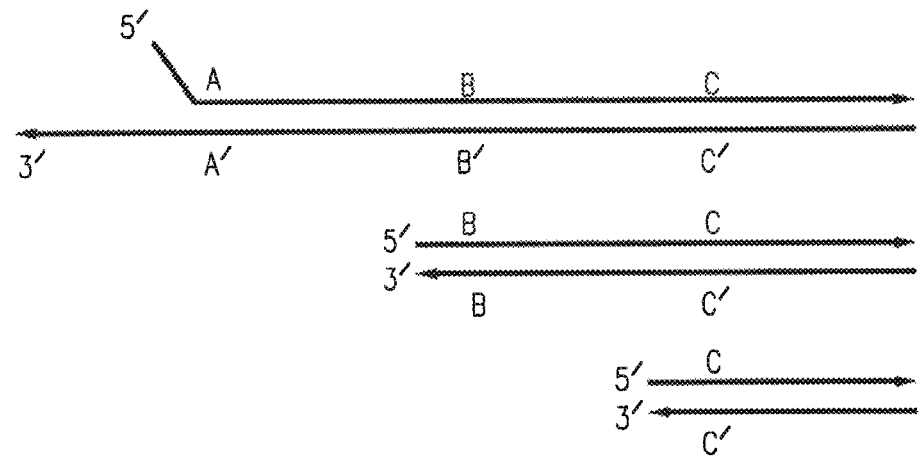
FIG. 4

(1) Binding of random primers to 1st cDNA strand
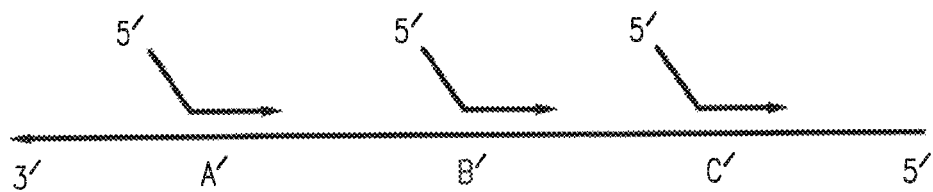
(2) Extension of random primers using 1st cDNA strand as template
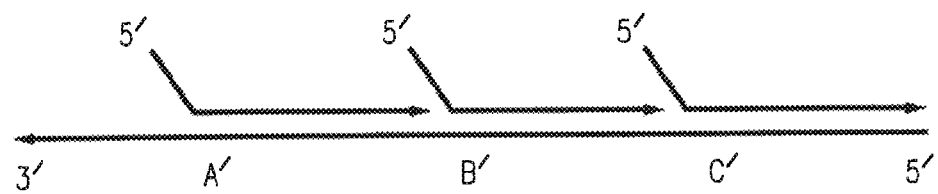
(3a) Creation of functional promoters by binding of complementary strand
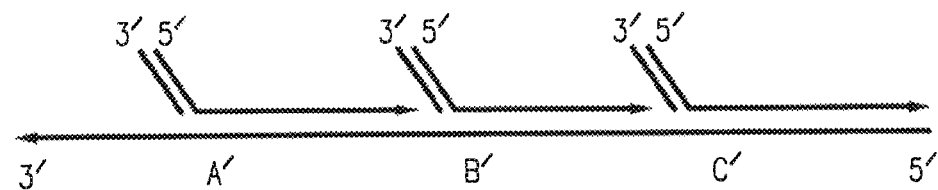
(3a) Creation of functional promoters by self-complementary sequences
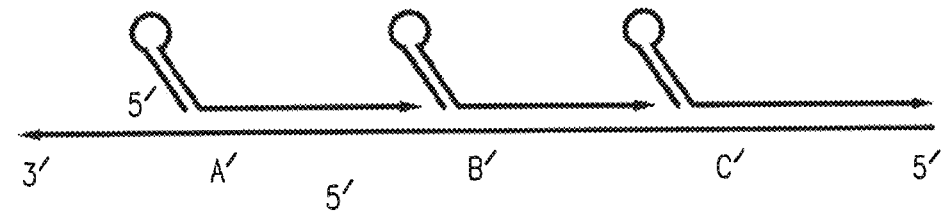
FIG. 5

(A) Binding of Primer to analyte
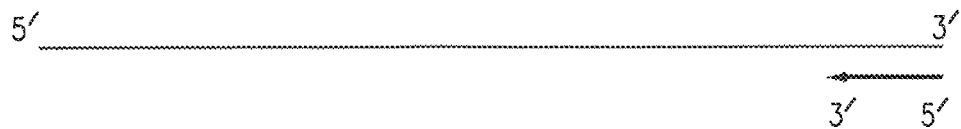
(B) Extension of Primer using analyte as template
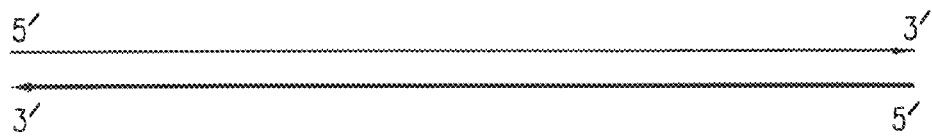
(C) Template Independent addition of dCTP
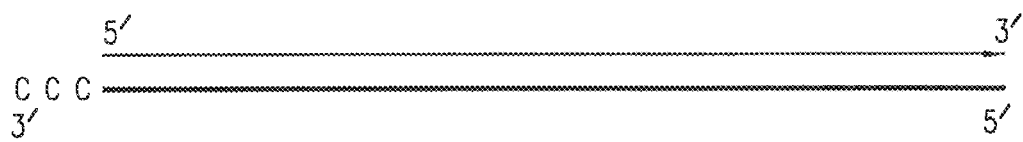
(D) Use of 3′ end of 1st cNA strand for binding of Primer with T7 promoter
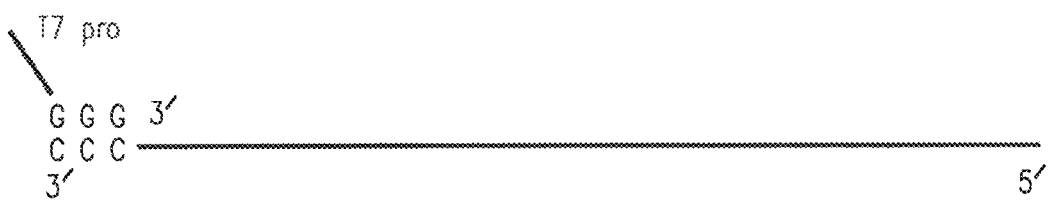
(E) Binding of Primer with T7 promoter to internal sequenced of cNDNA
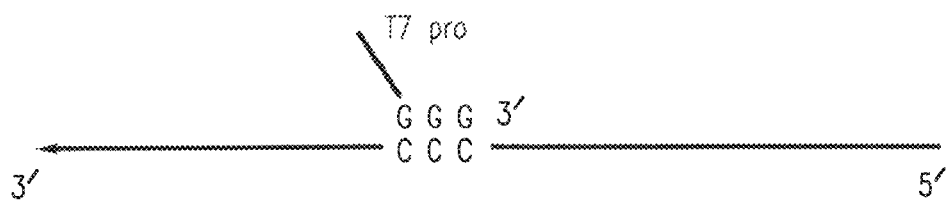
FIG. 6

(A) RNA Substrate
(B) Binding of Primer to RNA substrate
(C) Extension of Primer using RNA as template
(D) Template Independent addition of dCTP by Terminal Transferase
(E) Use of 3′ end of 1st cDNA strand for binding of Primer with T7 promoter
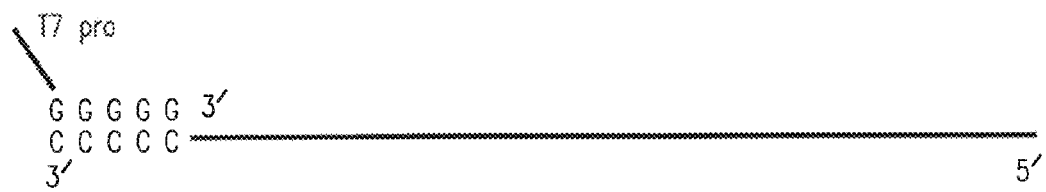
FIG. 7

1) analyte
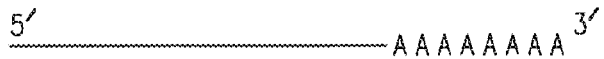
2) cNA copy made from analyte
3a) double-stranded oligonucleotide ligated to RNA/DNA hybrid by T4 DNA ligase
3b) single-stranded oligonucleotide ligated to a single-stranded 3′ tail by T4 RNA ligase
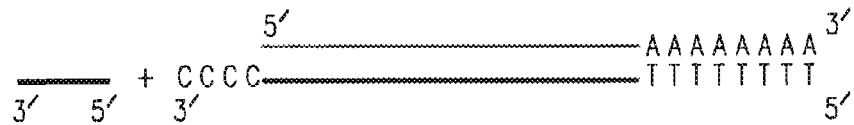
3c) double-stranded oligonucleotide ligated to single-stranded 3′ tail by T4 DNA ligase
FIG. 8

(A) RNA Substrate
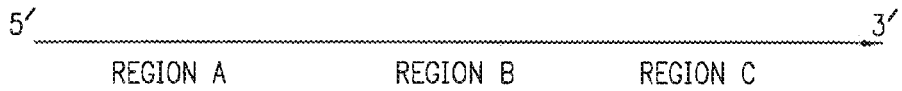
(B) Binding of Primer to RNA Substrate
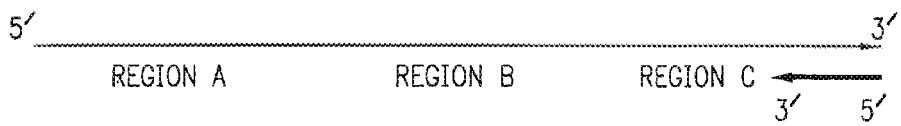
(C) Extension of Primer using RNA as template
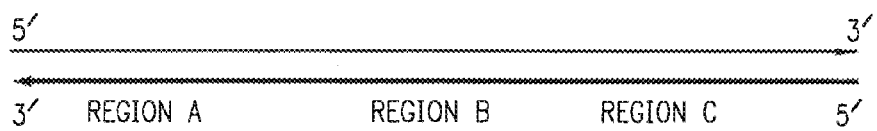
(D) Nicking of cDNA strand followed by release from RNA template
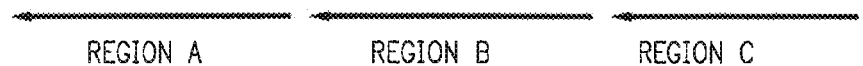
(E) Template independent addition of dCTP and binding of primer with T7 Promoter
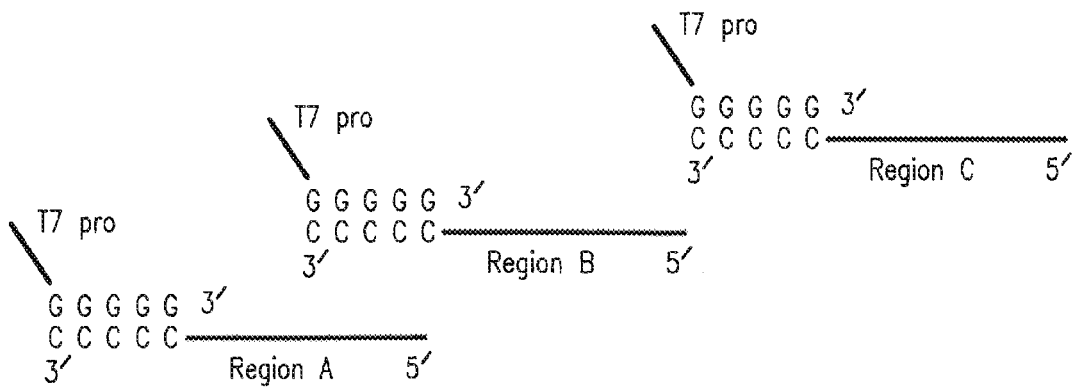
FIG. 9

(A) Capture of poly A mRNA with oligo-T beads
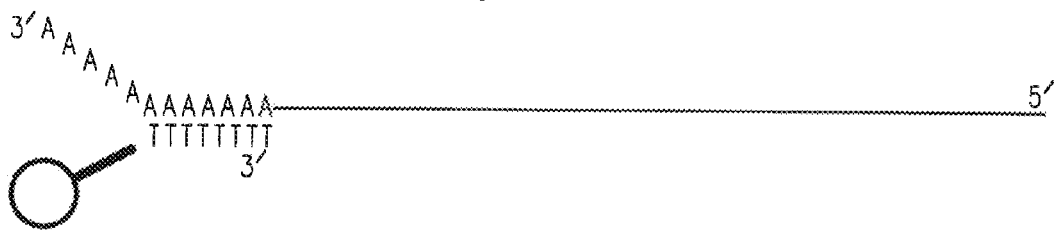
(B) Extension of Oligo T with poly A mRNA as template
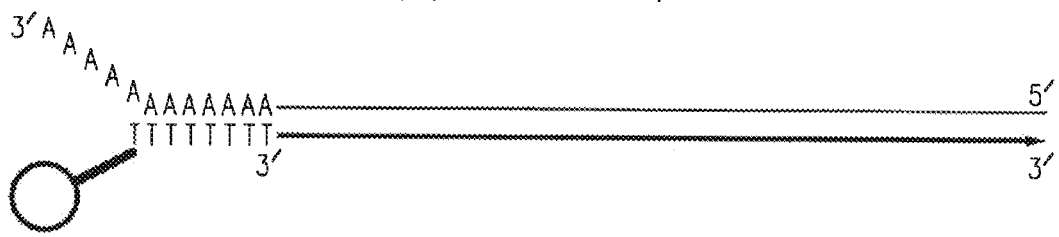
(C) Removal of poly A mRNA and binding of random primers with T7 promoter sequence
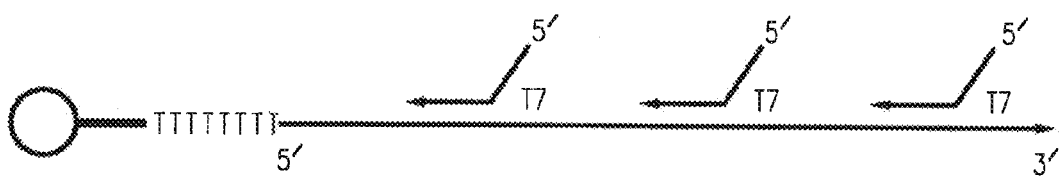
(D) Extension of primers and strand displacement of extended primers
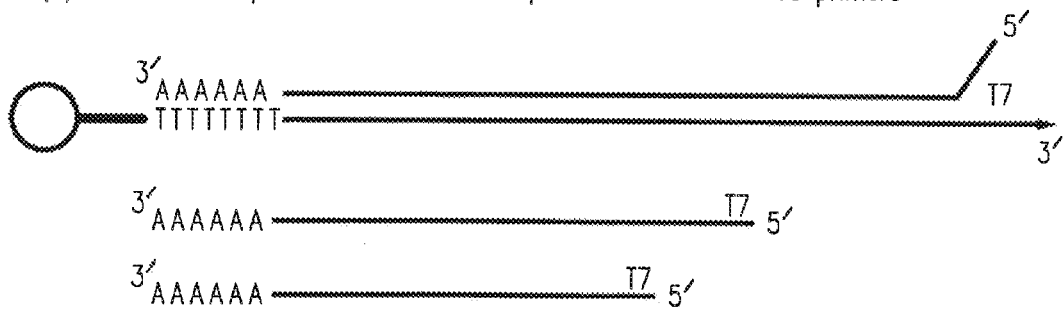
FIG. 10

(A) Sandwich Capture of poly A mRNA
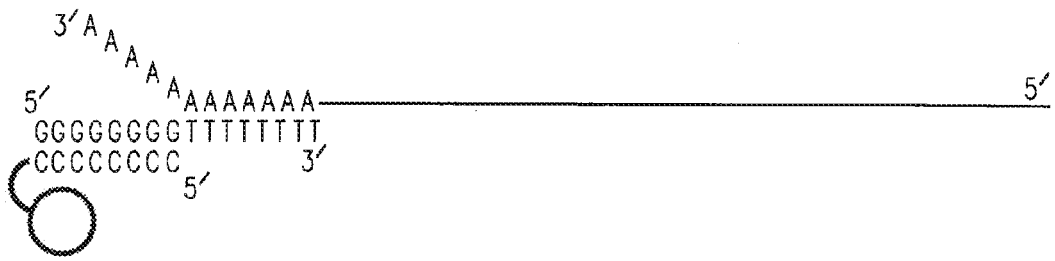
(B) Extension of Oligo T with poly A mRNA as template
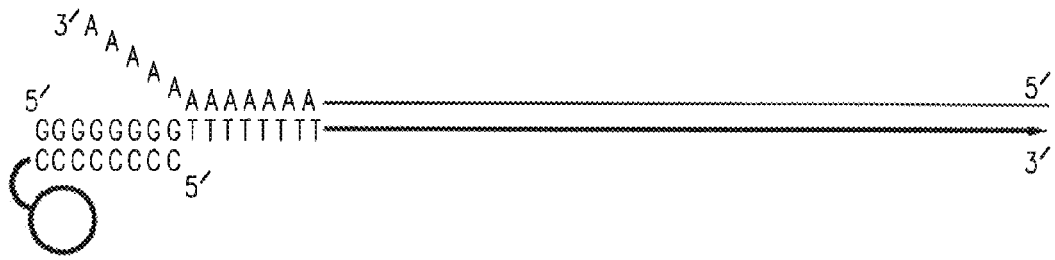
(C) Removal of poly A mRNA and binding of random primers with T7 promoter sequence
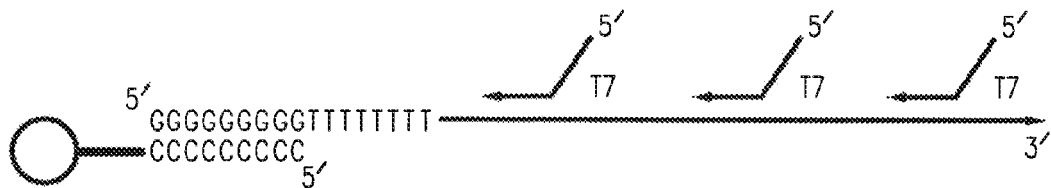
(D) Extension of primers and strand displacement of extended primers
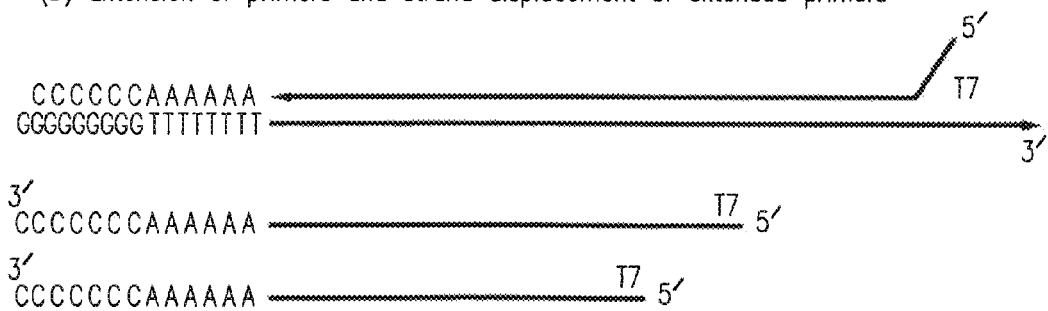
FIG. 11

(A) Capture of poly A mRNA with oligo-T beads
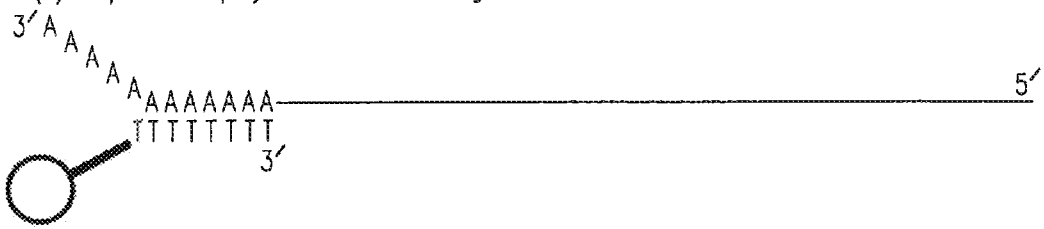
(B) Extension of Oligo T with poly A mRNA as template
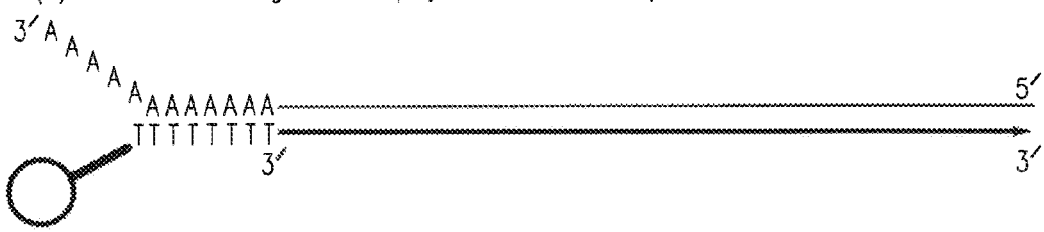
(C) Removal of poly A mRNA and binding of random primers to 1st cDNA strand
(D) Extension of random primers and strand displacement of extended primers
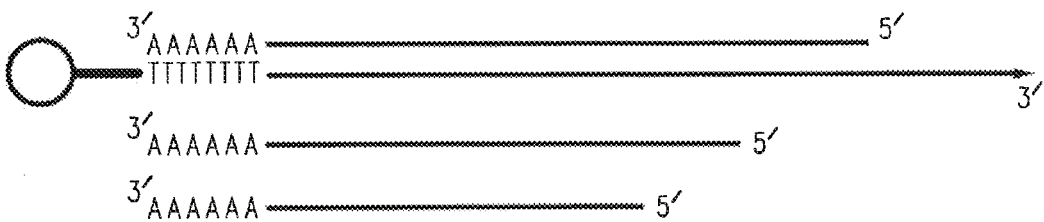
(E) Hybridization of oligo-T/T7 Pro primers to 2nd cDNA strands
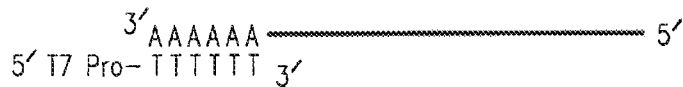
(F) Extension of oligo-T/T7 Pro primers and 2nd cDNA strands
FIG. 12

(A) Poly A RNA Target
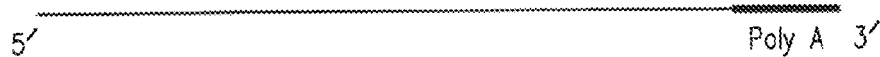
5′                                            Poly A   3′
(B) Ligation of UDT to 5′ end of Target
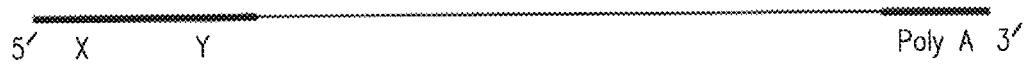
5′   X       Y                               Poly A   3′
(C) Binding of primer to 3′ end of Target
                                                    Primer 1
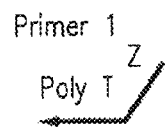
5′   X       Y                               Poly A   3′
(D) Extension of primer
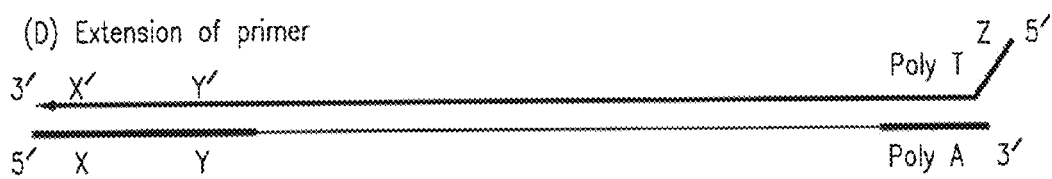
(E) Addition of Primers for Isothermal Amplification
(F) Unit length Isothermal Amplicon
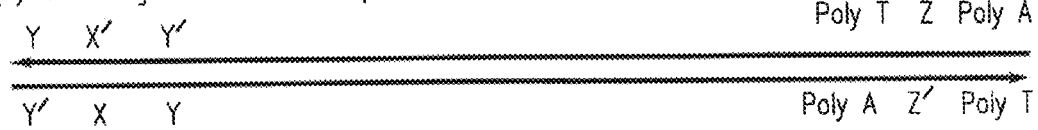
FIG. 13

(A) Poly A RNA Target
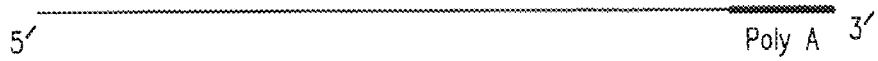
5'  ———————————————————————————————— Poly A  3'
(B) Ligation of UDT to 5' end of Target
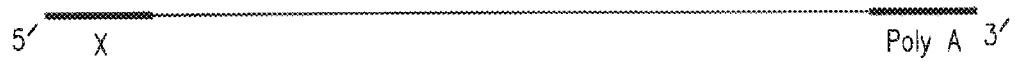
5'  X ———————————————————————————————— Poly A  3'
(C) Binding of primer to 3' end of Target
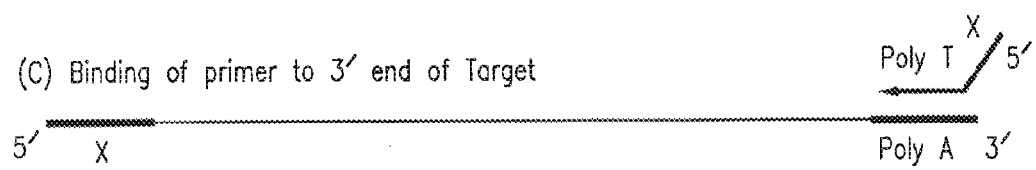
                                                    Poly T  X / 5'
5'  X ———————————————————————————————— Poly A  3'
(D) Extension of primer
3'  X' ———————————————————————————————— Poly T  X  5'
5'  X  ———————————————————————————————— Poly A  3'
(E) Addition of SDA Primer
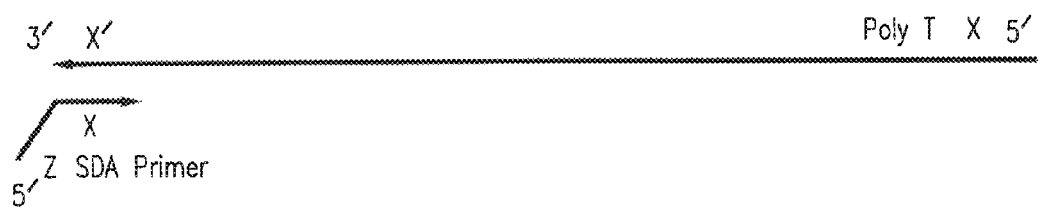
3'  X' ———————————————————————————————— Poly T  X  5'
        X
5'  Z   SDA Primer
(F) Unit length SDA Amplicon
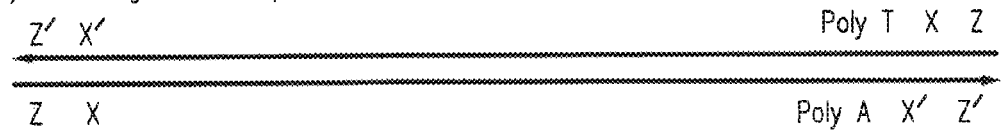
  Z' X' ———————————————————————————————— Poly T  X  Z
  Z  X  ———————————————————————————————— Poly A  X' Z'
FIG. 14

(A) Poly A RNA Target
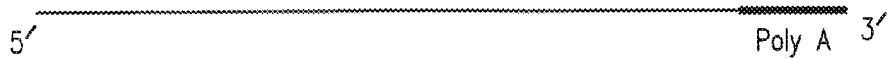
5'　　　　　　　　　　　　　　　　　　　　　　　　　Poly A　3'
(B) Binding of primer to 3' end of Target
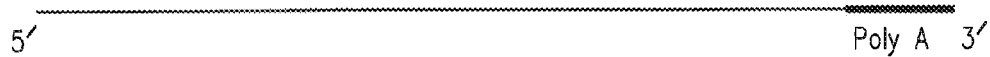
Poly T  X  5'
5'　　　　　　　　　　　　　　　　　　　　　　　　　Poly A　3'
(C) Extension of primer
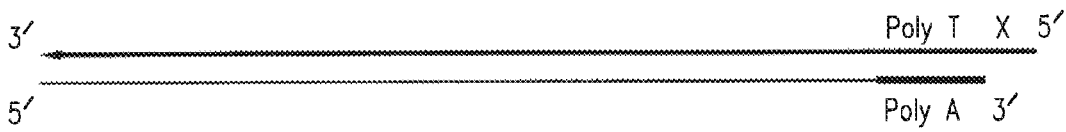
3'　　　　　　　　　　　　　　　　　　　　　　　Poly T  X  5'
5'　　　　　　　　　　　　　　　　　　　　　　　Poly A  3'
(D) Addition of UDT (Q) to 3' end of first copy
3'  Q　　　　　　　　　　　　　　　　　　　　　Poly T  X  5'
(E) Addition of Primer for binding to Q
3'  Q　　　　　　　　　　　　　　　　　　　　　Poly T  X  5'
Q'
Z'
5'
(F) Unit length Amplicon
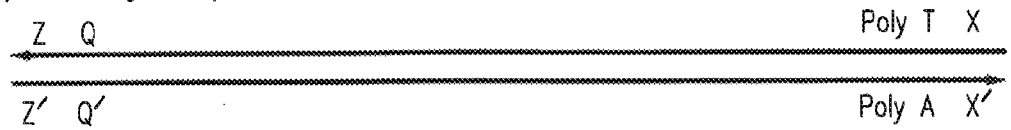
Z  Q　　　　　　　　　　　　　　　　　　　　　Poly T  X
Z' Q'　　　　　　　　　　　　　　　　　　　　　Poly A  X'
FIG. 15

(1) Array with SPE's complementary to analyte "P" at Locus P, SPE's complementary to analyte "Q" at Locus Q and SPE's complementary to analyte "R" at Locus R and with UPE's comprising Poly T sequences at all three loci
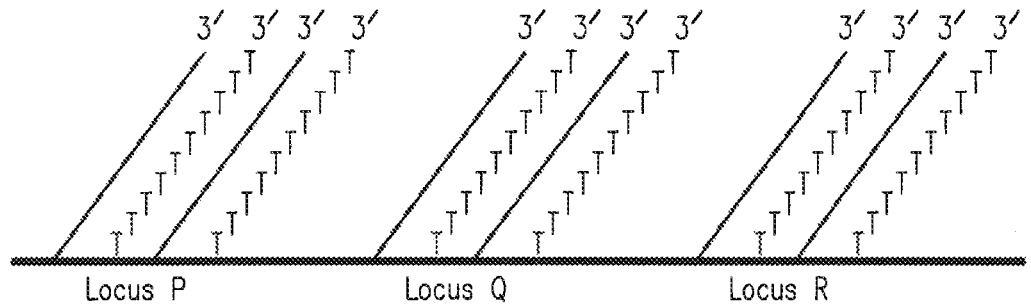
(2) Binding of analyte "P" to corresponding SPE at Locus P
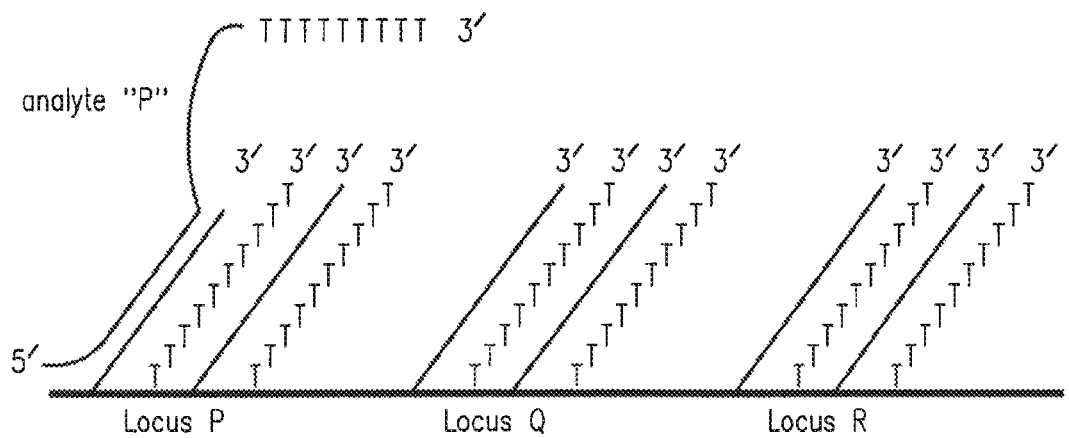
FIG. 16
Binding of an analyte to an array with SPE's and UPE's Extension of an SPE Binding of a UPE to an extended SPE followed by extension of the UPE Binding of extended SPE's and UPE's to un-extended SPE's and UPE's

| LOCUS 1 | LOCUS 2 | LOCUS 3 | LOCUS 4 |
|---|---|---|---|
| SPE 1 | SPE 2 | SPE 3 | SPE 4 |
| UPE 1 | UPE 1 | UPE 1 | UPE 1 |

| LOCUS 5 | LOCUS 6 | LOCUS 7 | LOCUS 8 |
|---|---|---|---|
| SPE 5 | SPE 6 | SPE 7 | SPE 8 |
| UPE 1 | UPE 1 | UPE 1 | UPE 1 |

| LOCUS 9 | LOCUS 10 | LOCUS 11 | LOCUS 12 |
|---|---|---|---|
| SPE 1 | SPE 2 | SPE 3 | SPE 4 |
| UPE 2 | UPE 2 | UPE 2 | UPE 2 |

| LOCUS 13 | LOCUS 14 | LOCUS 15 | LOCUS 16 |
|---|---|---|---|
| SPE 5 | SPE 6 | SPE 7 | SPE 8 |
| UPE 2 | UPE 2 | UPE 2 | UPE 2 |

*FIG. 20*

Amplification Array for Comparative Analysis (1) Digestion of DNA with restriction enzyme R1
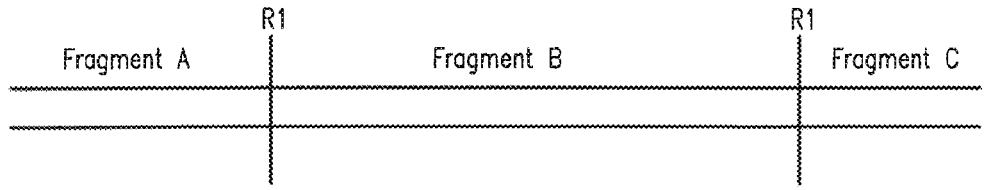
(2) Ligation of UDE's to DNA fragments
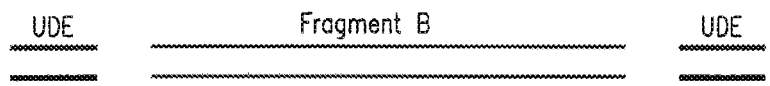
(3) Binding and extension of SPE primers with different 3′ ends followed by extensions with UPE primers
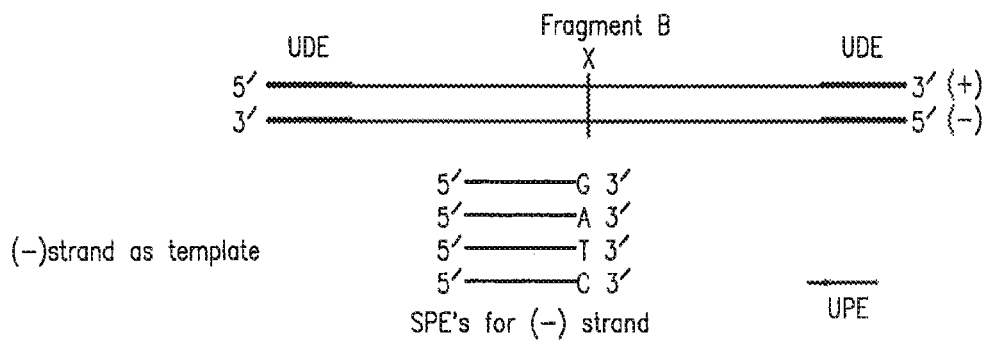
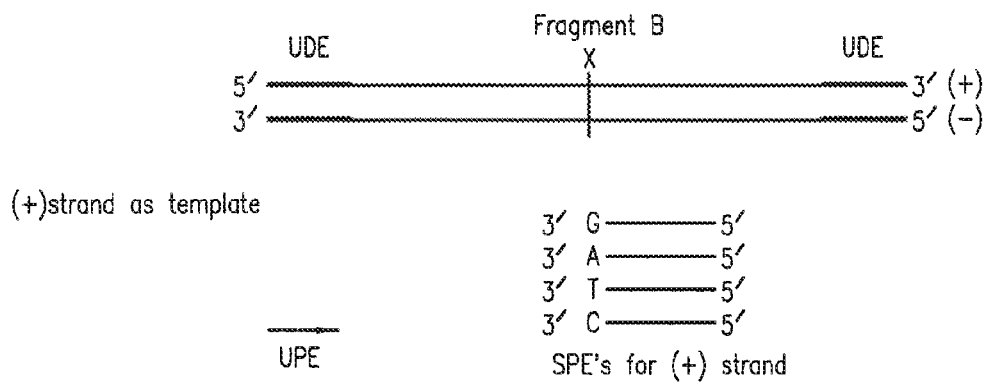
FIG. 21
Use of an array with SPE's and UPE's for SNP analysis

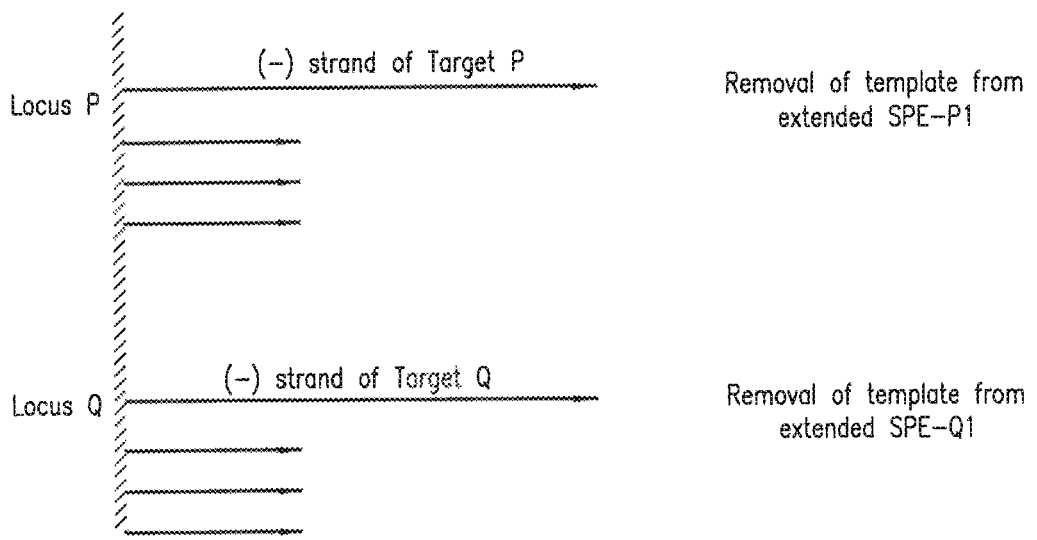
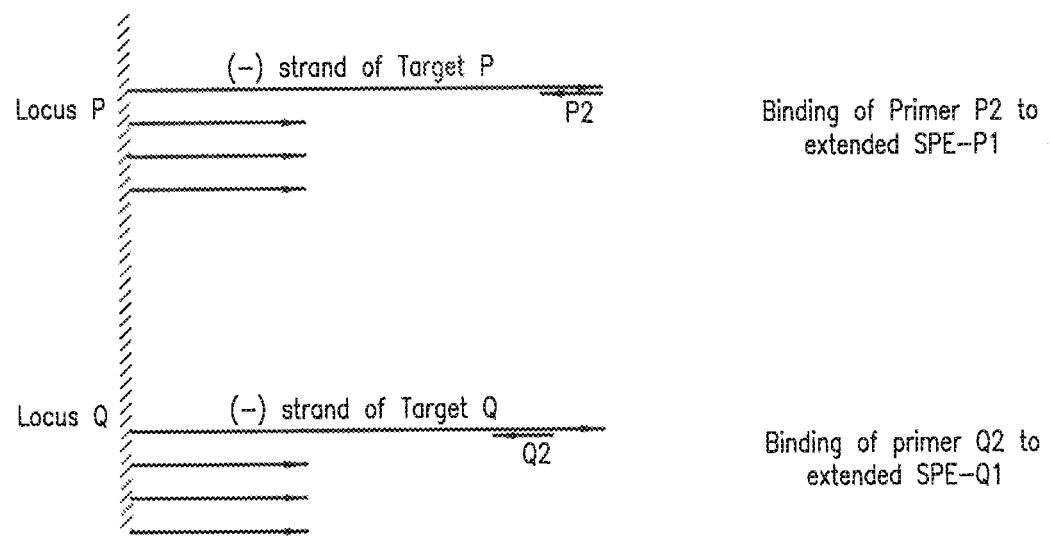
FIG. 23

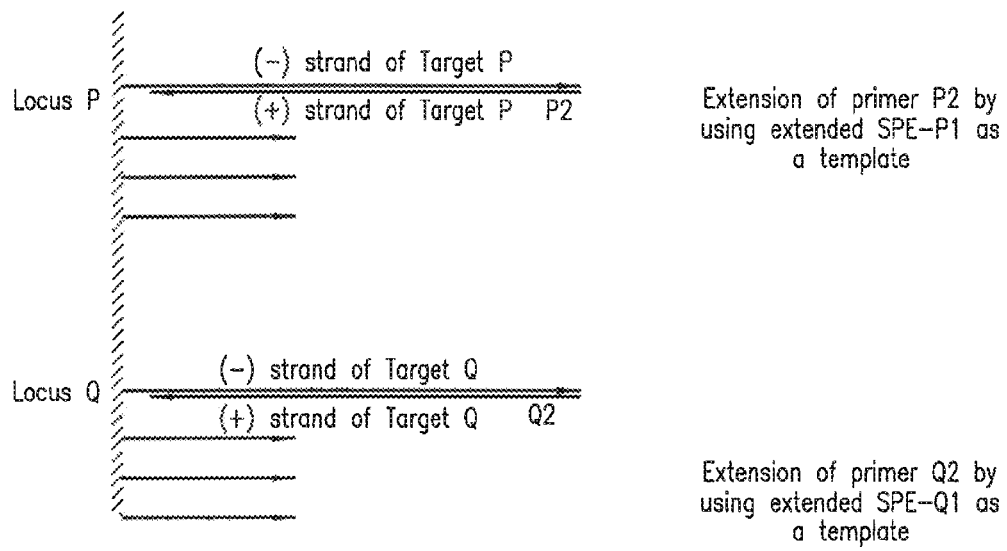
Extension of primer P2 by using extended SPE-P1 as a template
Extension of primer Q2 by using extended SPE-Q1 as a template
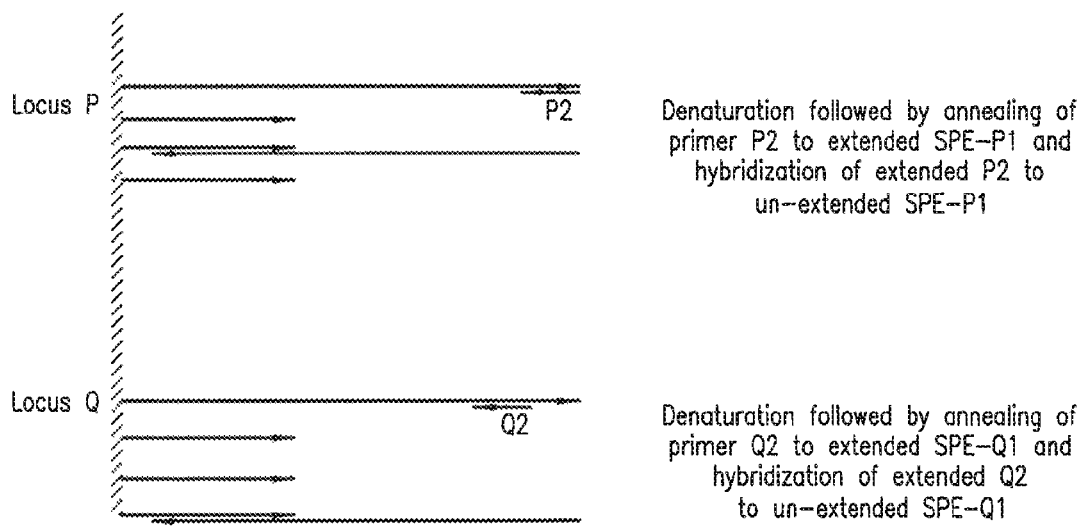
Denaturation followed by annealing of primer P2 to extended SPE-P1 and hybridization of extended P2 to un-extended SPE-P1
Denaturation followed by annealing of primer Q2 to extended SPE-Q1 and hybridization of extended Q2 to un-extended SPE-Q1
FIG. 24

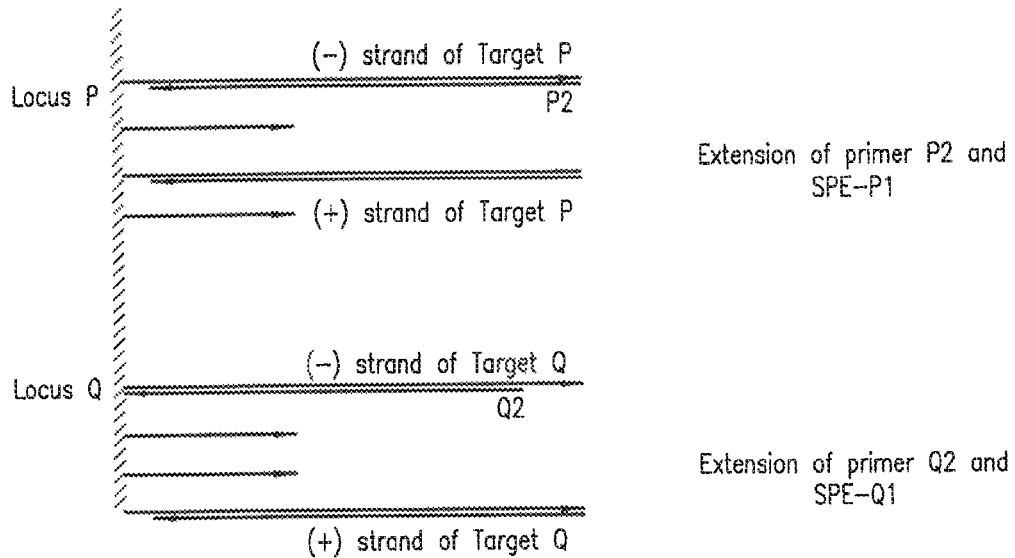
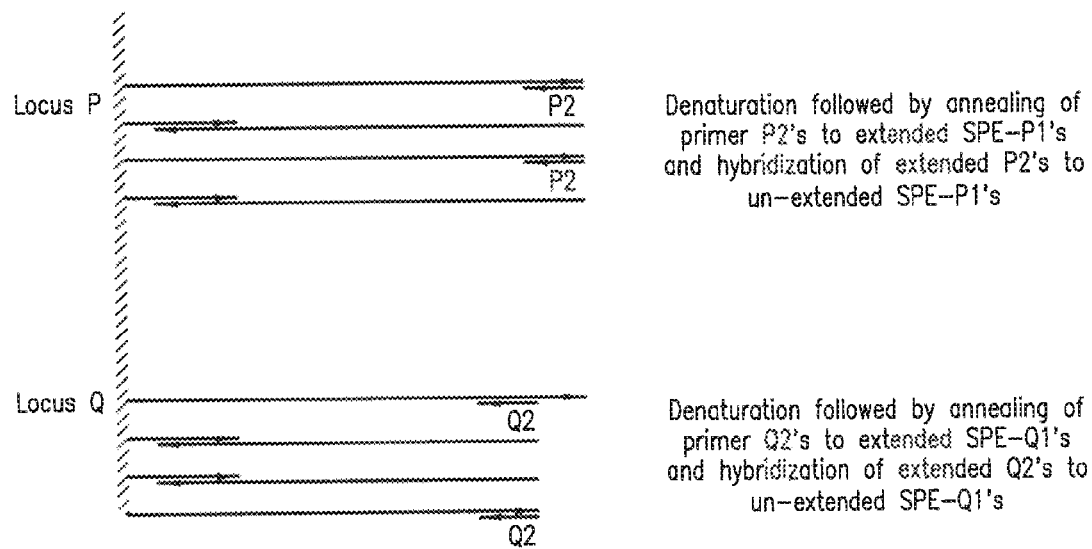
FIG. 25

A) Mixture of Library of Peptide analytes with a Library of Peptide/NAs
B) Binding of Peptide analyte #1 to Peptide/NA #1
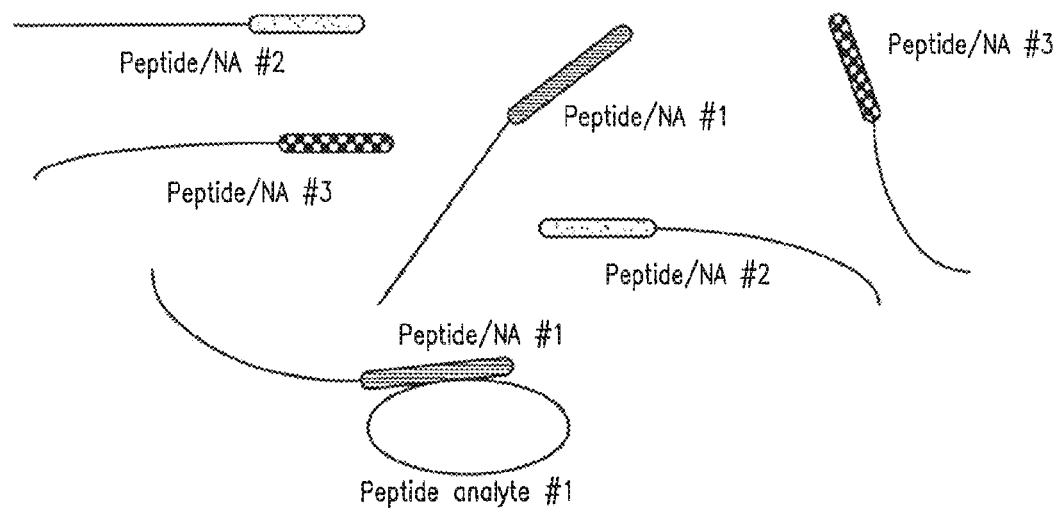
C) Binding of Peptide/NAs to matrix through complementary sequences
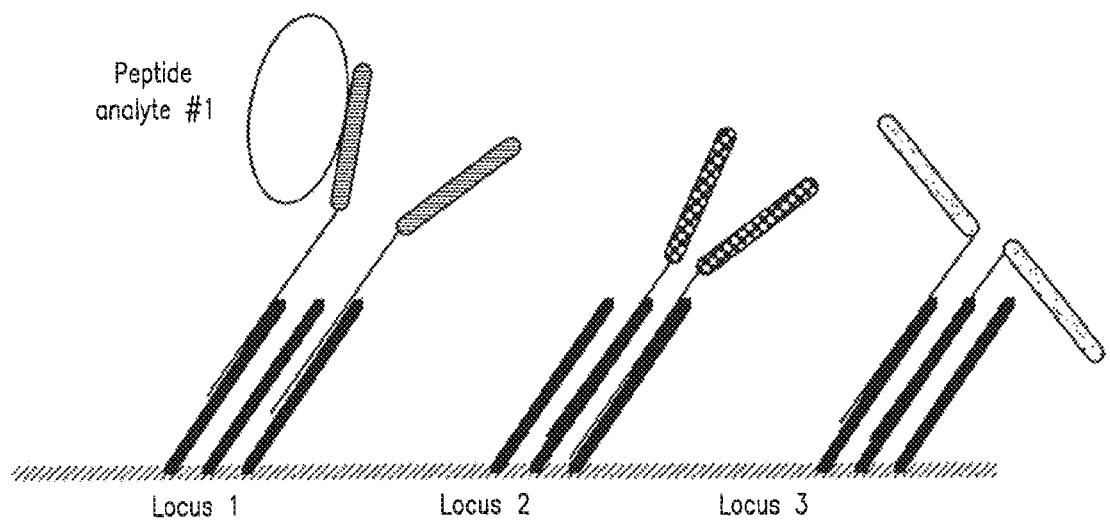
FIG. 26

1. Transcription product
2. 1kb PLUS DNA ladder 2000 bp
1650 bp

1. Transcription product
2. 1kb PLUS DNA ladder

1. Random primers −2 μl
2. T7-C9 primers without TdT tailing −2 μl
3. T7-C9 primers after TdT tailing −2 μl
4. 1 kb PLUS DNA Ladder
5. Random primers −10 μl
6. T7-C9 primers without TdT tailing −10 μl
7. T7-C9 primers after TdT tailing −10 μl
8. 1 kb PLUS DNA Ladder 1. Taq pol. 1 cycle
2. Taq pol. 5 cycles
3. Tth pol. 1 cycle
4. Tth pol. 5 cycles
5. 1 kb PLUS DNA Ladder

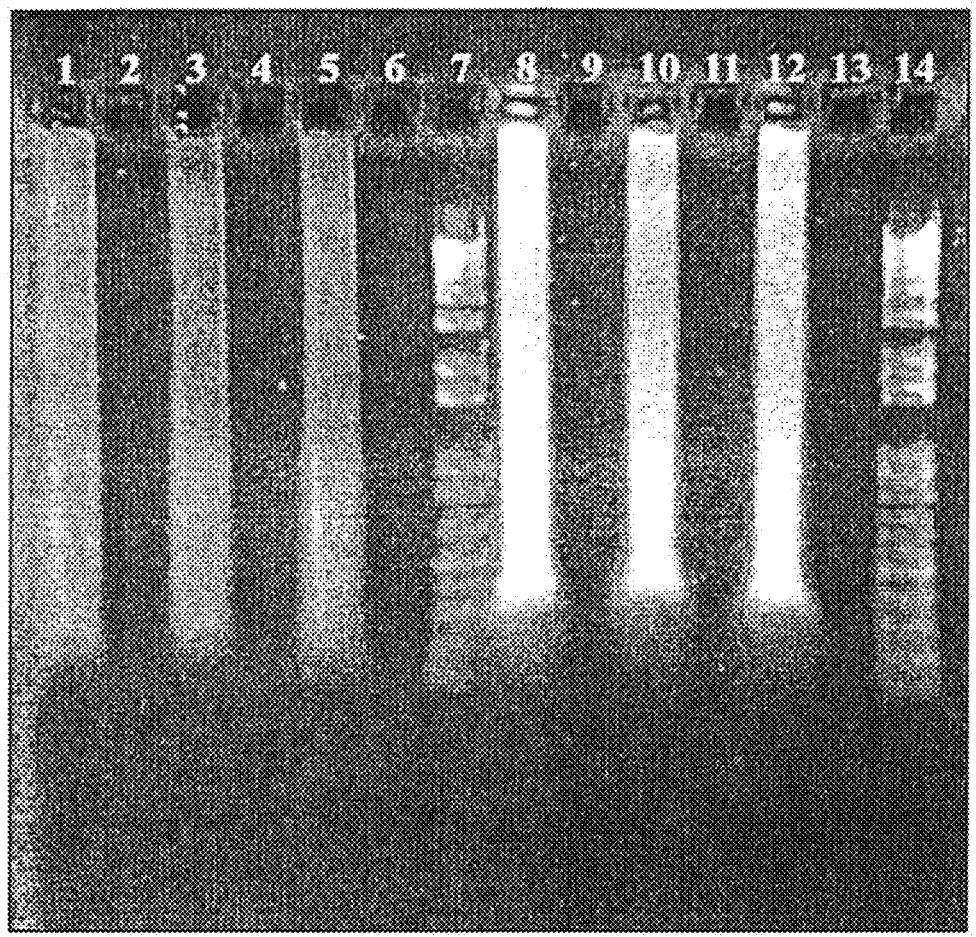

1. SAMPLE 1-4 μl TRANSCRIPTION PRODUCT
2. SAMPLE 1-1 μl DNA TEMPLATE
3. SAMPLE 2-4 μl TRANSCRIPTION PRODUCT
4. SAMPLE 2-1 μl DNA TEMPLATE
5. SAMPLE 3-4 μl TRANSCRIPTION PRODUCT
6. SAMPLE 3-1 μl DNA TEMPLATE
7. 1 kb PLUS DNA LADDER
8. SAMPLE 1-10 μl TRANSCRIPTION PRODUCT
9. SAMPLE 1-2.5 μl DNA TEMPLATE
10. SAMPLE 2-10 μl TRANSCRIPTION PRODUCT
11. SAMPLE 2-2.5 μl DNA TEMPLATE
12. SAMPLE 3-10 μl TRANSCRIPTION PRODUCT
13. SAMPLE 3-2.5 μl DNA TEMPLATE
14. 1 kb PLUS DNA LADDER

FIG. 32

1. 1 kb PLUS DNA LADDER
2. – – – –
3. SUPERSCRIPT II (LIFE TECHNOLOGIES)
4. M-MuLV (LIFE TECHNOLOGIES)
5. M-MuMuLV (NEW ENGLAND BIOLABS)
6. ENHANCED AMV (SIGMA)
7. AMV (LIFE TECHNOLOGIES)
8. AMV (SIGMA)
9. OMNISCRIPT (QIAGEN)
10. DISPLAY THERMO-RT (DISPLAY SYSTEMS BIOTECH)
11. POWERSCRIPT (CLONTECH)
12. – – – –
13. λ – HIND 111 MARKER

SEQUENCE LISTING

```
<160> NUMBER OF SEQ ID NOS: 13

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      Bacteriophage T7 Promoter oligonucleotide with a
      C9 3' Tail

<400> SEQUENCE: 1
ggccagtgaa ttgtaatacg actcactata gggatccccc cccc                 44

<210> SEQ ID NO 2
<211> LENGTH: 61
<212> TYPE: DNA
<213> ORGANISM: Artificial Sequence
<220> FEATURE:
<223> OTHER INFORMATION: Description of Artificial Sequence: Synthetic
      Bacteriophage T7 Promoter oligonucleotide with a
      T25 3' Tail

<400> SEQUENCE: 2
ggccagtgaa ttgtaatacg actcactata gggatctttt tttttttttt tttttttttt  60
t                                                                 61

<210> SEQ ID NO 3
<211> LENGTH: 61
<212> TYPE: DNA
<213> ORGANISM: Artificial Sequence
```

```
<220> FEATURE:
<223> OTHER INFORMATION: Description of Artificial Sequence: Synthetic
      Bacteriophage T3 Promoter oligonucleotide with a
      T25 3' Tail

<400> SEQUENCE: 3
ctcaacgcca cctaattacc ctcactaaag ggagattttt tttttttttt tttttttttt    60
t                                                                    61

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tttttttttt tttttttttt tttt                                           24

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(48)
<223> OTHER INFORMATION: a, c, t, g, unknown or other
<220> FEATURE:
<221> NAME/KEY: misc_feature
<222> LOCATION: (40)..(48)
<223> OTHER INFORMATION: This region may encompass 1-9 nucleotides

<400> SEQUENCE: 5
ggccagtgaa ttgtaatacg actcactata gggaggcggn nnnnnnn                  48

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tttttttttt tttttttttt ttttt                                          25

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaaaaaaaa aa                                                        12

<210> SEQ ID NO 8
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
ggggggggtt tttttt                                                          16

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gggggggggt tttttt                                                          17

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 aaaaaaccccc cc                                                             12

<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaaacccc ccc                                                             13

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttttttttt                                                                 10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaaaaaaaa                                                                 10
```

PROCESSES FOR DETECTING OR QUANTIFYING NUCLEIC ACIDS USING AN ARRAY OF FIXED OR IMMOBILIZED NUCLEIC ACIDS

CROSS REFERENCE TO RELATED APPLICATIONS

This application is a divisional of U.S. application Ser. No. 10/902,641 filed Jul. 29, 2004 (now U.S. Pat. No. 9,234,235) which is a divisional of U.S. application Ser. No. 09/896,897 filed Jun. 30, 2001, the contents of which are incorporated herein by reference.

SEQUENCE LISTING

The instant application contains a Sequence Listing which has been submitted electronically in ASCII format and is hereby incorporated by reference in its entirety. Said ASCII copy, created on Aug. 24, 2015, is named ENZ-60(D8)(D2)_SL.txt and is 4,002 bytes in size.

FIELD OF THE INVENTION

This invention relates to the field of analyte detection, quantification and amplification, including compositions and processes directed thereto.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

The quantification of RNA expression provides major insights into analysis of cellular metabolism, function, growth and interactions. Although individual RNA species have historically been the subject of these studies, more interest is currently being shown in analysis of the patterns of the simultaneous expression of multiple RNA species of both known and unknown function. This approach allows comparative studies on the patterns of expression between different populations of cells, thereby serving as an indicator of the differences in biochemical activities taking place within these populations. For instance, a single group of cells can be divided up into two or more populations where one group serves as a control and the other part is exposed to drugs, metabolites or different physical conditions. In this way, although the majority of the various species of mRNA show little or no differences in expression levels, certain mRNA species may show dramatic increased or decreased levels of expression compared to the untreated or normal control.

As an example, it has long been known that the application of a phorbol ester (PMA) results in changes in a large number of characteristics of mammalian cells growing in vitro. In an experiment reported by Lockhart et al., (1996, Nature Biotechnology 14; 1675-1680) cells growing in culture were exposed to PMA and at various times afterwards, mRNA was extracted and used to create a library of labeled probes. This material was subsequently hybridized to an array of nucleic acids that was complementary to various mRNA sequences. Significant changes could be seen in both the timing and the amount of induction of various cellular cytokines. On the other hand, so called "housekeeping" genes such as actin and GAPDH remained essentially unaffected by the treatment. This example demonstrates that the various mRNA's can be independently monitored to determine which particular genes may be affected by a treatment.

Natural differences between cell populations can also be examined. For instance, differences in the expression levels of various genes can be observed when cells progress through cell cycles (Cho et al., 1998 Mol Cell 2; 65-73 and Spellman et al., 1998 Mol. Biol. Cell 95; 14863-14868). The gene expression profiles that were generated by these studies validated this approach when significant differences in expression were observed for genes that had previously been characterized as encoding cell cycle related proteins. In addition, the arrays used in these studies comprised nucleic acid sequences that represented the entire genetic complement of the yeast being studied. As such, one of the results of these studies was the observation of a number of genes of previously unknown function that also displayed cell cycle dependent expression. Re-examination of these particular genes by other more conventional methods demonstrated that they were involved in cell cycle progression. Thus, this method was demonstrated as being capable of recognizing genes previously known for differential expression and also for identifying new genes.

The differences between normal and transformed cells have also been a subject of long standing interest. The nature of the particular genes that are either overexpressed or underexpressed relative to normal cells may provide information on the origination, progression or treatment of cancerous cells. Array analysis has been carried out by using RNA from tumor derived cells in comparison with expression from normal cells. In one study by Perou et al (1999 Proc. Nat Acad. Sci. USA 96; 9212-9217) human mammary epithelial cells (HMEC) were compared with specimens from primary breast tumors. Included in this study were responses to various cell factors as well as the results of confluence or senescence in the control cultures. All of these are factors that may be involved or affected by cellular transformation into the cancerous state. The amount of data generated in this type of study is almost overwhelming in its complexity. However distinct patterns or clusters of expression can be observed that are correlated to factors associated with the specimens. Further understanding will also be gained when data is gathered from expression in other tumor types and their untransformed equivalents.

There are two distinct elements in all of the expression studies that employ arrays. The first element is concerned with the preparation of the bank of probes that will be used to bind or capture labeled material that is derived from the mRNAs that are being analyzed. The purpose of these arrays is to provide a multiplicity of individual probes where each probe is located in a discrete spatially defined position. After hybridization of the sample is carried out, the particular amount of sample is measured for each site giving a relative measurement of how much material is present in the sample that has homology with the particular probe that is located at that site. The two most commonly used methods for array assembly operate on two very different scales for synthesis of arrays.

On the simplest level of construction, discrete nucleic acids are affixed to solid matrixes such as glass slides or nylon membranes in a process that is very similar to that employed by ink jet printers (For example, see Okamoto et al., 2000, Nature Biotechnology 18; 438-441). The nature of the probe deposited on the matrix can range from small synthetic oligonucleotides to large nucleic acid segments from clones. Preparation of a cloned segment to be used in this form of array assembly can range from *E. coli* colonies containing individual clones that are lysed and fixed directly onto a matrix or more elaborately by using individual plasmids as templates for preparation of PCR amplified material. The latter method is preferred due to the higher purity of the nucleic acid product. The choice of a particular probe to be used in the assembly can be directed in the sense that the function and sequence is known. This of course will always be true when oligonucleotides are used as the probes since they must be synthesized artificially. On the other hand, when the probes are derived from larger cloned segments of DNA, they can be used irrespective of knowledge of sequence or function. For instance, a bank of probes that represent the entire yeast genome was used in the studies cited earlier on differential expression during cell cycle progression. For human sequences, the burgeoning growth of the human sequencing project has provided a wealth of sequence information that is constantly expanding. Therefore, a popular source of probes that can be used to detect human transcripts has been Expressed Sequence Tags (ESTs) (Adams et al., 1991 Science 252; 1651-1656). The use of sequences of unknown function has the advantage of a lack of any a priori assumption concerning responsiveness in a comparative study and in fact, the study in itself may serve to identify functionality. At present, filter and glass arrays are commercially available from a number of sources for the analysis of expression from various human tissues, developmental stages and disease conditions. On the other hand, directions for making custom arrays are widely disseminated throughout the literature and over the Internet.

At the other end of the scale in complexity is a process where in situ synthesis of oligonucleotides is carried out directly on a solid matrix using a "masking" technology that is similar to that employed in etching of microcircuits (Pirrung et al., U.S. Pat. No. 5,143,854, hereby incorporated by reference). Since this process can be carried out on a very small microscale, a very large number of different probes can be loaded onto a single "biochip" as a high density array. However, since this method depends upon site-specific synthesis, only oligonucleotides are used and the probes are necessarily of limited size. Also, since directed sequence synthesis is used, sequence information has to be available for each probe. An advantage of this system is that instead of a single probe for a particular gene product, a number of probes from different segments can be synthesized and incorporated into the design of the array. This provides a redundancy of information, establishing that changes in levels of a particular transcript are due to fluctuations in the intended target rather than by transcripts with one or more similar sequences. These "biochips" are commercially available as well as the hardware and software required to read them.

Although solid supports such as plastic and glass have been commonly used for fixation of nucleic acids, porous materials have also been used. For example, oligonucleotides were joined to aldehyde groups in polyacrylamide (Yershov et al., (1996) Proc Nat. Acad. Sci USA 93; 4913-4918) and agarose (Afanassiev et al. (2000) Nucl. Acids Res. 28; e66) to synthesize arrays that were used in hybridization assays.

The second element involved in array analysis is the means by which the presence and amount of labeled nucleic acids bound to the various probes of the array will be detected. There are three levels of use of the target mRNA that can provide signal generation. In the first approach, the native RNA itself can be labeled. This has been carried out enzymatically by phosphorylation of fragmented RNA followed by T4 RNA ligase mediated addition of a biotinylated oligomer to the 5' ends (Lockhart et al, 1996). This method has the limitation that it entails an overnight incubation to insure adequate joining of labels to the RNA. For chemical labeling of RNA, the fragments can be labeled with psoralen that has been linked to biotin (Lockhart et al, 1996). This method has the disadvantage that the crosslinking that joins the label to the RNA can also lead to intrastrand crosslinking of target molecules reducing the amount of hybridizable material.

In the second approach, rather than labeling the transcript itself, the RNA is used as a template to synthesize cDNA copies by the use of either random primers or by oligo dT primers. Extension of the primers by reverse transcriptase can be carried out in the presence of modified nucleotides, thereby labeling all of the nascent cDNA copies. The modified nucleotides can have moieties attached that generate signals in themselves or they may have moieties suitable for attachment of other moieties capable of generation of signals. Examples of groups that have been used for direct signal generation have been radioactive compounds and fluorescent compounds such as fluorescein, Texas red, Cy3 and Cy 5. Direct signal generation has the advantage of simplicity but has the limitation that in many cases there is reduced efficiency for incorporation of the labeled nucleotides by a polymerase. Examples of groups that have been used for indirect signal generation in arrays are dinitrophenol (DNP) or biotin ligands. Their presence is detected later by the use of labeled molecules that have affinities for these ligands. Avidin or strepavidin specifically bind to biotin moieties and antibodies can be used that are specific for DNP or biotin. These proteins can be labeled themselves or serve as targets for secondary bindings with labeled compounds. Alternatively, when the labeled nucleotides contain chemically active substituents such as allylamine modifications, post-synthetic modification can be carried out by a chemical addition of a suitably labeled ester.

The synthesis of a cDNA copy from an mRNA template essentially results in a one to one molar ratio of labeled product compared to starting material. In some cases there may be limiting amounts of the mRNA being analyzed and for these cases, some amplification of the nucleic acid sequences in the sample may be desirable. This has led to the use of the third approach, where the cDNA copy derived from the original mRNA template is in itself used as a template for further synthesis. A system termed "Transcription Amplification System" (TAS) was described (Kwoh, D. Y. and Gingeras, T. R., 1989, Proc. Nat. Acad. Sci., 86, 1173-1177) in which a target specific oligonucleotide is used to generate a cDNA copy and a second target specific oligonucleotide is used to convert the single stranded DNA into double-stranded form. By inclusion of a T7 promoter sequence into the first oligonucleotide, the double-stranded molecule can be used to make multiple transcription products that are complementary to the original mRNA of interest. The purpose of this system was for amplification of a discrete sequence from a pool of various RNA species. No suggestion or appreciation of such a system for the use of non-discrete primer sequences for general amplification was described in this work.

Multiple RNA transcript copies homologous to the original RNA population has been disclosed by van Gelder et al. in U.S. Pat. No. 5,891,636 where specific reference is given to the utility of such a system for creating a library of various gene products in addition to discrete sequences. Since each individual mRNA molecule has the potential for ultimately being the source of a large number of complementary transcripts, this system enjoys the advantages of linear amplification such that smaller amounts of starting material are necessary compared to direct labeling of the original mRNA or its cDNA copy.

However, the work described in U.S. Pat. No. 5,891,636 specifically teaches away from addition of exogenous primers for synthesis of a 2$^{nd}$ strand. Instead, it discloses the use of oligonucleotide primers for production of only the first strand of cDNA. For synthesis of the second strand, two possible methods were disclosed. In the first method, the nicking activity of RNase H on the original mRNA template was used to create primers that could use the cDNA as a template. In the second method, DNA polymerase was added to form hairpins at the end of the first cDNA strand that could provide self-priming. The first method has a limitation that RNase H has to be added after the completion of the cDNA synthesis reaction and a balance of RNase H activity has to be determined to provide sufficient nicking without total degradation of potential RNA primers. The second method requires an extra step of incubation a different polymerase besides the Reverse Transcriptase and also S1 nuclease has to be added to eliminate the loop in the hairpin structure. In addition, the formation and extension by foldback is a poorly understood system that does not operate at high efficiency where sequences and amounts of cDNA copies may act as random factors.

In addition to the amplification provided by the use of RNA transcription, PCR has been included in some protocols to carry out synthesis of a library through the use of common primer binding sites at each end of individual sequences (Endege et al., 1999 Biotechniques 26; 542-550, Ying et al., 1999 Biotechniques 27; 410-414). These methods share the necessity for a machine dedicated to thermal cycling.

In addition to binding analytes from a library, the nucleic acids on an array can use the analytes as templates for primer extension reactions. For instance, determination of Single Nucleotide Polymorphisms, (SNP's) has been carried out by the use of a set of primers at different sites on the array that exhibit sequence variations from each other (Pastinen et al., 2000, Genome Research 10; 1031-1042). The ability or inability of a template to be used for primer extension by each set of primers is an indication of the particular sequence variations within the analytes. More complex series of reactions have also been carried out by the use of arrays as platforms for localized amplification as described in U.S. Pat. No. 5,641,658 and Weslin et al., 2000, Nature Biotechnology 18; 199-204. In these particular applications of array technology, PCR and SDA were carried out by providing a pair of unique primers for each individual nucleic acid target at each locus of the array. The presence or absence of amplification at each locus of the array served as an indicator of the presence or absence of the corresponding target sequences in the analyte samples.

Despite the accelerated development of the synthesis and use of DNA microarrays in recent years, the progress in the development of arrays of proteins or other ligands has been significantly slower even though such arrays are an ideal format with which to study gene expression, as well as antibody-antigen, receptor-ligand, protein-protein interactions and other applications. In previous art, protein arrays have been used for gene expression antibody screening, and enzymatic assays (Lueking et al. (1999) Anal. Biochem. 270; 103-111; de Wildt et al., (2000) Nature Biotechnology 18; 989-994, Arenkov et al., (2000) Analytical Biochemistry 278; 123-131). Protein arrays have also been used for high throughput ELISA assays (Mendoza et al., (1999) Biotechniques 27; 778-788) and for the detection of individual proteins in complex solutions (Haab, et al.; (2001) Genome Biology 2; 1-13). However, the use thus far has been limited because of the inherent problems associated with proteins. DNA is extremely robust and can be immobilized on a solid matrix, dried and rehydrated without any loss of activity or function. Proteins, however, are far more difficult to utilize in array formats. One of the main problems of using proteins in an array format is the difficulty of applying the protein to a solid matrix in a form that would allow the protein to be accessible and reactive without denaturing or otherwise altering the peptide or protein. Also, many proteins cannot be dehydrated and must be kept in solution at all times, creating further difficulties for use in arrays.

Some methods which have been used to prepare protein arrays include placing the proteins on a polyacrylamide gel matrix on a glass slide that has been activated by treatment with glutaraldehyde or other reagents (Arenkov, op. cit.). Another method has been the addition of proteins to aldehyde coated glass slides, followed by blocking of the remaining aldehyde sites with BSA after the attachment of the desired protein. This method, however, could not be used for small proteins because the BSA obscured the protein. Peptides and small proteins have been placed on slides by coating the slides with BSA and then activating the BSA with N,N'-disuccinimidyl carbonate (Taton et al., (2000) Science 2789, 1760-1763). The peptides were then printed onto the slides and the remaining activated sites were blocked with glycine, Protein arrays have also been prepared on poly-L-Lysine coated glass slides (Haab et al., op. cit.) and agarose coated glass slides (Afanassiev et al., (2000) Nucleic Acids Research 28, e66). "Protein Chips" are also commercially available from Ciphergen (Fremont, Calif.) for a process where proteins are captured onto solid surfaces and analyzed by mass spectroscopy.

The use of oligonucleotides as 'hooks' or 'tags' as identifiers for non-nucleic acid molecules has been described in the literature. For instance, a library of peptides has been made where each peptide is attached to a discrete nucleic acid portion and members of the library are tested for their ability to bind to a particular analyte. After isolation of the peptides that have binding affinities, identification was carried out by PCR to "decode" the peptide sequence (Brenner and Lerner, (1992) Proc. Nat. Acad. Sci. USA 89; 5381-5383, Needels et al., (1993) Proc. Nat. Acad. Sci. USA 90; 10,700-10,704). Nucleic acid sequences have also been used as tags in arrays where selected oligonucleotide sequences were added to primers used for single nucleotide polymorphism genotyping (Hirschhorn, et al., (2000) Proc. Natl. Acad. Sc. USA, 97; 12164-12169). However, in this case the 'tag' is actually part of the primer design and it is used specifically for SNP detection using a single base extension assay. A patent application filed by Lohse, et al., (WO 00/32823) has disclosed the use of DNA-protein fusions for protein arrays. In this method, the protein is synthesized from RNA transcripts which are then reverse transcribed to give the DNA sequences attached to the corresponding protein. This system lacks flexibility since the technology specifically relates only to chimeric molecules that comprise a nucleic acid and a peptide or protein. In addition, the protein is directly derived from the RNA sequence so that the resultant DNA sequence is also dictated by the protein sequence. Lastly, every protein that is to be used in an array requires the use of an in vitro translation system made from cell extracts, a costly and inefficient system for large scale synthesis of multiple probes. The use of electrochemically addressed chips for use with chimeric compositions has also been described by Bazin and Livache 1999 in "Innovation and Perspectives in solid Phase Synthesis & Recombinatorial Libraries" R. Epton (Ed.) Mayflower Scientific Limited, Birmingham, UK.

SUMMARY OF THE INVENTION

This invention provides a composition of matter that comprises a library of analytes, the analytes being hybridized to an array of nucleic acids, the nucleic acids being fixed or immobilized to a solid support, wherein the analytes comprise an inherent universal detection target (UDT), and a universal detection element (UDE) attached to the UDT, wherein the UDE generates a signal indicating the presence or quantity of the analytes, or the attachment of UDE to UDT.

This invention also provides a composition of matter that comprises a library of analytes, such analytes being hybridized to an array of nucleic acids, and such nucleic acids being fixed or immobilized to a solid support, wherein the analytes comprise a non-inherent universal detection target (UDT) and a universal detection element (UDE) hybridized to the UDT, and wherein the UDE generates a signal directly or indirectly to detect the presence or quantity of such analytes.

The present invention further provides a composition of matter that comprises a library of analytes, such analytes being hybridized to an array of nucleic acids, and such nucleic acids being fixed or immobilized to a solid support, wherein the hybridization between the analytes and the nucleic acids generate a domain for complex formation, and the composition further comprises a signaling entity complexed to the domain.

The present invention yet further provides a process for detecting or quantifying more than one nucleic acid of interest in a library comprising the steps of: a) providing: (i) an array of fixed or immobilized nucleic acids complementary to the nucleic acids of interest; (ii) a library of nucleic acid analytes which may contain the nucleic acids of interest sought to be detected or quantified, wherein each of the nucleic acids of interest comprise at least one inherent universal detection target (UDT); and (iii) universal detection elements (UDE) which generates a signal directly or indirectly; b) hybridizing the library (ii) with the array of nucleic acids (i) to form hybrids if the nucleic acids of interest are present; c) contacting the UDEs with the UDTs to form a complex bound to the array; d) detecting or quantifying the more than one nucleic acid of interest by detecting or measuring the amount of signal generated from UDEs bound to the array.

Also provided by this invention is a process for detecting or quantifying more than one nucleic acid of interest in a library comprising the steps of a) providing: (i) an array of fixed or immobilized nucleic acids complementary to the nucleic acids of interest; (ii) a library of nucleic acid analytes which may contain the nucleic acids of interest sought to be detected or quantified, wherein each of the nucleic acids of interest comprise at least one inherent universal detection target (UDT); and (iii) universal detection elements (UDE) which generates a signal directly or indirectly; b) contacting the UDEs with the UDTs in the library of nucleic acid analytes to form one or more complexes; c) hybridizing the library of nucleic acid analytes with the array of nucleic acids (i) to form hybrids if such nucleic acids of interest are present; d) detecting or quantifying the more than one nucleic acid of interest by detecting or measuring the amount of signal generated from UDEs bound to the array.

Also provided herein is a process for detecting or quantifying more than one nucleic acid of interest in a library comprising the steps of a) providing (i) an array of fixed or immobilized nucleic acids complementary to the nucleic acids of interest; (ii) a library of nucleic acid analytes which may contain the nucleic acids of interest sought to be detected or quantified, wherein each of the nucleic acids of interest comprise at least one non-inherent universal detection target (UDT), wherein the non-inherent UDT is attached to the nucleic acid analytes; and (iii) universal detection elements (UDE) which generate a signal directly or indirectly; b) hybridizing the library (ii) with the array of nucleic acids (i) to form hybrids if the nucleic acids of interest are present; c) contacting the UDEs with the UDTs to form a complex bound to the array; d) detecting or quantifying the more than one nucleic acid of interest by detecting or measuring the amount of signal generated from UDEs bound to the array.

Another aspect provided by this invention is a process for detecting or quantifying more than one nucleic acid of interest in a library comprising the steps of a) providing (i) an array of fixed or immobilized nucleic acids complementary to the nucleic acids of interest; (ii) a library of nucleic acid analytes which may contain the nucleic acids of interest sought to be detected or quantified, wherein each of such nucleic acids of interest comprise at least one non-inherent universal detection target (UDT), wherein the non-inherent UDTs are attached to the nucleic acid analytes; and (iii) universal detection elements (UDE) which generate a signal directly or indirectly; b) contacting the UDEs with the UDTs in the library of nucleic acid analytes to form one or more complexes; c) hybridizing the library (ii) with the array of nucleic acids (i) to form hybrids if such nucleic acids of interest are present; d) detecting or quantifying the more than one nucleic acid of interest by detecting or measuring the amount of signal generated from UDEs bound to the array.

Another aspect provided by this invention is a process for detecting or quantifying more than one nucleic acid of interest in a library comprising the steps of a) providing (i) an array of fixed or immobilized nucleic acids complementary to the nucleic acids of interest; (ii) a library of nucleic acid analytes which may contain the nucleic acids of interest sought to be detected or quantified; (iii) means for attaching one or more universal detection targets (UDT) to a nucleic acid; (iv) universal detection elements (UDE) which generates a signal directly or indirectly; b) attaching such UDTs (iii) to the library of nucleic acid analytes (ii); c) hybridizing the library (ii) with the array of nucleic acids (i) to form hybrids if such nucleic acids of interest are present; d) contacting the UDEs with the UDTs to form a complex bound to the array; e) detecting or quantifying the more than one nucleic acid of interest by detecting or measuring the amount of signal generated from UDEs bound to the array.

Still another feature is process for detecting or quantifying more than one nucleic acid of interest in a library comprising the steps of a) providing (i) an array of fixed or immobilized nucleic acids complementary to the nucleic acids of interest; (ii) a library of nucleic acid analytes which may contain the nucleic acids of interest sought to be detected or quantified; (iii) means for attaching one or more universal detection targets (UDT) to a nucleic acid; (iv) universal detection elements (UDE) which generate a signal directly or indirectly; b) attaching the UDTs (iii) to the library of nucleic acid analytes (ii); c) contacting the UDEs with the UDTs in the library of nucleic acid analytes to form one or more complexes; d) hybridizing the library (ii) with the array of nucleic acids (i) to form hybrids if such nucleic acids of interest are present; e) detecting or quantifying the more than one nucleic acid of interest by detecting or measuring the amount of signal generated from UDEs bound to the array.

The present invention provides additionally a process for detecting or quantifying more than one nucleic acid of interest in a library comprising the steps of a) providing (i) an array of fixed or immobilized nucleic acids complementary to the nucleic acids of interest; (ii) a library of nucleic acid analytes which may contain the nucleic acids of interest sought to be detected or quantified; and (iii) universal detection elements (UDEs) which bind to a domain formed by nucleic acid hybrids for complex formation and generate a signal directly or indirectly; b) hybridizing the library (ii) with the array of nucleic acids (i) to form hybrids if such nucleic acids of interest are present, wherein any formed hybrids generate a domain for complex formation; c) contacting the UDEs with any hybrids to form a complex bound to the array; d) detecting or quantifying the more than one nucleic acid of interest by detecting or measuring the amount of signal generated from UDEs bound to the array.

Also provided herein is a composition of matter comprising a library of first nucleic acid analyte copies, such first nucleic acid copies being hybridized to an array of nucleic acids, those nucleic acids being fixed or immobilized to a solid support, wherein such first nucleic acid copies comprise an inherent universal detection target (UDT) and a universal detection element (UDE) attached to the UDT, wherein the UDE generates a signal directly or indirectly to detect the presence or quantity of any analytes.

Another embodiment of this invention is a composition of matter comprising a library of first nucleic acid analyte copies, such first nucleic acid copies being hybridized to an array of nucleic acids, the nucleic acids being fixed or immobilized to a solid support, wherein such first nucleic acid copies comprise one or more non-inherent universal detection targets (UDTs) and one or more universal detection elements (UDEs) attached to the UDTs, wherein the UDEs generate a signal directly or indirectly to detect the presence or quantity of any analytes, and wherein the UDTs are either: (i) at the 5' ends of the first nucleic acid copies and not adjacent to an oligoT segment or sequence, or (ii) at the 3' ends of the first nucleic acid copies, or (iii) both (i) and (ii).

This invention also concerns a process for detecting or quantifying more than one nucleic acid of interest in a library comprising the steps of a) providing (i) an array of fixed or immobilized nucleic acids identical in part or whole to the nucleic acids of interest; (ii) a library of nucleic acid analytes which may contain the nucleic acids of interest sought to be detected or quantified, wherein each of such nucleic acids of interest comprise at least one inherent universal detection target (UDT); (iii) universal detection elements (UDE) which generate a signal directly or indirectly; and (iv) polymerizing means for synthesizing nucleic acid copies of the nucleic acids of analytes; b) synthesizing one or more first nucleic acid copies which are complementary to all or part of the nucleic acid analytes and synthesizing sequences which are complementary to all or part of the UDT to form a complementary UDT; c) hybridizing such first nucleic acid copies with the array of nucleic acids (i) to form hybrids if such nucleic acids of interest are present; d) contacting the UDEs with the complementary UDTs of the first nucleic acid copies to form a complex bound to the array; e) detecting or quantifying the more than one nucleic acid of interest by detecting or measuring the amount of signal generated from UDEs bound to the array.

Another embodiment provided by this invention is a process for detecting or quantifying more than one nucleic acid of interest in a library comprising the steps of a) providing (i) an array of fixed or immobilized nucleic acids identical in part or whole to the nucleic acids of interest; (ii) a library of nucleic acid analytes which may contain the nucleic acids of interest sought to be detected or quantified, wherein each of such nucleic acids of interest comprise at least one inherent universal detection target (UDT); (iii) universal detection elements (UDE) which generate a signal directly or indirectly; and (iv) polymerizing means for synthesizing nucleic acid copies of such nucleic acid analytes; b) synthesizing one or more first nucleic acid copies of such nucleic acid analytes; c) contacting the UDEs with the UDTs in the first nucleic acid copies to form one or more complexes; d) hybridizing such first nucleic acid copies with the array of nucleic acids (i) to form hybrids if such nucleic acids of interest are present; and e) detecting or quantifying the more than one nucleic acid of interest by detecting or measuring the amount of signal generated from UDEs bound to the array.

An additional aspect of the present invention is a process for detecting or quantifying more than one nucleic acid of interest in a library comprising the steps of a) providing (i) an array of fixed or immobilized nucleic acids identical in part or whole to the nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) attaching the non-inherent UDTs to either the 3' ends of the nucleic acid analytes, the 5' ends of the first nucleic acid analytes, or both the 3' ends and the 5' ends of the nucleic acid analytes; c) synthesizing one or more first nucleic acid copies of the nucleic acid analytes; d) hybridizing the first nucleic acid copies with the array of nucleic acids (i) to form hybrids if such nucleic acids of interest are present; e) contacting the UDEs with the UDTs of the first nucleic acid copies to form a complex bound to the array; f) detecting or quantifying the more than one nucleic acid of interest by detecting or measuring the amount of signal generated from UDEs bound to the array.

Also provided herein is a process for detecting or quantifying more than one nucleic acid of interest in a library comprising the steps of a) providing (i) an array of fixed or immobilized nucleic acids identical in part or whole to the nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) attaching such non-inherent UDTs to either the 3' ends of the nucleic acid analytes, the 5' ends of the first nucleic acid analytes, or both the 3' ends and the 5' ends of the nucleic acid analytes; c) synthesizing one or more first nucleic acid copies of the nucleic acid analytes; d) contacting the UDEs with the UDTs of the first nucleic acid copies to form complexes; e) hybridizing the first nucleic acid copies with the array of nucleic acids (i) to form hybrids if any nucleic acids of interest are present; f) detecting or quantifying the more than one nucleic acid of interest by detecting or measuring the amount of signal generated from UDEs bound to the array.

Another embodiment provided herein is a process for detecting or quantifying more than one nucleic acid of interest in a library comprising the steps of a) providing (i) an array of fixed or immobilized nucleic acids identical in part or whole to such nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) synthesizing one or more first nucleic acid copies of the nucleic acid analytes; c) attaching the non-inherent UDTs to either the 3' ends of the first nucleic acid copies, the 5' ends of the first nucleic acid copies, or both the 3' ends and the 5' ends of the first nucleic acid copies; d) hybridizing the first nucleic acid copies with the array of nucleic acids (i) to form hybrids if any nucleic acids of interest are present; e) contacting the UDEs with the UDTs of the first nucleic acid copies to form a complex bound to the array; and f) detecting or quantifying the more than one nucleic acid of interest by detecting or measuring the amount of signal generated from UDEs bound to the array.

Another process provided by this invention is for detecting or quantifying more than one nucleic acid of interest in a library comprising the steps of a) providing (i) an array of fixed or immobilized nucleic acids identical in part or whole to the nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) synthesizing one or more first nucleic acid copies of the nucleic acid analytes; c) attaching the non-inherent UDTs to either the 3' ends of the first nucleic acid copies, the 5' ends of the first nucleic acid copies, or both the 3' ends and the 5' ends of the first nucleic acid copies; d) contacting the UDEs with the UDTs of the first nucleic acid copies to form a complex; e) hybridizing the first nucleic acid copies with the array of nucleic acids (i) to form hybrids if any nucleic acids of interest are present; and f) detecting or quantifying the more than one nucleic acid of interest by detecting or measuring the amount of signal generated from UDEs bound to the array.

Yet further provided is a process for detecting or quantifying more than one nucleic acid of interest in a library comprising the steps of a) providing (i) an array of fixed or immobilized nucleic acids complementary to the nucleic acids of interest; (ii) a library of nucleic acid analytes which may contain the nucleic acids of interest sought to be detected or quantified; (iii) universal detection elements (UDEs) which bind to a domain for complex formation formed by nucleic acid hybrids and generate a signal directly or indirectly; and (iv) polymerizing means for synthesizing nucleic acid copies of the nucleic acid analytes; b) synthesizing one or more nucleic acid copies of the nucleic acid analytes; c) hybridizing the first nucleic acid copies with the array of nucleic acids (i) to form hybrids if any nucleic acids of interest are present, wherein any formed hybrids generate a domain for complex formation; d) contacting the UDEs with the hybrids to form a complex bound to the array; and e) detecting or quantifying the more than one nucleic acid of interest by detecting or measuring the amount of signal generated from UDEs bound to the array.

Another aspect provided by this invention is a composition of matter comprising a library of double-stranded nucleic acids substantially incapable of in vivo replication and free of non-inherent homopolymeric sequences, the nucleic acids comprising sequences complementary or identical in part or whole to inherent sequences of a library obtained from a sample, wherein the double-stranded nucleic acids comprise at least one inherent universal detection target (UDT) proximate to one end of the double strand and at least one non-inherent production center proximate to the other end of the double strand.

Yet another aspect of this invention concerns a composition of matter comprising a library of double-stranded nucleic acids substantially incapable of in vivo replication, such nucleic acids comprising sequences complementary or identical in part or whole to inherent sequences of a library obtained from a sample, wherein the double-stranded nucleic acids comprise at least four (4) non-inherent nucleotides proximate to one end of the double strand and a non-inherent production center proximate to the other end of the double strand.

Among other useful aspects of this invention is a composition of matter comprising a library of double-stranded nucleic acids fixed to a solid support, those nucleic acids comprising sequences complementary or identical in part or whole to inherent sequences of a library obtained from a sample and the nucleic acids further comprising at least one first sequence segment of non-inherent nucleotides proximate to one end of the double strand and at least one second sequence segment proximate to the other end of the double strand, the second sequence segment comprising at least one production center.

Another feature of this invention is a composition of matter comprising a library of double-stranded nucleic acids attached to a solid support, the nucleic acids comprising sequences complementary or identical in part or whole to inherent sequences of a library obtained from a sample, wherein the double-stranded nucleic acids comprise at least one inherent universal detection target (UDT) proximate to one end of the double strand and at least one non-inherent production center proximate to the other end of the double strand.

The invention herein also provides a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, the polymerizing means comprising a first set of primers and a second set of primers, wherein the second set of primers comprises at least two segments, the first segment at the 3' end comprising random sequences, and the second segment comprising at least one production center; (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) contacting the extended first copies with the second set of primers to form more than one second bound entity; e)

extending the bound second set of primers by means of template sequences provided by the extended first copies to form more than one complex comprising extended first copies and extended second set of primers; f) synthesizing from a production center in the second set of primers in the complexes one or more nucleic acid copies under isothermal or isostatic conditions; g) hybridizing any nucleic acid copies formed in step f) to the array of nucleic acids provided in step a) (i); and h) detecting or quantifying any of the hybridized copies obtained in step g).

Also provided by this invention is a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers comprise at least one production center; and (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) extending the first copies by means of at least four (4) or more non-inherent homopolymeric nucleotides; e) contacting the extended first copies with the second set of primers to form more than one second bound entity; f) extending the bound second set of primers by means of template sequences provided by the extended first copies to form more than one complex comprising extended first copies and extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h).

Another feature of this invention is a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h).

Still yet further this invention provides a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the second set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h).

Still yet further provided by this invention is a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers, a second set of primers and a third set of primers wherein the third set comprises at least one production center; and b) contacting the library of nucleic acid analytes with the first set of primers to form a first set of bound primers; c) extending the first set of bound primers by means of template sequences provided by the nucleic acid analytes to form first copies of the analytes; d) contacting the extended first copies with the second set of primers to form a second set of bound primers; e) extending the second set of bound primers by means of template sequences provided by the extended first copies to form second copies of the nucleic acid analytes; f) contacting the second copies with the third set of primers to form more than one third bound entity to form a third set of bound primers; g) extending the third set of bound primers by means of template sequences provided by the extended second set of primers to form a hybrid comprising a second copy, a third copy and at least one production center; h) synthesizing from the production center in the second set of primers in the complexes one or more nucleic acid copies under isothermal or isostatic conditions; i) hybridizing the nucleic acid copies formed in step i) to the array of nucleic acids provided in step a) (i); and j) detecting or quantifying any of the hybridized copies obtained in step i).

Also uniquely provided in this invention is a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers and a second set of primers, wherein the first set of primers are fixed or immobilized to a solid support, and wherein the second set of primers comprises at least two segments, the first segment at the 3' end comprising random sequences, and the second segment comprising at least one production center; (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) contacting the extended first copies with the second set of primers to form more than one second bound entity; e) extending the bound second set of primers by means of template sequences provided by the extended first copies to form more than one complex comprising extended first copies and extended second set of primers; f) synthesizing from a production center in the second set of primers in the complexes one or more nucleic acid copies under isothermal or isostatic conditions; g) hybridizing the nucleic acid copies formed in step f) to the array of nucleic acids provided in step a) (i); and h) detecting or quantifying any of the hybridized copies obtained in step g).

Another significant aspect of this invention is a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers are fixed or immobilized to a solid support, and wherein the first set of primers comprise at least one production center; and (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) extending the first copies by means of at least four (4) or more non-inherent homopolymeric nucleotides; e) contacting the extended first copies with the second set of primers to form more than one second bound entity; f) extending the bound second set of primers by means of template sequences provided by the extended first copies to form more than one complex comprising extended first copies and extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h).

Also provided in accordance with the present invention is a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers are fixed or immobilized to a solid support, and wherein the first set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h).

Another feature of the present invention concerns a process for detecting or quantifying more than one nucleic acid of interest in a library comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers are fixed or immobilized to a solid support, and wherein the second set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h).

Yet another process is provided by this invention, the process being one for detecting or quantifying more than one nucleic acid of interest in a library and comprising the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers, a second set of primers and a third set of primers, wherein the first set of primers are fixed or immobilized to a solid support, and wherein the third set comprises at least one production center; and b) contacting the library of nucleic acid analytes with the first set of primers to form more than one first bound entity; c) extending the bound first set of primers by means of template sequences provided by the nucleic acid analytes to form first copies of the analytes; d) contacting the extended first copies with the second set of primers to form more than one second bound entity; e) extending the bound second set of primers by means of template sequences provided by the extended first copies to form an extended second set of primers; f) separating the extended second set of primers obtained in step e); g) contacting the extended second set of primers with the third set of primers to form more than one third bound entity; h) extending the third bound entity by means of template sequences provided by the extended second set of primers to form more than one complex comprising the extended third bound entity and the extended set of primers; i) synthesizing from a production center in the second set of primers in the complexes one or more nucleic acid copies under isothermal or isostatic conditions; j) hybridizing the nucleic acid copies formed in step i) to the array of nucleic acids provided in step a) (i); and k) detecting or quantifying any of the hybridized copies obtained in step j).

Another significant embodiment provided herein is a process for detecting or quantifying more than one nucleic acid of interest in a library comprising the steps of a) providing (i) an array of fixed or immobilized nucleic acids identical in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers; b) contacting the nucleic acid analytes with the first set of primers to form a first bound entity; c) extending the bound set of first set of primers by means of template sequences provided by the nucleic acid analytes to form first nucleic acid copies of the analytes; d) separating the first nucleic acid copies from the analytes; e) repeating steps b), c) and d) until a desirable amount of first nucleic acid copies have been synthesized; f) hybridizing the nucleic acid copies formed in step e) to the array of nucleic acids provided in step (i); and g) detecting or quantifying any of the hybridized first nucleic acid copies obtained in step f).

The invention described herein also provides a process for detecting or quantifying more than one nucleic acid of interest in a library comprising the steps of a) providing (i) an array of fixed or immobilized nucleic acids identical in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers; (iv) means for addition of sequences to the 3' end of nucleic acids; b) contacting the nucleic acid analytes with the first set of primer to form a first bound entity; c) extending the bound set of first set of primers by means of template sequences provided by the nucleic acid analytes to form first nucleic acid copies of the analytes; d) extending the first nucleic copies by the addition of non-template derived sequences to the 3' end of the first nucleic acid copies; e) contacting the extended first nucleic acid copies with the second set of primers to form a second bound entity; f) extending the bound set of second set of primers by means of template sequences provided by the extended first nucleic acid copies to form second nucleic acid copies; g) separating the second nucleic acid copies from the extended first nucleic acid copies; h) repeating steps e), f) and g) until a desirable amount of second nucleic acid copies have been synthesized; i) hybridizing the second nucleic acid copies formed in step h) to the array of nucleic acids provided in step (i); and j) detecting or quantifying any of the hybridized second nucleic acid copies obtained in step i).

Among other significant compositions provided by the present invention is a composition of matter that comprises an array of solid surfaces comprising discrete areas, wherein at least two of the discrete areas each comprises a first set of nucleic acid primers; and a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ from each other by at least one base; and wherein the nucleotide sequences of the second set of nucleic acid primers of a first discrete area and the nucleotide sequences of the second set of nucleic acid primers of a second discrete area are substantially the same or identical.

A related composition of this invention concerns a composition of matter that comprises an array of solid surfaces comprising a plurality of discrete areas; wherein at least two of the discrete areas each comprises a first set of nucleic acid primers; and a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ substantially from each other; and wherein the nucleotide sequences of the second set of nucleic acid primers of a first discrete area and the nucleotide sequences of the second set of nucleic acid primers of a second discrete area are substantially the same or identical.

Related to the last-mentioned compositions are processes for producing two or more copies of nucleic acids of interest in a library comprising the steps of a) providing (i) an array of solid surfaces comprising a plurality of discrete areas; wherein at least two of the discrete areas each comprises: (1) a first set of nucleic acid primers; and (2) a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ from each other by at least one base; and wherein the nucleotide sequences of the second set of nucleic acid primers of a first discrete area and the nucleotide sequences of the second set of nucleic acid primers of a second discrete area are substantially the same or identical; (ii) a library of nucleic acid analytes which may contain the nucleic acids of interest; (iii) polymerizing means for synthesizing nucleic acid copies of the nucleic acids of interest; b) contacting a primer of the first set with a complementary sequence in the nucleic acid of interest; c) extending the primer in the first set using the nucleic acid of interest as a template to generate an extended first primer; d) contacting a primer in the second set with a complementary sequence in the extended first primer; e) extending the primer in the second set using the extended first primer as a template to generate an extended second primer; f) contacting a primer in the first set with a complementary sequence in the extended second primer; g) extending the primer in the first set using the extended second primer as a template to generate an extended first primer; and h) repeating steps d) through g) above one or more times.

Another related process of the present invention is useful for detecting or quantifying more than one nucleic acid of interest in a library comprising the steps of a) providing (i) an array of solid surfaces comprising a plurality of discrete areas; wherein at least two of such discrete areas each comprises: (1) a first set of nucleic acid primers; and (2) a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ from each other by at least one base; and wherein the nucleotide sequences of the second set of nucleic acid primers of a first discrete area and the nucleotide sequences of the second set of nucleic acid primers of a second discrete area are substantially the same or identical; (ii) a library of nucleic acid analytes which may contain the nucleic acids of interest; (iii) polymerizing means for synthesizing nucleic acid copies of the nucleic acids of interest; and (iv) non-radioactive signal generating means capable of being attached to or incorporated into nucleic acids; b) contacting a primer of the first set with a complementary sequence in the nucleic acid of interest; c) extending the primer in the first set using the nucleic acid of interest as a template to generate an extended first primer; d) contacting a primer in the second set with a complementary sequence in the extended first primer; e) extending the primer in the second set using the extended first primer as a template to generate an extended second primer; f) contacting a primer in the first set with a complementary sequence in the extended second primer; g) extending the primer in the first set using the extended second primer as a template to generate an extended first primer; h) repeating steps d) through g) above one or more times; and i) detecting or quantifying by means of the non-radioactive signal generating means attached to or incorporated into any of the extended primers in steps c), e), g), and h).

Another useful composition provided by the present invention is a composition of matter that comprises an array of solid surfaces comprising a plurality of discrete areas, wherein at least two of such discrete areas comprise: a chimeric composition comprising a nucleic acid portion; and a non-nucleic acid portion, wherein the nucleic acid portion of a first discrete area has the same sequence as the nucleic acid portion of a second discrete area, and wherein the non-nucleic acid portion has a binding affinity for analytes of interest.

Further provided by the present invention is a composition of matter that comprises an array of solid surfaces comprising a plurality of discrete areas; wherein at least two of the discrete areas comprise a chimeric composition hybridized to complementary sequences of nucleic acids fixed or immobilized to the discrete areas, wherein the chimeric composition comprises a nucleic acid portion, and a non-nucleic acid portion, the nucleic acid portion comprising at least one sequence, wherein the non-nucleic acid portion has a binding affinity for analytes of interest, and wherein when the non-nucleic acid portion is a peptide or protein, the nucleic acid portion does not comprises sequences which are either identical or complementary to sequences that code for such peptide or protein.

Also provided as a significant aspect of the present invention is a process for detecting or quantifying analytes of interest, the process comprising the steps of 1) providing a) an array of solid surfaces comprising a plurality of discrete areas, wherein at least two of such discrete areas comprise a chimeric composition comprising a nucleic acid portion, and a non-nucleic acid portion; wherein the nucleic acid portion of a first discrete area has the same sequence as the nucleic acid portion of a second discrete area; and wherein the non-nucleic acid portion has a binding affinity for analytes of interest; b) a sample containing or suspected of containing one or more of the analytes of interest; and c) signal generating means; 2) contacting the array a) with the sample b) under conditions permissive of binding the analytes to the non-nucleic acid portion; 3) contacting the bound analytes with the signal generating means; and 4) detecting or quantifying the presence of the analytes.

Another feature provided by the present invention is a process for detecting or quantifying analytes of interest, this process comprising the steps of 1) providing a) an array of solid surfaces comprising a plurality of discrete areas; wherein at least two of such discrete areas comprise a chimeric composition comprising a nucleic acid portion; and a non-nucleic acid portion; wherein the nucleic acid portion of a first discrete area has the same sequence as the nucleic acid portion of a second discrete area; and wherein the non-nucleic acid portion has a binding affinity for analytes of interest; b) a sample containing or suspected of containing one or more of the analytes of interest; and c) signal generating means; 2) labeling the analytes of interest with the signal generating means; 3) contacting the array a) with the labeled analytes under conditions permissive of binding the labeled analytes to the non-nucleic acid portion; and 4) detecting or quantifying the presence of the analytes.

Also provided by the present invention is a process for detecting or quantifying analytes of interest, the process comprising the steps of 1) providing a) an array of solid surfaces comprising a plurality of discrete areas; wherein at least two of such discrete areas comprise nucleic acids fixed or immobilized to such discrete areas, b) chimeric compositions comprising: i) a nucleic acid portion; and ii) a non-nucleic acid portion; the nucleic acid portion comprising at least one sequence, wherein the non-nucleic acid portion has a binding affinity for analytes of interest, and wherein when the non-nucleic acid portion is a peptide or protein, the nucleic acid portion does not comprise sequences which are either identical or complementary to sequences that code for the peptide or protein; c) a sample containing or suspected of containing the analytes of interest; and d) signal generating means; 2) contacting the array with the chimeric compositions to hybridize the nucleic acid portions of the chimeric compositions to complementary nucleic acids fixed or immobilized to the array; 3) contacting the array a) with the sample b) under conditions permissive of binding the analytes to the non-nucleic acid portion; 4) contacting the bound analytes with the signal generating means; and 5) detecting or quantifying the presence of the analytes.

Additionally this invention provides a process for detecting or quantifying analytes of interest, the process comprising the steps of 1) providing a) an array of solid surfaces comprising a plurality of discrete areas; wherein at least two of the discrete areas comprise nucleic acids fixed or immobilized to the discrete areas, b) chimeric compositions comprising i) a nucleic acid portion; and ii) a non-nucleic acid portion, the nucleic acid portion comprising at least one sequence, wherein the non-nucleic acid portion has a binding affinity for analytes of interest, and wherein when the non-nucleic acid portion is a peptide or protein, the nucleic acid portion does not comprise sequences which are either identical or complementary to sequences that code for the peptide or protein; c) a sample containing or suspected of containing the analytes of interest; and d) signal generating means; 2) contacting the chimeric compositions with the sample b) under conditions permissive of binding the analytes to the non-nucleic acid portion; 3) contacting the array with the chimeric compositions to hybridize the nucleic acid portions of the chimeric compositions to complementary nucleic acids fixed or immobilized to the array; 4) contacting the bound analytes with the signal generating means; and 5) detecting or quantifying the presence of the analytes.

Another useful provision of the invention herein is a process for detecting or quantifying analytes of interest, such process comprising the steps of 1) providing a) an array of solid surfaces comprising a plurality of discrete areas; wherein at least two of the discrete areas comprise nucleic acids fixed or immobilized to the discrete areas, b) chimeric compositions comprising i) a nucleic acid portion; and ii) a non-nucleic acid portion; the nucleic acid portion comprising at least one sequence, wherein the non-nucleic acid portion has a binding affinity for analytes of interest, and wherein when the non-nucleic acid portion is a peptide or protein, the nucleic acid portion does not comprise sequences which are either identical or complementary to sequences that code for the peptide or protein; c) a sample containing or suspected of containing the analytes of interest; and d) signal generating means; 2) contacting the array with the chimeric compositions to hybridize the nucleic acid portions of the chimeric compositions to complementary nucleic acids fixed or immobilized to the array; 3) labeling the analytes of interest with the signal generating means; 4) contacting the array with the labeled analytes to bind the analytes to the non-nucleic acid portion; and 5) detecting or quantifying the presence of the analytes.

Yet further provided by the present invention is a process for detecting or quantifying analytes of interest, the process comprising the steps of 1) providing a) an array of solid surfaces comprising a plurality of discrete areas; wherein at least two of the discrete areas comprise nucleic acids fixed or immobilized to the discrete areas, b) chimeric compositions comprising: i) a nucleic acid portion; and ii) a non-nucleic acid portion; the nucleic acid portion comprising at least one sequence, wherein the non-nucleic acid portion has a binding affinity for analytes of interest, and wherein when the non-nucleic acid portion is a peptide or protein, such nucleic acid portion does not comprise sequences which are either identical or complementary to sequences that code for the peptide or protein; c) a sample containing or suspected of containing the analytes of interest; and d) signal generating means; 2) contacting the array with the chimeric compositions to hybridize the nucleic acid portions of the chimeric compositions to complementary nucleic acids fixed or immobilized to the array; 3) labeling the analytes of interest with the signal generating means; 4) contacting the array with the labeled analytes to bind the analytes to the non-nucleic acid portion; and 5) detecting or quantifying the presence of the analytes.

BRIEF DESCRIPTION OF THE FIGURES

FIG. 1 shows an array with mRNA from a library of analytes with UDTs.

FIG. 2 shows fragmentation of analytes followed by addition of non-inherent UDTs to analytes.

FIG. 3 depicts the incorporation of a non-inherent UDT to a 1st cNA copy by means of a primer.

FIG. 4 illustrates the use of Random Primers with Production Centers for $2^{nd}$ strand synthesis.

FIG. 5 relates to the same process as FIG. 4 wherein the Production Centers are double-stranded.

FIG. 6 illustrates 2nd cNA strand priming at terminal and internal sites.

FIG. 7 illustrates 2nd cNA strand priming after Terminal transferase addition of homopolymeric sequences.

FIG. 8 shows the addition of primer binding sites by ligation.

FIG. 9 illustrates multiple additions of primer binding sites.

FIG. 10 shows 1st strand synthesis by extension of an oligo dT primer bound to a bead followed by 2nd cNA strand synthesis with random primers having production centers. FIG. 10 discloses "AAAAAAAAAAAA" as SEQ ID NO: 7.

FIG. 11 illustrates 1st strand synthesis from poly T primer indirectly bound to a bead followed by 2nd strand synthesis with random primers having production center. FIG. 11 discloses SEQ ID NOS 7, 8, 7-10, 9, 11 and 11, respectively, in order of appearance.

FIG. 12 shows the incorporation of a promoter during 3rd strand synthesis. FIG. 12 discloses "AAAAAAAAAAAA" as SEQ ID NO: 7.

FIG. 13 illustrates the synthesis of an amplicon for isothermal amplification of a library of analytes.

FIG. 14 shows the synthesis of an amplicon for SDA amplification.

FIG. 15 shows the ligation of a primer binding site for isothermal amplification.

FIG. 16 shows the binding of an analyte to an array with SPEs and UPEs for solid phase amplification. FIG. 16 discloses "TTTTTTTTTT" as SEQ ID NO: 12.

FIG. 17 discloses "TTTTTTTTTT" as SEQ ID NO: 12.

FIG. 19 discloses "TTTTTTTTTT" as SEQ ID NO: 12 and "AAAAAAAAAA" as SEQ ID NO: 13.

FIG. 20 depicts an amplification array for comparative analysis.

FIG. 21 illustrates the use of an array with SPEs and UPEs for SNP analysis.

FIG. 23 shows the binding of primers to extended SPEs on an array.

FIG. 24 demonstrates the binding of primers and extended primers to SPEs on an array.

FIG. 25 shows the extension of primers and SPEs on an array in accordance with amplification disclosed in this invention.

FIG. 26 depicts the binding of nucleic acid portions of chimeric compositions to complementary sequences on an array.

FIG. 32 is a gel analysis that shows transcription from libraries made from sequential synthesis of 2nd strands as further described in Example 10 below.

DETAILED DESCRIPTION OF THE INVENTION

Figure 17:
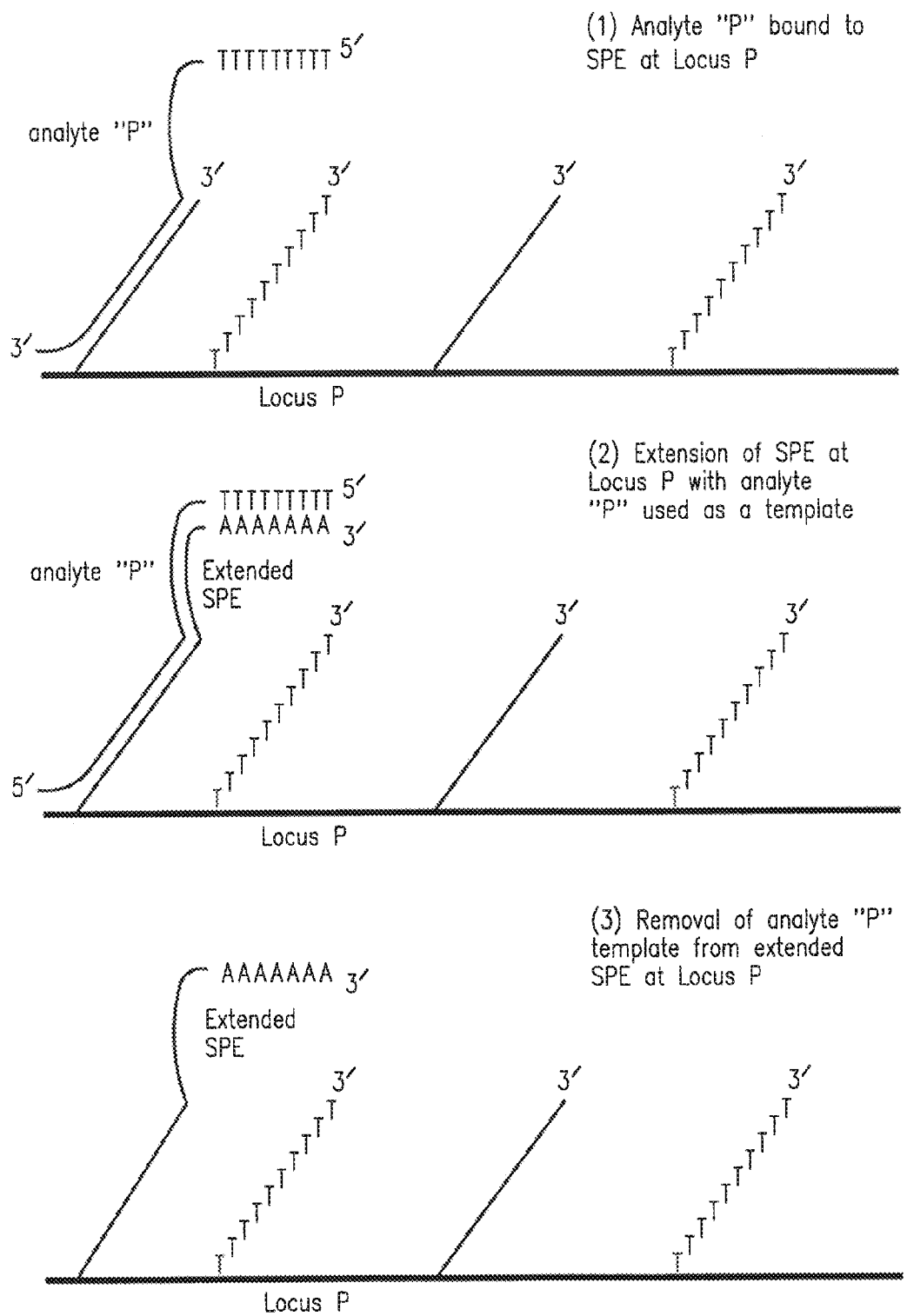
FIG. 17 shows the extension of an SPE on an array during solid phase amplification.
Figure 18:
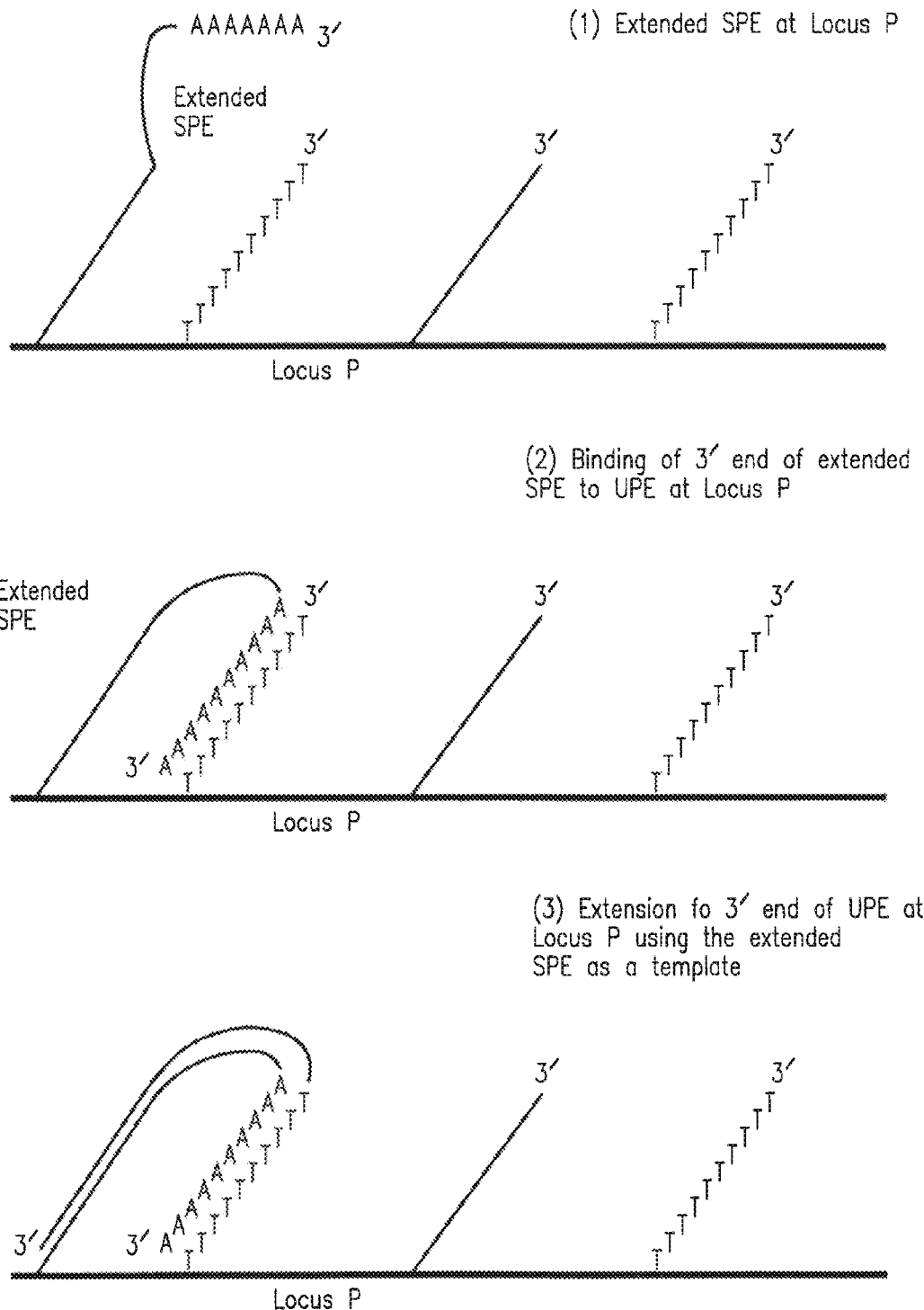
FIG. 18 shows the binding of an UPE to an extended SPE followed by extension of the UPE during solid phase amplification FIG. 18 discloses "TTTTTTTTTT" as SEQ ID NO: 12 and "AAAAAAAAAA" as SEQ ID NO: 13.
Figure 19:
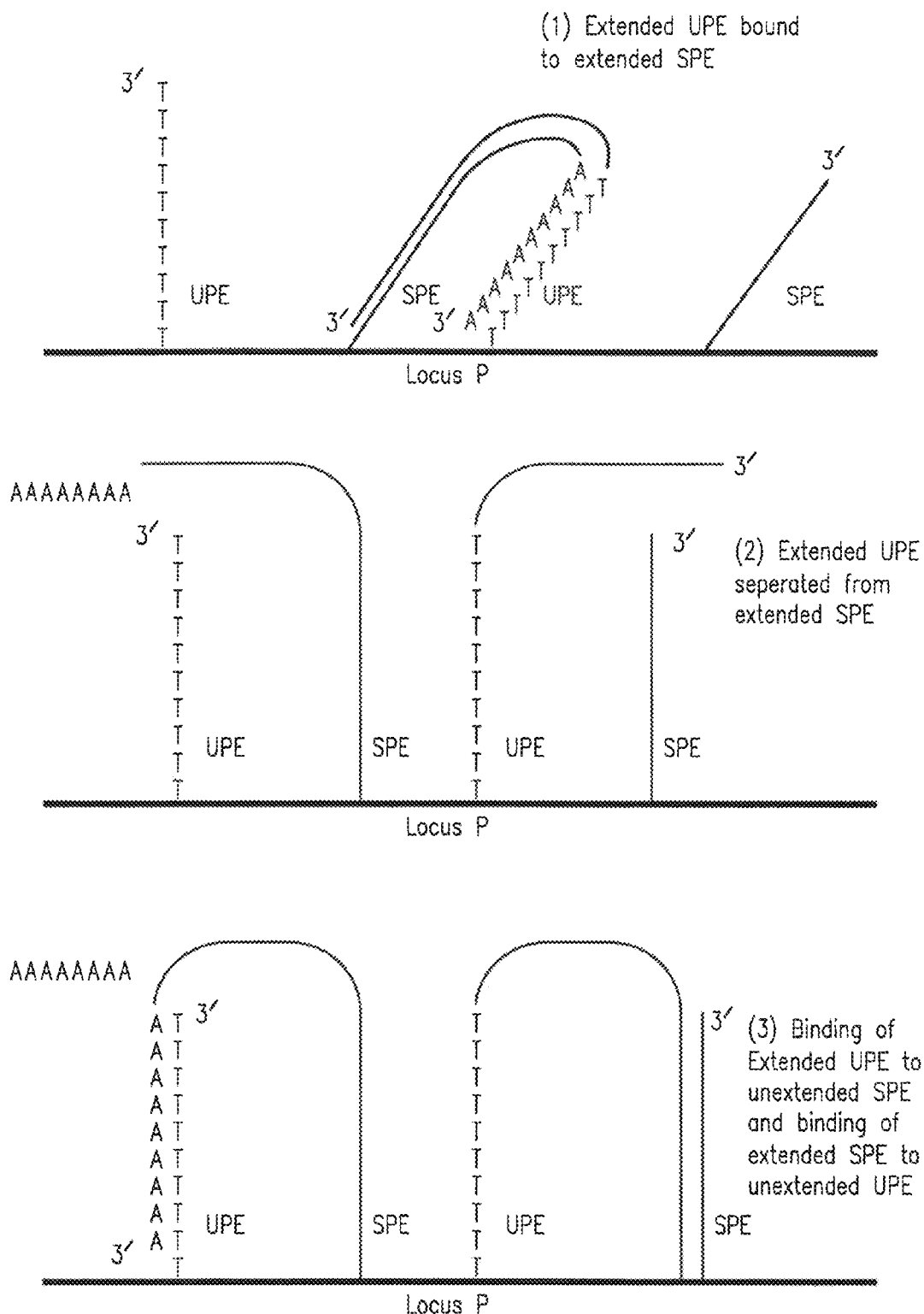
FIG. 19 shows solid phase amplification in which binding of extended SPEs and UPEs to unextended SPEs and UPEs occur.
Figure 22:
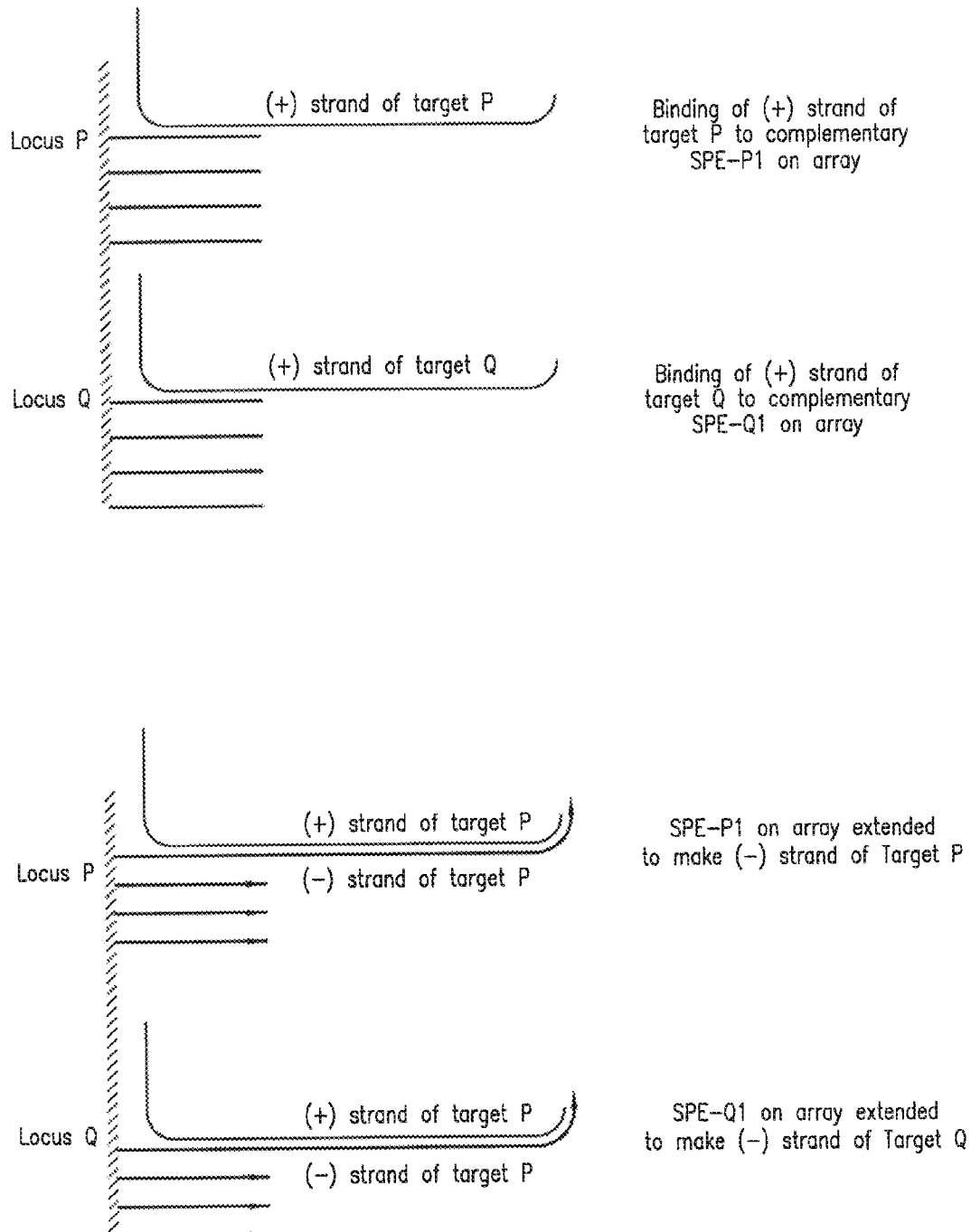
FIG. 22 relates to binding of analytes to SPEs on an array.

The present invention discloses novel methods, compositions and kits that can be used in making and analyzing a library of nucleic acids. The nucleic acids in the sample being tested can be used directly for signal generation or they can be used as templates to provide one or more nucleic acid copies that comprise sequences that are either identical or complementary to the original sequences.

In the present invention the following terms are used and defined below:

An analyte is a biological polymer or ligand that is isolated or derived from biological sources such as organs, tissues or cells, or non-biological sources by synthetic or enzymatic means or processes. Examples of biological polymers can include but are not limited to oligonucleotides, polynucleotides, oligopeptides, polypeptides, oligosaccharides, polysaccharides and lipids. Examples of ligands can include but are not necessarily limited to non-peptide antigens, hormones, enzyme substrates, vitamins, drugs, and non-peptide signal molecules.

A library is a diverse collection of nucleic acids that comprises: a) analytes; b) nucleic acids derived from analytes that comprise sequences that are complementary to sequences in the analytes; c) nucleic acids derived from analytes that comprise sequences that are identical to sequences in the analytes; and d) any combination of the foregoing.

A label is any moiety that is capable of directly or indirectly generating a signal.

A production center is a segment of a nucleic acid or analogue thereof that is capable of producing more than one copy of a sequence that is identical or complementary to sequences that are operably linked to the production center.

Universal Detection Targets (UDTs) are defined as common or conserved segments in diverse nucleic acids that are present in populations of nucleic acids in a sample and are capable of recognition by a corresponding binding partner. The UDTs may be intrinsic or they may be artificially incorporated into nucleic acids. Examples of inherent UDTs can comprise but not be limited to 3' poly A segments, 5' caps, secondary structures and consensus sequences. Examples of inherent consensus sequences that might find use in the present invention can comprise but not be limited to signal sites for poly A addition, splicing elements and multicopy repeats such as Alu sequences. UDTs may also be artificially incorporated into nucleic acids by an addition to the original analyte nucleic acid or during synthesis of nucleic acids that comprise sequences that are identical or complementary to the sequences of the original analytes. Artificially added UDTs may be labeled themselves or they may serve as binding partners.

Universal Detection Elements (UDEs) are comprised of two segments: a first segment that is capable of acting as a binding partner for a UDT and a second segment that is either labeled or otherwise capable of generating a detectable signal. In some cases the first and second segments can be overlapping or even comprise the same segments. When UDEs are labeled, they may comprise a single signal moiety or they may comprise more than one signal entity. Segments of UDEs involved in binding to UDTs or signal generation may comprise but not be limited to polymeric substances such as nucleic acids, nucleic acid analogues, polypeptides, polysaccharides or synthetic polymers.

The present invention discloses the use of UDTs and UDEs for the purpose of array analysis. The present invention also discloses novel methods for incorporation of production centers into nucleic acid libraries that may be used in array analysis. These production centers may provide amplification of sequences that are identical or complementary to sequences in the original diverse nucleic acid analytes. The products derived from these production centers may be labeled themselves or UDTs may be incorporated for detection purposes. Nucleic acids that may be of use in the present invention can comprise or be derived from DNA or RNA. The original population of nucleic acids may comprise but not be limited to genomic DNA, unspliced RNA, mRNA, rRNA and snRNA.

This invention provides a composition of matter that comprises a library of analytes, the analytes being hybridized to an array of nucleic acids, the nucleic acids being fixed or immobilized to a solid support, wherein the analytes comprise an inherent universal detection target (UDT), and a universal detection element (UDE) attached to the UDT, wherein the UDE generates a signal indicating the presence or quantity of the analytes, or the attachment of UDE to UDT. The library of analytes can be derived from a biological source selected from the group consisting of organs, tissues and cells, or they may be from non-natural sources as discussed in the definitions section above. Biological analytes can be selected from the group consisting of genomic DNA, episomal DNA, unspliced RNA, mRNA, rRNA, snRNA and a combination of any of the foregoing. The nucleic acid array can be selected from the group consisting of DNA, RNA and analogs thereof, an example of the latter being PNA. Such nucleic acids or analogs can be modified on any one of the sugar, phosphate or base moieties. The solid support can take a number of different forms, including being porous or non-porous. A porous solid support can be selected from the group consisting of polyacrylamide and agarose. A non-porous solid support may comprise glass or plastic. The solid support can also be transparent, translucent, opaque or reflective.

Nucleic acids can be directly or indirectly fixed or immobilized to the solid support. In terms of indirect attachment, the nucleic acids can be indirectly fixed or immobilized to the solid support by means of a chemical linker or linkage arm.

As discussed elsewhere in this disclosure, the inherent UDT can selected from the group consisting of 3' polyA segments, 5' caps, secondary structures, consensus sequences and a combination of any of the foregoing. The consensus sequences can be selected from the group consisting of signal sequences for polyA addition, splicing elements, multicopy repeats and a combination of any of the foregoing. As also discussed elsewhere in this disclosure, the UDEs can be selected from the group consisting of nucleic acids, nucleic acid analogs, polypeptides, polysaccharides, synthetic polymers and a combination of any of the foregoing. As mentioned previously, such analogs can take the form of PNA. The UDE generates a signal directly or indirectly. Direct signal generation can take any number of forms and can be selected from the group consisting of a fluorescent compound, a phosphorescent compound, a chemiluminescent compound, a chelating compound, an electron dense compound, a magnetic compound, an intercalating compound, an energy transfer compound and a combination of any of the foregoing. Where indirect signal generation is desired, such can take a number of different forms and in this regard can be selected from the group consisting of an antibody, an antigen, a hapten, a receptor, a hormone, a ligand, an enzyme and a combination of any of the foregoing. Among suitable enzymes which can be indirectly detected, these would include enzymes which catalyze any reaction selected from the group consisting of a fluorogenic reaction, a chromogenic reaction and a chemiluminescent reaction.

This invention also provides a composition of matter that comprises a library of analytes, such analytes being hybridized to an array of nucleic acids, and such nucleic acids being fixed or immobilized to a solid support, wherein the analytes comprise a non-inherent universal detection target (UDT) and a universal detection element (UDE) hybridized to the UDT, and wherein the UDE generates a signal directly or indirectly to detect the presence or quantity of such analytes. The nature of the analyte, the nucleic acid array, modifications, solid support are as described in the preceding paragraphs above. The non-inherent universal detection targets (UDTs) can comprise homopolymeric sequences or heteropolymeric sequences. The universal detection elements (UDEs) can be selected from the group consisting of nucleic acids, nucleic acid analogs and modified forms thereof. The UDEs generate a signal directly or indirectly, such direct and indirect signal generation also being discussed in the paragraphs just above.

The present invention further provides a composition of matter that comprises a library of analytes, such analytes being hybridized to an array of nucleic acids, and such nucleic acids being fixed or immobilized to a solid support, wherein the hybridization between the analytes and the nucleic acids generate a domain for complex formation, and the composition further comprises a signaling entity complexed to the domain. Statements and features regarding the nature of the library of analytes, the nucleic acid array, the solid support and fixation or immobilization thereto, and direct/indirect signal generation are as discussed hereinabove, particularly the last several paragraphs. Notably, the domain for complex formation can be selected from the group consisting of DNA-DNA hybrids, DNA-RNA hybrids, RNA-RNA hybrids, DNA-PNA hybrids and RNA-PNA hybrids. The signaling entity that is complexed to the domain can be selected from the group consisting of proteins and intercalators. Such proteins can comprise nucleic acid binding proteins which bind preferentially to double-stranded nucleic acid, the latter comprising antibodies, for example. These antibodies are specific for nucleic acid hybrids and are selected from the group consisting of DNA-DNA hybrids, DNA-RNA hybrids, RNA-RNA hybrids, DNA-PNA hybrids and RNA-PNA hybrids. In accordance with the present invention, useful intercalators can be selected from the group consisting of ethidium bromide, diethidium bromide, acridine orange and SYBR Green. When employed in accordance with the present invention, the proteins generate a signal directly or indirectly. Such forms and manner of direct and indirect signal generation are as described elsewhere in this disclosure, particularly in several paragraphs above.

Related to the above described compositions are unique and useful processes. The present invention thus provides a process for detecting or quantifying more than one nucleic acid of interest in a library comprising the steps of: a) providing: (i) an array of fixed or immobilized nucleic acids complementary to the nucleic acids of interest; (ii) a library of nucleic acid analytes which may contain the nucleic acids of interest sought to be detected or quantified, wherein each of the nucleic acids of interest comprise at least one inherent universal detection target (UDT); and (iii) universal detection elements (UDE) which generates a signal directly or indirectly; b) hybridizing the library (ii) with the array of nucleic acids (i) to form hybrids if the nucleic acids of interest are present; c) contacting the UDEs with the UDTs to form a complex bound to the array; d) detecting or quantifying the more than one nucleic acid of interest by detecting or measuring the amount of signal generated from UDEs bound to the array. Many of these elements have been described previously in this disclosure, but at the risk of some redundancy, elaboration is now made. For example, the nucleic acid array can be selected from the group consisting of DNA, RNA and analogs thereof, the latter comprising PNA. Modifications to these nucleic acids and analogs can be usefully carried out to any one of the sugar, phosphate or base moieties. The solid support can be porous, e.g., polyacrylamide and agarose, or non-porous, e.g., glass or plastic. The solid support can also be transparent, translucent, opaque or reflective.

Nucleic acids are directly or indirectly fixed or immobilized to the solid support. Indirect fixation or immobilization to the solid support can be carried out by means of a chemical linker or linkage arm. As discussed elsewhere herein, the library of analytes can be derived from a biological source selected from the group consisting of organs, tissues and cells, or they may be from non-natural or more synthetic or man-made sources. Among biological analytes are those selected from the group consisting of genomic DNA, episomal DNA, unspliced RNA, mRNA, rRNA, snRNA and a combination of any of the foregoing.

The inherent UDT used in the above process can be selected from the group consisting of 3' polyA segments, 5' caps, secondary structures, consensus sequences, and a combination of any of the foregoing. Such consensus sequences can be selected from the group consisting of signal sequences for polyA addition, splicing elements, multicopy repeats, and a combination of any of the foregoing. UDEs can be selected from the group consisting of nucleic acids, nucleic acid analogs, e.g., PNA, polypeptides, polysaccharides, synthetic polymers and a combination of any of the foregoing. UDEs generate a signal directly or indirectly. Direct signal generation can be various and may be selected from the group consisting of a fluorescent compound, a phosphorescent compound, a chemiluminescent compound, a chelating compound, an electron dense compound, a magnetic compound, an intercalating compound, an energy transfer compound and a combination of any of the foregoing. Indirect signal generation can also be various and may be selected from the group members consisting of an antibody, an antigen, a hapten, a receptor, a hormone, a ligand, an enzyme and a combination of any of the foregoing. When desired and employed in the process at hand, such an enzyme catalyzes a reaction selected from the group consisting of a fluorogenic reaction, a chromogenic reaction and a chemiluminescent reaction. Those skilled in the art will readily appreciate that the above-described process can further comprise one or more washing steps.

This invention provides another such process for detecting or quantifying more than one nucleic acid of interest in a library comprising the steps of a) providing: (i) an array of fixed or immobilized nucleic acids complementary to the nucleic acids of interest; (ii) a library of nucleic acid analytes which may contain the nucleic acids of interest sought to be detected or quantified, wherein each of the nucleic acids of interest comprise at least one inherent universal detection target (UDT); and (iii) universal detection elements (UDE) which generates a signal directly or indirectly; b) contacting the UDEs with the UDTs in the library of nucleic acid analytes to form one or more complexes; c) hybridizing the library of nucleic acid analytes with the array of nucleic acids (i) to form hybrids if such nucleic acids of interest are present; d) detecting or quantifying the more than one nucleic acid of interest by detecting or measuring the amount of signal generated from UDEs bound to the array. The nature and form of the nucleic acid array, modifications, solid support, direct/indirect fixation or immobilization, library of analytes, inherent UDT, UDE, direct/indirect signal generation, and the like, are as described elsewhere in this disclosure, including more particularly the last several paragraphs above. Furthermore, this process can comprise one or more conventional washing steps.

Another process for detecting or quantifying more than one nucleic acid of interest in a library comprises the steps of a) providing (i) an array of fixed or immobilized nucleic acids complementary to the nucleic acids of interest; (ii) a library of nucleic acid analytes which may contain the nucleic acids of interest sought to be detected or quantified, wherein each of the nucleic acids of interest comprise at least one non-inherent universal detection target (UDT), wherein the non-inherent UDT is attached to the nucleic acid analytes; and (iii) universal detection elements (UDE) which generate a signal directly or indirectly; b) hybridizing the library (ii) with the array of nucleic acids (i) to form hybrids if the nucleic acids of interest are present; c) contacting the UDEs with the UDTs to form a complex bound to the array; d) detecting or quantifying the more than one nucleic acid of interest by detecting or measuring the amount of signal generated from UDEs bound to the array. As described variously in this disclosure, the nature and form of the nucleic acid array, modifications to nucleic acid and nucleic acid analogs, the solid support, direct and indirectfixation/immobilization to the solid support, the library of analytes, direct and indirect signal generation, and the like, are as described elsewhere in this disclosure. Of particular mention are the non-inherent universal detection targets (UDTs) which can comprise homopolymeric sequences and heteropolymeric sequences. Also of particular mention are the universal detection elements (UDEs) which can be selected from the group consisting of nucleic acids, nucleic acid analogs, e.g., PNA, and modified forms thereof. One or more washing steps can be included in this last process.

Another process for detecting or quantifying more than one nucleic acid of interest in a library comprises the steps of a) providing (i) an array of fixed or immobilized nucleic acids complementary to the nucleic acids of interest; (ii) a library of nucleic acid analytes which may contain the nucleic acids of interest sought to be detected or quantified, wherein each of such nucleic acids of interest comprise at least one non-inherent universal detection target (UDT), wherein the non-inherent UDTs are attached to the nucleic acid analytes; and (iii) universal detection elements (UDE) which generate a signal directly or indirectly; b) contacting the UDEs with the UDTs in the library of nucleic acid analytes to form one or more complexes; c) hybridizing the library (ii) with the array of nucleic acids (i) to form hybrids if such nucleic acids of interest are present; d) detecting or quantifying the more than one nucleic acid of interest by detecting or measuring the amount of signal generated from UDEs bound to the array. Descriptions for the nucleic acid array, modifications, solid support, direct/indirect fixation or immobilization to the solid support, the library of analytes, the non-inherent universal detection targets (UDTs), the universal detection elements (UDEs), direct/indirect signal generation, inclusion of washing steps, and the like, are found elsewhere in this disclosure and are equally applicable to this last described process.

Another process for detecting or quantifying more than one nucleic acid of interest in a library comprises the steps of a) providing (i) an array of fixed or immobilized nucleic acids complementary to the nucleic acids of interest; (ii) a library of nucleic acid analytes which may contain the nucleic acids of interest sought to be detected or quantified; (iii) means for attaching one or more universal detection targets (UDT) to a nucleic acid; (iv) universal detection elements (UDE) which generates a signal directly or indirectly; b) attaching such UDTs (iii) to the library of nucleic acid analytes (ii); c) hybridizing the library (ii) with the array of nucleic acids (i) to form hybrids if such nucleic acids of interest are present; d) contacting the UDEs with the UDTs to form a complex bound to the array; e) detecting or quantifying the more than one nucleic acid of interest by detecting or measuring the amount of signal generated from UDEs bound to the array. Many of these elements have been described already. These include the nucleic acid array, nucleic acid analogs, sugar, phosphate and base modifications, the solid support, direct/indirect fixation and immobilization to the solid support, the library of analytes, the universal detection elements, direct/indirect signal generation, inclusion of additional washing steps, and the like, have been described elsewhere above and below and are equally applicable to this last-mentioned process. Of special mention are attaching means which add homopolymeric sequences through various enzymes, e.g., poly A polymerase and terminal transferase. Other attaching means can be used for adding homopolymeric or heteropolymeric sequences, and these include enzymatic means and enzymes selected from DNA ligase and RNA ligase.

Still another process for detecting or quantifying more than one nucleic acid of interest in a library comprises the steps of a) providing (i) an array of fixed or immobilized nucleic acids complementary to the nucleic acids of interest; (ii) a library of nucleic acid analytes which may contain the nucleic acids of interest sought to be detected or quantified; (iii) means for attaching one or more universal detection targets (UDT) to a nucleic acid; (iv) universal detection elements (UDE) which generate a signal directly or indirectly; b) attaching the UDTs (iii) to the library of nucleic acid analytes (ii); c) contacting the UDEs with the UDTs in the library of nucleic acid analytes to form one or more complexes; d) hybridizing the library (ii) with the array of nucleic acids (i) to form hybrids if such nucleic acids of interest are present; e) detecting or quantifying the more than one nucleic acid of interest by detecting or measuring the amount of signal generated from UDEs bound to the array. As might be expected, the elements recited in this process have been described elsewhere in this disclosure and are equally applicable to this last described process. These previously described elements include the nucleic acid array, modifications, the solid support, direct/indirect fixation or immobilization to the solid support, the library of analytes, attaching means, UDE, direct/indirect signal generation and the inclusion of washing steps.

Another process for detecting or quantifying more than one nucleic acid of interest in a library comprises the steps of a) providing (i) an array of fixed or immobilized nucleic acids complementary to the nucleic acids of interest; (ii) a library of nucleic acid analytes which may contain the nucleic acids of interest sought to be detected or quantified; and (iii) universal detection elements (UDEs) which bind to a domain formed by nucleic acid hybrids for complex formation and generate a signal directly or indirectly; b) hybridizing the library (ii) with the array of nucleic acids (i) to form hybrids if such nucleic acids of interest are present, wherein any formed hybrids generate a domain for complex formation; c) contacting the UDEs with any hybrids to form a complex bound to the array; d) detecting or quantifying the more than one nucleic acid of interest by detecting or measuring the amount of signal generated from UDEs bound to the array. Descriptions for the nucleic acid array, nucleic acid analogs, e.g., PNA, modifications (sugar, base and phosphate moieties), the solid support, fixation/immobilization, the library of analytes, the domain for complex formation, direct/indirect signal generation from signaling proteins, washing steps, and the like, have already been given above and are equally applicable to this last mentioned process. Of special note is this process wherein the signaling entity is complexed to the domain for complex formation, such signaling entity being selected from proteins and intercalators. Such proteins can include nucleic acid binding proteins which bind preferentially to double-stranded nucleic acids, e.g., antibodies, particularly such antibodies which are specific for nucleic acid hybrids, e.g., DNA-DNA hybrids, DNA-RNA hybrids, RNA-RNA hybrids, DNA-PNA hybrids and RNA-PNA hybrids. Intercalators have also been previously described in this disclosure and can be selected from ethidium bromide, diethidium bromide, acridine orange and SYBR Green.

Other compositions of matter are provided by this invention. One such composition comprises a library of first nucleic acid analyte copies, such first nucleic acid copies being hybridized to an array of nucleic acids, those nucleic acids being fixed or immobilized to a solid support, wherein such first nucleic acid copies comprise an inherent universal detection target (UDT) and a universal detection element (UDE) attached to the UDT, wherein the UDE generates a signal directly or indirectly to detect the presence or quantity of any analytes. The library of analytes, e.g., biological sources, and examples of such analytes, e.g., genomic DNA, episomal DNA, unspliced RNA, mRNA, rRNA, snRNA and a combination of any of the foregoing, has been described above. Equally so, the nucleic acid array has been already described, including, for example, DNA, RNA and analogs thereof, e.g., PNA. Modifications to the nucleic acids and analogs (sugar, phosphate, base), features of the solid support (porous/non-porous, transparent, translucent, opaque, reflective), fixation/immobilization to the solid support, the inherent UDT, the UDE, direct/indirect signal generation from UDEs have been described above and apply equally to this last composition.

Another composition of matter comprises a library of first nucleic acid analyte copies, such first nucleic acid copies being hybridized to an array of nucleic acids, the nucleic acids being fixed or immobilized to a solid support, wherein such first nucleic acid copies comprise one or more non-inherent universal detection targets (UDTs) and one or more universal detection elements (UDEs) attached to the UDTs, wherein the UDEs generate a signal directly or indirectly to detect the presence or quantity of any analytes, and wherein the UDTs are either: (i) at the 5' ends of the first nucleic acid copies and not adjacent to an oligoT segment or sequence, or (ii) at the 3' ends of the first nucleic acid copies, or (iii) both (i) and (ii). The library of analytes, nucleic acid array, nucleic acid modifications, solid support, fixation/immobilization to the solid support, non-inherent UDTs, e.g., heteropolymeric sequences, UDEs (e.g., nucleic acids, nucleic acid analogs, polypeptides, polysaccharides, synthetic polymers, etc), direct/indirect signal generation from UDEs have already been described above and are applicable to this last described composition.

Another process for detecting or quantifying more than one nucleic acid of interest in a library comprises the steps of a) providing (i) an array of fixed or immobilized nucleic acids identical in part or whole to the nucleic acids of interest; (ii) a library of nucleic acid analytes which may contain the nucleic acids of interest sought to be detected or quantified, wherein each of such nucleic acids of interest comprise at least one inherent universal detection target (UDT); (iii) universal detection elements (UDE) which generate a signal directly or indirectly; and (iv) polymerizing means for synthesizing nucleic acid copies of the nucleic acids of analytes; b) synthesizing one or more first nucleic acid copies which are complementary to all or part of the nucleic acid analytes and synthesizing sequences which are complementary to all or part of the UDT to form a complementary UDT; c) hybridizing such first nucleic acid copies with the array of nucleic acids (i) to form hybrids if such nucleic acids of interest are present; d) contacting the UDEs with the complementary UDTs of the first nucleic acid copies to form a complex bound to the array; e) detecting or quantifying the more than one nucleic acid of interest by detecting or measuring the amount of signal generated from UDEs bound to the array. Statements and descriptions for the nucleic acid array, modifications, solid support, fixation/immobilization, the library of analytes, inherent UDTs, e.g., consensus sequences, UDEs, direct/indirect signal generation from UDEs, have been given above and are equally applicable to this last process. Of special mention are the recited polymerizing means which can be selected from *E. coli* DNA Pol I, Klenow fragment of *E. coli* DNA Pol I, Bst DNA polymerase, Bca DNA polymerase, Taq DNA polymerase, Tth DNA Polymerase, T4 DNA polymerase, ALV reverse transcriptase, MuLV reverse transcriptase, RSV reverse transcriptase, HIV-1 reverse transcriptase, HIV-2 reverse transcriptase, Sensiscript and Omniscript.

Another embodiment provided by this invention is a process for detecting or quantifying more than one nucleic acid of interest in a library comprising the steps of a) providing (i) an array of fixed or immobilized nucleic acids identical in part or whole to the nucleic acids of interest; (ii) a library of nucleic acid analytes which may contain the nucleic acids of interest sought to be detected or quantified, wherein each of such nucleic acids of interest comprise at least one inherent universal detection target (UDT); (iii) universal detection elements (UDE) which generate a signal directly or indirectly; and (iv) polymerizing means for synthesizing nucleic acid copies of such nucleic acid analytes; b) synthesizing one or more first nucleic acid copies of such nucleic acid analytes; c) contacting the UDEs with the UDTs in the first nucleic acid copies to form one or more complexes; d) hybridizing such first nucleic acid copies with the array of nucleic acids (i) to form hybrids if such nucleic acids of interest are present; and e) detecting or quantifying the more than one nucleic acid of interest by detecting or measuring the amount of signal generated from UDEs bound to the array. The nucleic acid array, nucleic acid modifications, the solid support, fixation/immobilization (direct and indirect), the library of analytes, inherent UDTs, UDEs, signal generation from UDEs (direct/indirect), polymerizing means, have been described above. Such descriptions are equally applicable to this last process.

Another process for detecting or quantifying more than one nucleic acid of interest in a library comprises the steps of a) providing (i) an array of fixed or immobilized nucleic acids identical in part or whole to the nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) attaching the non-inherent UDTs to either the 3' ends of the nucleic acid analytes, the 5' ends of the first nucleic acid analytes, or both the 3' ends and the 5' ends of the nucleic acid analytes; c) synthesizing one or more first nucleic acid copies of the nucleic acid analytes; d) hybridizing the first nucleic acid copies with the array of nucleic acids (i) to form hybrids if such nucleic acids of interest are present; e) contacting the UDEs with the UDTs of the first nucleic acid copies to form a complex bound to the array; and f) detecting or quantifying the more than one nucleic acid of interest by detecting or measuring the amount of signal generated from UDEs bound to the array. See many of the preceding paragraphs for descriptions and characteristics of the nucleic acid array, modifications, the solid support, fixation/immobilization, the library of analytes, attaching means, UDEs, direct/indirect signal generation from UDEs, polymerizing means, and the like.

Yet another process for detecting or quantifying more than one nucleic acid of interest in a library comprises the steps of a) providing (i) an array of fixed or immobilized nucleic acids identical in part or whole to the nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) attaching such non-inherent UDTs to either the 3' ends of the nucleic acid analytes, the 5' ends of the first nucleic acid analytes, or both the 3' ends and the 5' ends of the nucleic acid analytes; c) synthesizing one or more first nucleic acid copies of the nucleic acid analytes; d) contacting the UDEs with the UDTs of the first nucleic acid copies to form complexes; e) hybridizing the first nucleic acid copies with the array of nucleic acids (i) to form hybrids if any nucleic acids of interest are present; f) detecting or quantifying the more than one nucleic acid of interest by detecting or measuring the amount of signal generated from UDEs bound to the array. The nucleic acid array, modifications, the solid support, direct/indirect fixation/immobilization, the library of analytes, attachment means, UDEs, signal generation from UDEs, direct/indirect signal generation, polymerizing means, and the like, have already been described. Such descriptions are equally applicable to this last-described process.

Another process for detecting or quantifying more than one nucleic acid of interest in a library comprises the steps of a) providing (i) an array of fixed or immobilized nucleic acids identical in part or whole to such nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) synthesizing one or more first nucleic acid copies of the nucleic acid analytes; c) attaching the non-inherent UDTs to either the 3' ends of the first nucleic acid copies, the 5' ends of the first nucleic acid copies, or both the 3' ends and the 5' ends of the first nucleic acid copies; d) hybridizing the first nucleic acid copies with the array of nucleic acids (i) to form hybrids if any nucleic acids of interest are present; e) contacting the UDEs with the UDTs of the first nucleic acid copies to form a complex bound to the array; and f) detecting or quantifying the more than one nucleic acid of interest by detecting or measuring the amount of signal generated from UDEs bound to the array. Descriptions for the above-recited elements have been given above and are equally applicable to this last process.

Still another process provided by this invention is for detecting or quantifying more than one nucleic acid of interest in a library comprises the steps of a) providing (i) an array of fixed or immobilized nucleic acids identical in part or whole to the nucleic acids of interest; (ii) a library of nucleic acid analytes which may contain the nucleic acids of interest sought to be detected or quantified; (iii) means for attaching one or more non-inherent universal detection targets (UDT) to a nucleic acid; (iv) universal detection elements (UDE) which generate a signal directly or indirectly; and (v) polymerizing means for synthesizing nucleic acid copies of the nucleic acid analytes; b) synthesizing one or more first nucleic acid copies of the nucleic acid analytes;

c) attaching the non-inherent UDTs to either the 3' ends of the first nucleic acid copies, the 5' ends of the first nucleic acid copies, or both the 3' ends and the 5' ends of the first nucleic acid copies; d) contacting the UDEs with the UDTs of the first nucleic acid copies to form a complex; e) hybridizing the first nucleic acid copies with the array of nucleic acids (i) to form hybrids if any nucleic acids of interest are present; and f) detecting or quantifying the more than one nucleic acid of interest by detecting or measuring the amount of signal generated from UDEs bound to the array. These elements and subelements have been described elsewhere in this disclosure. Such descriptions apply to this last process.

Yet another process for detecting or quantifying more than one nucleic acid of interest in a library comprises the steps of a) providing (i) an array of fixed or immobilized nucleic acids complementary to the nucleic acids of interest; (ii) a library of nucleic acid analytes which may contain the nucleic acids of interest sought to be detected or quantified; (iii) universal detection elements (UDEs) which bind to a domain for complex formation formed by nucleic acid hybrids and generate a signal directly or indirectly; and (iv) polymerizing means for synthesizing nucleic acid copies of the nucleic acid analytes; b) synthesizing one or more nucleic acid copies of the nucleic acid analytes; c) hybridizing the first nucleic acid copies with the array of nucleic acids (i) to form hybrids if any nucleic acids of interest are present, wherein any formed hybrids generate a domain for complex formation; d) contacting the UDEs with the hybrids to form a complex bound to the array; and e) detecting or quantifying the more than one nucleic acid of interest by detecting or measuring the amount of signal generated from UDEs bound to the array. The above-recited elements and subelements and variations thereof are described elsewhere in this disclosure and are equally applicable to this just-mentioned process.

One aspect of the present invention discloses methods that eliminate the necessity for enzymatic incorporation of labeled nucleotides by an end user. In this particular aspect, common or conserved features present in a diverse population of nucleic acid analytes are used to assay the extent of hybridization of the analytes to discrete target elements in an array format. These common or conserved features are Universal Detection Targets (UDTs) which can provide signal generation by binding of Universal Detection Elements (UDEs).

Examples of UDTs that may be inherently present in a population of diverse nucleic acid analytes can comprise but not be limited to 3' poly A segments, 5' caps, secondary structures and consensus sequences. Examples of consensus sites that might find use in the present invention can comprise but not be limited to signal sites for poly A addition, splicing elements and multicopy repeats such as Alu sequences.

UDEs may be directly or indirectly labeled. Examples of directly labels can comprise but not be limited to any members of a group consisting of a fluorescent compound, a phosphorescent compound, a chemiluminescent compound, a chelating compound, an electron dense compound, a magnetic compound, an intercalating compound, an energy transfer compound and a combination of any of the foregoing.

Examples of indirect labels can comprise but not be limited to any members of a group consisting of an antibody, an antigen, a hapten, a hormone, a receptor, a ligand, an enzyme and a combination of any of the foregoing. Among such enzymes are any enzymes which catalyze reactions selected from the group consisting of a fluorogenic reaction, a chromogenic reaction and a chemiluminescent reaction.

RNA and DNA polymerases sometimes have difficulty in accepting labeled nucleotides as substrates for polymerization. In prior art, this shortcoming can result in the production of a labeled library that consists of short strands with few signal generating entities. Limitations caused by such inefficient incorporation can be partially compensated for by increasing the amount of labeled precursors in the reaction mixtures. However, this method achieves only a moderate improvement and entails a higher cost and waste of labeled reagents. In contrast, this particular aspect of the present invention discloses means by which diverse nucleic acids in a library can be hybridized in an array format in their native form without the need of any manipulations or modifications and then be detected by the presence of UDTs bound to the array.

An illustrative depiction of this process is given in FIG. 1. Although there are multiple unique species of mRNA that can make up a diverse population of nucleic acids in a sample, the common elements that are shared by these nucleic acids can be used as UDTs. Hybridization of the mRNA to an array permits the localization of individual species to discrete locations on the array. The determination of the amount of sample that is bound to each locus of an array is then carried out by detection of the amount of UDT present at each locus by binding of the appropriate UDE. Thus, in FIG. 1, locus 1 and 3 would be capable of generating an amount of signal that would be proportionate to the amount of mRNA bound to each of those sites. On the other hand there would little or no signal generation from locus 2 since there was little or no mRNA bound to that site. A single labeled species of mostly or completely poly T or U could be used as a UDE to quantify the amount of poly A tails of the various species of eucaryotic mRNA in FIG. 1. In this way, a single universal species of labeled material is synthesized for use as a UDE thereby providing an inexpensive and efficient means of indirectly labeling the RNA molecules being quantified.

A nucleic acid UDE can be prepared either chemically or enzymatically. For example, oligonucleotide synthesizers are commercially available that can produce a UDE consisting of labeled poly T/U sequences for detection of the poly A UDT described above. Both the amount and placement of labeled moieties can be tightly controlled by this method. Also, since this is a homopolymeric product, probes that are shorter by one or more bases will still be effective such that the net yield of usable product will be higher than one that requires a discrete specific sequence. On the other hand, methods of synthesizing such sequences enzymatically are also well known to those versed in the art. Commonly, a tetramer of dT is used as a primer for addition of poly T or poly U by terminal transferase. Each base can be modified to be capable of signal generation or a mixture of labeled and unlabeled bases can be used. Although A Poly A UDT has been described in the example above, when different sequences are used as UDTs, the synthesis of the corresponding UDEs can be carried out by the same chemical and enzymatic methodologies described above. It is also contemplated that analogues of DNA can also be used to synthesize the UDEs. For instance, instead of using DNA, labeled RNA or PNA (peptide nucleic acids) may also be used.

Detection and quantification of the amount of UDTs bound to particular loci can also be carried out by the use of an antibody acting as a UDE. Examples of antibody specificities that are useful for UDEs can comprise but not be limited to recognition of the cap element at the 5' end of mature mRNAs or the homopolymeric poly A sequence. Furthermore, hybridization between nucleic acids is an event that in and of itself is capable of generating a UDT that can be recognized by antibody UDEs. For example, when a library of diverse RNA species are bound to an array, the RNA, DNA or PNA target elements in the array will generate RNA/RNA, RNA/DNA or RNA/PNA hybrids at each of the loci that has homology with the particular RNA species being quantified. Although each of the sites has a discrete sequence, universal detection and quantification can be carried out by antibodies that recognize the change in physical structure produced by such hybridization events. Alternatively, the hybridization between a UDE and the complementary UDT of a nucleic acid bound to the target elements of the array can be detected by an appropriate antibody. The antibodies that are specific for the UDEs described above can be labeled themselves or secondary labeled antibodies can be used to enhance the signal.

If only a single library of mRNA is being analyzed, binding of a UDE to a UDT may take place before or after hybridization of the RNA to an array of detection probes. The particular order of events will depend upon the nature and stability of the binding partners. When analytes from two libraries are intended to be compared simultaneously, binding of each UDE to a binding partner is preferably carried out prior to hybridization of the RNA to an array of target elements such that each library is differentially labeled. Although comparisons are typically carried out between two libraries, any number of comparisons can be made simultaneously as long as each library is capable of generating a signal that can be distinguished from the other libraries. On the other hand, rather than simultaneous hybridization and detection, the arrays can be used in a parallel or sequential fashion. In this format, hybridization and detection is carried out separately for each library and the analysis of the results is compared afterwards relative to normalized controls of steady state genes.

In another aspect of the present invention, UDTs or UDEs are artificially incorporated into the diverse nucleic acids of the library. Enzymes that find particular use with RNA analytes may comprise but not be limited to Poly A polymerase which specifically adds Adenine ribonucleotides to the 3' end of RNA and RNA ligase which can add an oligonucleotide or polynucleotide to either the 5' or 3' end of an RNA analyte. By these means, either homopolymeric or unique sequences can be added to serve as UDTs or UDEs. Enzymes that find particular use with DNA analytes may comprise but not be limited to Terminal Transferase for addition to 3' ends and DNA ligase for addition to either 3' or 5' ends. The sequences that are introduced into the nucleic acid analytes can be labeled during synthesis or addition of a UDE or conversely unlabeled UDTs can be synthesized or added that are detected later by corresponding labeled UDEs. This aspect enjoys special utility when unspliced RNA, snRNA, or rRNA are used as analytes since they may be lacking inherent elements that are present in mRNA that have previously cited as being useful as UDTs. This aspect of the present invention will also find use with procaryotic mRNA since the poly A additions, 5' caps and splicing elements which have been previously cited as potential UDTs of mRNA are intrinsically lacking in procaryotes.

This particular aspect of the present invention may also be used in conjunction with fragmentation processes. For instance, mRNA molecules from eucaryotic organisms can be very large even after processing events have taken place. This size factor can hinder hybridization or allow scissions between the segment used for binding to a target element in the array and the UDT that is being used for signal generation. Additionally, a fragmentation step may also reduce the amount of secondary structure present in RNA. Therefore, in this aspect of the present invention, RNA can be fragmented into smaller sized pieces either by physical or enzymatic followed by addition of sequences that can act as UDTs or UDEs. Examples of physical means for fragmentation of nucleic acids can include but not be limited to shearing or alkali treatment. Examples of enzymatic means can include but not be limited to a partial nuclease or RNase digestion.

In addition, DNA from most sources will also be extremely large in its native form. DNA analytes may also be fragmented by suitable physical or enzymatic means. A particularly useful enzymatic means would be the use of restriction enzymes where the nature of the recognition sequence for the restriction enzyme will determine the average size of the fragments. Also, although most restriction enzymes require double-stranded DNA as templates, some enzymes such as Hha I, Hin P1 I and MnI I cleave single-stranded DNA efficiently (2000-2001 catalog, New England BioLabs, Beverly, Mass., p 214). By this fragmentation method a single analyte molecule is converted into multiple subfragments that can each have their own artificially introduced UDT or UDE. An exemplary illustration of this particular aspect of the present invention is included in FIG. 2.

In another aspect of the present invention, the diverse nucleic acids in a library are used as templates for synthesis of complementary nucleic acid copies instead of using the analytes directly for array analysis. The analyte templates may have intrinsic UDTs present or they may have UDTs artificially incorporated by the means cited earlier. On the other hand, the UDTs do not have to be present in the analyte templates and incorporation of artificial UDTs can take place either during or after synthesis of nucleic acid copies. Examples of enzymes that may be used for making copies of DNA templates can comprise but not be limited to DNA polymerases for synthesis of DNA copies and RNA polymerases for the synthesis of RNA copies. Examples of DNA polymerases that may have use in the present invention for synthesis of DNA copies from DNA templates can include but not be limited to *E. coli* DNA Pol I, the Klenow fragment of *E. coli* DNA Pol I, Bst DNA polymerase, Bca DNA polymerase, Taq DNA polymerase, Tth DNA polymerase, T4 DNA polymerase, T7 DNA polymerase, ALV Reverse Transcriptase, RSV Reverse Transcriptase, HIV-1 Reverse Transcriptase, HIV-2 Reverse Transcriptase, Sensiscript, Omniscript and various mutated or otherwise altered forms of the foregoing. Examples of RNA polymerases that may have use in the present invention for synthesis of RNA copies from DNA templates can include but not be limited to bacteriophage T3 RNA polymerase, bacteriophage T7 RNA polymerase and bacteriophage SP6 RNA polymerase. Examples of enzymes that may have use in the present invention for making DNA copies of RNA templates can comprise but not be limited to ALV Reverse Transcriptase, RSV Reverse Transcriptase, HIV-1 Reverse Transcriptase, HIV-2 Reverse Transcriptase, Sensiscript, Omniscript, Bst DNA polymerase, Bca DNA polymerase, Tth DNA polymerase and various mutated or otherwise altered forms of the foregoing.

Examples of enzymes that may have use in the present invention for making RNA copies of RNA templates can comprise but not be RNA dependent RNA polymerases (Koonin, 1991 J. Gen Virol. 72; 2197-2206, incorporated herein by reference).

Efficient synthesis of complementary copies of analyte templates require the presence of a promoter for efficient synthesis by DNA dependent RNA polymerases while the other cited exemplary enzymes require primers. Incorporation of a UDT into a DNA analyte that will be transcribed by a DNA dependent RNA polymerase can comprise but not be limited to ligation of a UDT sequence and a promoter sequence by the action of DNA ligase. This process is depicted below:

DNA analyte+UDT-Promoter=DNA Analyte-UDT-Promoter

Transcription of this construct would then be capable of production of RNA with the structure: 3' analyte-UDT 5':

One means of carrying out this particular aspect of the present invention is digestion of a library of diverse double-stranded DNA analytes by a restriction enzyme followed by ligation of a double-stranded DNA segment comprising an RNA promoter sequence. Subsequent transcription of the transcription units can synthesize either labeled or unlabeled transcripts. The unlabeled transcripts can be detected by the presence of either inherent or synthetically added UDTs.

When primers are used for synthesis of complementary copies of analyte templates, the primers can comprise random sequences or selected sequences for binding to the analyte templates. Random primers that have commonly been used for priming events have ranged from hexamers to dodecamers. Selected sequences that are useful as primers can be complementary to inherent sequences or to non-inherent sequences that have been introduced into the analyte templates. Examples of inherent sequences can include but not be limited to consensus sequences or homopolymeric sequences. Consensus sequences can be derived from elements that are retained in a large portion of the population being studied. Examples of these could comprise but not be limited to poly A addition sites, splicing elements and multicopy repeats such as Alu sequences. An example of inherent homopolymeric sequences used for primer binding can be the poly A tail that is intrinsic to mature mRNA in eucaryotes. Non-inherent homopolymeric or unique sequences that can be used for primer binding may be introduced into RNA templates by means that can include but not be limited to poly A polymerase or RNA ligase. Non-inherent homopolymeric or unique sequences that can be used for primer binding may be introduced into DNA templates by means that can include but not be limited to Terminal Transferase and DNA ligase. The artificial binding sites can be introduced into intact nucleic acid templates or fragmentation processes may be carried out as described previously.

When homopolymeric or conserved sequences are used as primer binding sites, the library can be subdivided by the use of primers that have been synthesized with 1 or more additional discrete bases at the 3' end. For example, an oligonucleotide primer that has the formula 5'-$T_n$dC-3' would preferentially prime mRNAs whose last base was a G before the poly A tail rather than priming the entire population of mRNA's with poly A tails. The same principle would also hold true when either 5'-$T_n$dG-3' or 5'-$T_n$dA-3' primers are used. This would provide three separate subpopulations of copies of the original mRNA population that in toto should encompass the entire RNA population with poly A tails. This population could be further divided by inclusion of a $2^{nd}$ discrete base at the 3' end of the primers. In this case, oligonucleotides would have either dC, dG, dA or dT as the last base at the 3' end and dC, dG or dA in the penultimate position and the remaining portion comprising a poly T segment. This would create the potential for 12 separate pools from the original population. Further provision of discrete bases at the $3^{rd}$ nucleotide position from the 3' end would provide a separation into 48 different subpopulations if desired and so on.

The use of subpopulations may have utility in providing RNA with lower complexity thereby simplifying analysis later on. In addition, the use of discrete bases at the 3' end would limit the size of poly T tails at the end of the cDNA copies since significant amounts of priming events will only take place at the junction of the poly A addition site. This may reduce background hybridization caused by extensive polyT or PolyA tracts. Also it may increase yields of labeled products by decreasing stalling or premature terminations caused by long homopolymeric tracts. On the other hand, the use of a mixture of oligo T primers with discrete bases at the 3' end would be similar to a completely homopolymeric oligo T primer in being able to synthesize a complete representation of the original analyte sequences while at the same retaining the ability to constrain the size of homopolymeric tails.

In this particular aspect of the present invention, the cDNA molecules synthesized from the pool of RNA templates also comprise UDTs or UDEs. As described previously, these UDTs can be inherently present or they may be non-inherent sequences that are artificially incorporated during synthesis of cDNA. When an analyte has a nucleic acid sequence that can be used as a UDT, synthesis of the complementary copy creates a sequence that can also be used as a UDT. For example, the poly A sequence at the 3' end of eucaryotic mRNA was previously described as a potential UDT. When this mRNA is used as a template by extension of a poly T primer with or without additional bases, the poly T segment of the cDNA copy can function as a UDT. The destruction or separation of the RNA templates from the cDNA would allow the poly T at the 5' end of the cDNA to act as a UDT by binding of a labeled poly A UDE. UDTs or UDEs can also be incorporated into cDNA copies by inclusion of nucleic acid segments that don't participate in primer binding into the 5' tails of either random, homopolymeric, or specific sequence primers. The particular sequence of the additional nucleic acid segments used as UDTs are of arbitrary nature since they aren't needed for primer binding. As such, the choice of sequence for these UDTs can range in complexity from homopolymeric sequences to specific unique sequences. Their nature is also arbitrary, and either the primer or the UDT can comprise PNA's or other nucleic acid homologues. In addition, they may be other polymeric entities besides nucleic acids that provide recognition for UDEs.

Since the nature of the UDT or UDE can be selected by the user, the present invention allows simple differentiation between libraries that are being compared. For instance, one population that is being studied can be extended by homopolymeric or random primers and hybridized with a UDE labeled with Cy 3. A second population that is being compared can be extended by homopolymeric or random primers and hybridized with UDEs that have Cy 5 incorporated into them. The other end of the cDNA is also available for use with UDEs. For example, after synthesis of cDNA copies by reverse transcriptase, the 3' ends can be extended further by the non-template directed addition of nucleotides by Terminal Transferase. An illustration of this particular aspect of the present invention is included in FIG. 3.

Detection of the presence of UDTs or UDEs in the library or libraries of various nucleic acids can be carried out by any of the means that have been described previously for UDTs.

If only a single library is being analyzed, binding of a probe or antibody to a 5' or 3' UDT or UDE may take place before or after hybridization of nucleic acids to the detection elements of the array. The particular order of events will depend upon the nature and stability of the binding partners. On the other hand, when each population incorporates a different UDT or UDE, binding of labeled moieties to the UDTs can take place either before or after hybridization of the copies of the analyte to an array. However, as described previously, the same UDT or UDE can be used for each population if parallel or sequential hybridizations are carried out.

It is also contemplated that the various aspects of the present invention can be used to augment rather than substitute for other previously disclosed methods. For instance, signal can be generated in cDNA copies by a labeled primer being extended in the presence of labeled nucleotides. The signal generated by such a method would be a summation of the signal generated by the original primer and whatever labeled nucleotides were incorporated during strand extension. Thus, a combination of methodologies would generate a signal that would be higher than the amount that would be achieved by either method alone. In addition to a pre-labeled primer, the other methods that are disclosed in the present invention can also be used in various combinations.

There may be situations where amplification of sequences in a sample is advantageous. Therefore, in another aspect of the present invention, multiple cycles of synthesis can be carried out to generate linear amplification of a library of diverse nucleic acid sequences. In the first step of this particular aspect of the present invention, the entire population or a subset of the population of nucleic acids analytes is used to synthesize $1^{st}$ strand nucleic acid copies. Whether the initial analyte is DNA or RNA, in the context of the present invention, this product is considered to be a cNA since it represents a nucleic acid copy of the analyte. Synthesis of the $1^{st}$ strand nucleic acid copies can be carried out as described previously by using discrete primers, random primers, homopolymers, or homopolymers with one or more discrete bases at their 3' ends. In this particular embodiment of the present invention, priming with homopolymers with one or more discrete bases at their 3' ends may also increase the efficiency of amplification since resources such as primers and substrates will be directed only towards amplification of a discrete subpopulation derived from the $1^{st}$ cNA synthesis reaction.

For linear amplification, a primer binding site on a nucleic acid analyte is used multiple times by separation of a $1^{st}$ cNA copy from its template followed by reinitiation of a new $1^{st}$ cNA copy. Separation can be carried out by exposure of the reaction mix to high temperature. If the enzyme used for nucleic acid synthesis is Taq polymerase, Tth polymerase or some other heat stable polymerase the multiple reactions can be carried out by thermocycling of the reaction without the addition of any other reactions. On the other hand, if high denaturation temperatures are used in conjunction with enzymes that are heat labile, for instance Bst DNA polymerase, Klenow fragment of Pol I or MuLV Reverse Transcriptase, irreversible heat inactivation of the enzyme takes place and the enzyme has to be replenished for further rounds of cNA synthesis. Alternatively, methods have been disclosed by Fuller in U.S. Pat. No. 5,432,065 and by Lakobashvill and Lapidot, 1999 (Nucleic Acids Research 27; 1566-1568) for reagents that allow low temperature denaturation of nucleic acids for use with PCR, both of which methods are incorporated by reference. Furthermore, Winhoven and Rossau have disclosed in PCT Application WO 98/45474 (also incorporated by reference) that temperature manipulation can be avoided completely by electrically controlled manipulation of divalent ion levels. Thus by these methods even thermo-labile enzymes can carry out multiple cycles of synthesis for linear amplification. Both above-cited patent documents and the above-cited publication are incorporated herein by reference.

Amplification is a significant aspect of this invention. Several compositions and processes are devoted and directed to amplification. For example, provided herein is a composition of matter comprising a library of double-stranded nucleic acids substantially incapable of in vivo replication and free of non-inherent homopolymeric sequences, the nucleic acids comprising sequences complementary or identical in part or whole to inherent sequences of a library obtained from a sample, wherein the double-stranded nucleic acids comprise at least one inherent universal detection target (UDT) proximate to one end of the double strand and at least one non-inherent production center proximate to the other end of the double strand. The sample from which the inherent sequences of the library are obtained can comprise biological sources, e.g., organs, tissues and cells. As described elsewhere herein, the library of nucleic acids can be derived from genomic DNA, episomal DNA, unspliced RNA, mRNA, rRNA, snRNA and a combination of any of the foregoing. Inherent UDTs can be selected from the group consisting of 3' polyA segments, consensus sequences, or both. As already described above, consensus sequences can be selected from the group consisting of signal sequences for poly A addition, splicing elements, multicopy repeats, and a combination of any of the foregoing. Of special mention is the production center which can be selected from the group consisting of primer binding sites, RNA promoters, or a combination of both. Such RNA promoters can comprise phage promoters, e.g., T3, T7 and SP6.

Another composition of matter for amplification purposes comprises a library of double-stranded nucleic acids substantially incapable of in vivo replication, such nucleic acids comprising sequences complementary or identical in part or whole to inherent sequences of a library obtained from a sample, wherein the double-stranded nucleic acids comprise at least four (4) non-inherent nucleotides proximate to one end of the double strand and a non-inherent production center proximate to the other end of the double strand. Descriptions for such elements, i.e., the sample, the library of nucleic acids, inherent UDTs, non-inherent nucleotides, non-inherent production centers, e.g., RNA promoters, e.g., phage promoters (T3, T7 and SP6) are given elsewhere in this disclosure and are equally applicable to this last composition.

Another composition of matter for amplification comprises a library of double-stranded nucleic acids fixed to a solid support, those nucleic acids comprising sequences complementary or identical in part or whole to inherent sequences of a library obtained from a sample and the nucleic acids further comprising at least one first sequence segment of non-inherent nucleotides proximate to one end of the double strand and at least one second sequence segment proximate to the other end of the double strand, the second sequence segment comprising at least one production center. Of special mention is the use of beads as the solid support, particularly beads and magnetic beads. Other elements, such as the sample and biological sources, the library of nucleic acids, inherent UDTs, non-inherent production centers, have already been described.

Yet another amplification type composition of matter comprises a library of double-stranded nucleic acids attached to a solid support, the nucleic acids comprising sequences complementary or identical in part or whole to inherent sequences of a library obtained from a sample, wherein the double-stranded nucleic acids comprise at least one inherent universal detection target (UDT) proximate to one end of the double strand and at least one non-inherent production center proximate to the other end of the double strand. The elements and subelements (solid support, beads, magnetic beads, sample, library of nucleic acids, inherent UDTs, consensus sequences, production centers, RNA promoters, phage promoters, e.g., T3, T7 and SP6, have been described above.

Among useful processes for detecting or quantifying more than one nucleic acid of interest in a library, one such process of the present invention comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, the polymerizing means comprising a first set of primers and a second set of primers, wherein the second set of primers comprises at least two segments, the first segment at the 3' end comprising random sequences, and the second segment comprising at least one production center; (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) contacting the extended first copies with the second set of primers to form more than one second bound entity; e) extending the bound second set of primers by means of template sequences provided by the extended first copies to form more than one complex comprising extended first copies and extended second set of primers; f) synthesizing from a production center in the second set of primers in the complexes one or more nucleic acid copies under isothermal or isostatic conditions; g) hybridizing any nucleic acid copies formed in step f) to the array of nucleic acids provided in step a) (i); and h) detecting or quantifying any of the hybridized copies obtained in step g). Elements recited in the process just above and their subelements have already been described in this disclosure. Of special mention is the first set of primers which are complementary to inherent UDTs. Further mention should be made that the hybridized nucleic acids can comprise one or more signaling entities attached or incorporated thereto. As described variously above, signal detection can be carried out directly or indirectly. Mention is also made that the process can further comprise the step of separating the first copies obtained from step c) from their templates and repeating step b). Other steps can also be included such as the step of separating the extended second set of primers obtained from step f) from their templates and repeating step e). Step g) can also be carried out repeatedly, a feature provided by this invention and this last-described process. Further, means for synthesizing nucleic acid copies under isothermal or isostatic conditions is carried out by one or more members selected from the group consisting of RNA transcription, strand displacement amplification and secondary structure amplification. These are all contemplated for use of this process.

Another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers comprise at least one production center; and (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) extending the first copies by means of at least four (4) or more non-inherent homopolymeric nucleotides; e) contacting the extended first copies with the second set of primers to form more than one second bound entity; f) extending the bound second set of primers by means of template sequences provided by the extended first copies to form more than one complex comprising extended first copies and extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h). Of special mention is the use or addition of terminal transferase in or after extending step d) wherein the four or more non-inherent homopolymeric nucleotides are themselves added. Elements and subelements of this process are described above. Special mention is made of certain aspects of this process. For example, means for synthesizing nucleic acid copies under isothermal or isostatic conditions can be carried out by one or more members selected from the group consisting of RNA transcription, strand displacement amplification and secondary structure amplification. Moreover, the step of separating the first copies obtained from step c) from their templates and repeating step b) can be added to this process. Moreover, the extended second set of primers obtained from step f) can be separated from their templates and then step e) can be repeated as necessary or desired. In fact, step g) can be repeated as often as desired or deemed necessary.

A process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h). Aspects of this process, including the nucleic acid array, modifications, solid support, fixation/immobilization, nucleic acid analytes, UDTs, production centers, signal generation, polymerizing means, additional steps and repeating steps, synthesizing means, and so forth, have been described above and apply equally to this last-mentioned process. Of special mention are the above-recited ligating means which can comprise, for example, T4 DNA ligase.

Another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the second set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h). Each of the above-recited elements in this process have been described elsewhere in this disclosure. Such descriptions are equally applicable to this process. Of special mention is the process wherein the first set of primers comprise one or more sequences which are complementary to inherent UDTs. The hybridized nucleic acid copies can further comprise one or more signaling entities attached or incorporate thereto. If so, previously described embodiments for signal generation and detection, e.g., direct and indirect generation and detection, are applicable to this process. As described previously for other similar processes, additional steps can be carried out. For example, the step of separating the first copies obtained from step c) from their templates and then repeating step b) can be carried out. A further step of separating the extended second set of primers obtained from step f) from their templates and then repeating step e) can be carried out. Also, step g) can be carried out repeatedly.

Another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers, a second set of primers and a third set of primers wherein the third set comprises at least one production center; and b) contacting the library of nucleic acid analytes with the first set of primers to form a first set of bound primers; c) extending the first set of bound primers by means of template sequences provided by the nucleic acid analytes to form first copies of the analytes; d) contacting the extended first copies with the second set of primers to form a second set of bound primers; e) extending the second set of bound primers by means of template sequences provided by the extended first copies to form second copies of the nucleic acid analytes; f) contacting the second copies with the third set of primers to form more than one third bound entity to form a third set of bound primers; g) extending the third set of bound primers by means of template sequences provided by the extended second set of primers to form a hybrid comprising a second copy, a third copy and at least one production center; h) synthesizing from the production center in the second set of primers in the complexes one or more nucleic acid copies under isothermal or isostatic conditions; i) hybridizing the nucleic acid copies formed in step i) to the array of nucleic acids provided in step a) (i); and j) detecting or quantifying any of the hybridized copies obtained in step i). Elements recited in this process and variations and subelements are as described elsewhere in this disclosure. Of special mention is the use of random primers as the second set of primers. Furthermore, the second set of primers can be complementary to the primer binding site where the process comprises an additional step c') of including a primer binding site after carrying out step c). The primer binding site can be added by means of T4 DNA ligase or terminal transferase. Other aspects or variations of this process can be made or carried out. The further step of separating the extended second set of primers obtained from step f) from their templates and then repeating step e) can be made. Step g) can also be carried out repeatedly. An additional step f) of separating the extended second set of primers obtained in step e) can be carried out. Also, the step of separating the first copies obtained from step c) from their templates and then repeating step b) can be carried out. Further, the step of separating the extended second set of primers obtained from step f) from their templates and then repeating step e) can be carried out. Step g) can also be carried out repeatedly. In another variation of this process, the second set of primers can comprise at least one production center which differs in nucleotide sequence from the production center in the third set of primers.

Still another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers and a second set of primers, wherein the first set of primers are fixed or immobilized to a solid support, and wherein the second set of primers comprises at least two segments, the first segment at the 3' end comprising random sequences, and the second segment comprising at least one production center; (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) contacting the extended first copies with the second set of primers to form more than one second bound entity; e) extending the bound second set of primers by means of template sequences provided by the extended first copies to form more than one complex comprising extended first copies and extended second set of primers; f) synthesizing from a production center in the second set of primers in the complexes one or more nucleic acid copies under isothermal or isostatic conditions; g) hybridizing the nucleic acid copies formed in step f) to the array of nucleic acids provided in step a) (i); and h) detecting or quantifying any of the hybridized copies obtained in step g). The above-recited elements and variations and subelements thereof have been described elsewhere and previously in this disclosure. Those descriptions apply equally to this process.

Another significant process worth discussion is one for detecting or quantifying more than one nucleic acid of interest in a library. This process comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers are fixed or immobilized to a solid support, and wherein the first set of primers comprise at least one production center; and (iv) means for synthesizing nucleic acid copies under isothermal or isostatic conditions; b) contacting the library of nucleic acid analytes with the first set of primers to form more than one first bound entity; c) extending the bound first set of primers by means of template sequences provided by the nucleic acid analytes to form first copies of the analytes; d) extending the first copies by means of at least four (4) or more non-inherent homopolymeric nucleotides; e) contacting the extended first copies with the second set of primers to form more than one second bound entity; f) extending the bound second set of primers by means of template sequences provided by the extended first copies to form more than one complex comprising extended first copies and extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h). The elements recited above in this process and variations and subelements are described elsewhere in this disclosure. Those descriptions apply to this process.

Another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers are fixed or immobilized to a solid support, and wherein the first set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h). Descriptions for any of the above-recited elements in this process are given elsewhere in this disclosure, and need not be repeated except to say that such are equally applicable to this process.

Another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers, wherein the first set of primers are fixed or immobilized to a solid support, and wherein the second set comprises at least one production center; (iv) a set of oligonucleotides or polynucleotides complementary to at least one segment or sequence of the second set of primers; and (v) means for ligating the set of oligonucleotides or polynucleotides (iv); b) contacting the library of nucleic acid analytes with the first set of primers to form more than one first bound entity; c) extending the bound first set of primers by means of template sequences provided by the nucleic acid analytes to form first copies of the analytes; d) ligating the set of oligonucleotides or polynucleotides a) (iv) to the 3' end of the first copies formed in step c) to form more than one ligated product; e) contacting the ligated product with the second set of primers to form more than one second bound entity; f) extending the bound second set of primers by means of template sequences provided by the ligated products formed in step d) to form more than one complex comprising the ligated products and the extended second set of primers; g) synthesizing from a production center in the second set of primers in the complexes one or more nucleic acid copies under isothermal or isostatic conditions; h) hybridizing the nucleic acid copies formed in step g) to the array of nucleic acids provided in step a) (i); and i) detecting or quantifying any of the hybridized copies obtained in step h). For a description of the elements recited in this process, refer to any of the several preceding paragraphs.

Another process for detecting or quantifying more than one nucleic acid of interest in a library comprises the steps of a) providing (i) an array of fixed or immobilized nucleic acids identical or complementary in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers, a second set of primers and a third set of primers, wherein the first set of primers are fixed or immobilized to a solid support, and wherein the third set comprises at least one production center; and b) contacting the library of nucleic acid analytes with the first set of primers to form more than one first bound entity; c) extending the bound first set of primers by means of template sequences provided by the nucleic acid analytes to form first copies of the analytes; d) contacting the extended first copies with the second set of primers to form more than one second bound entity; e) extending the bound second set of primers by means of template sequences provided by the extended first copies to form an extended second set of primers; f) separating the extended second set of primers obtained in step e); g) contacting the extended second set of primers with the third set of primers to form more than one third bound entity; h) extending the third bound entity by means of template sequences provided by the extended second set of primers to form more than one complex comprising the extended third bound entity and the extended set of primers; i) synthesizing from a production center in the second set of primers in the complexes one or more nucleic acid copies under isothermal or isostatic conditions; j) hybridizing the nucleic acid copies formed in step i) to the array of nucleic acids provided in step a) (i); and k) detecting or quantifying any of the hybridized copies obtained in step j). See this disclosure for a discussion of any of the above-recited elements.

Another process for detecting or quantifying more than one nucleic acid of interest in a library comprises the steps of a) providing (i) an array of fixed or immobilized nucleic acids identical in part or whole to sequences of the nucleic acids of interest; (ii) a library of nucleic acid analytes which may contain the nucleic acids of interest sought to be detected or quantified; and (iii) polymerizing means for synthesizing nucleic acid copies of the nucleic acid analytes, such polymerizing means comprising a first set of primers; b) contacting the nucleic acid analytes with the first set of primers to form a first bound entity; c) extending the bound set of first set of primers by means of template sequences provided by the nucleic acid analytes to form first nucleic acid copies of the analytes; d) separating the first nucleic acid copies from the analytes; e) repeating steps b), c) and d) until a desirable amount of first nucleic acid copies have been synthesized; f) hybridizing the nucleic acid copies formed in step e) to the array of nucleic acids provided in step (i); and g) detecting or quantifying any of the hybridized first nucleic acid copies obtained in step f). These elements are described elsewhere in this disclosure.

Another process for detecting or quantifying more than one nucleic acid of interest in a library comprises the steps of a) providing (i) an array of fixed or immobilized nucleic acids identical in part or whole to sequences of the nucleic acids of interest; (ii) a library of nucleic acid analytes which may contain the nucleic acids of interest sought to be detected or quantified; (iii) polymerizing means for synthesizing nucleic acid copies of the nucleic acid analytes, such polymerizing means comprising a first set of primers and a second set of primers; (iv) means for addition of sequences to the 3' end of nucleic acids; b) contacting the nucleic acid analytes with the first set of primer to form a first bound entity; c) extending the bound set of first set of primers by means of template sequences provided by the nucleic acid analytes to form first nucleic acid copies of the analytes; d) extending the first nucleic copies by the addition of non-template derived sequences to the 3' end of the first nucleic acid copies; e) contacting the extended first nucleic acid copies with the second set of primers to form a second bound entity; f) extending the bound set of second set of primers by means of template sequences provided by the extended first nucleic acid copies to form second nucleic acid copies; g) separating the second nucleic acid copies from the extended first nucleic acid copies; h) repeating steps e), f) and g) until a desirable amount of second nucleic acid copies have been synthesized; i) hybridizing the second nucleic acid copies formed in step h) to the array of nucleic acids provided in step (i); and j) detecting or quantifying any of the hybridized second nucleic acid copies obtained in step i). Descriptions for any of the above-recited elements are provided elsewhere in this disclosure.

An illustrative example of this aspect of the present invention would be to bind a poly T primer to poly A mRNA and extend it by Tth DNA polymerase under conditions that allow it to be used as a Reverse Transcriptase. Thermal denaturation followed by binding of an unextended poly T primer would allow synthesis of another copy by Tth DNA Polymerase. The amount of amplification would be proportional to a) the number of primer binding sites on an individual template molecule b) the efficiency of binding/extension and c) the number of cycles carried out. Thus, with a single primer binding site in a target analyte, 50% efficiency and 100 cycles denaturation/repriming, the method of the present invention can produce 50 $1^{st}$ cNA copies from a single analyte molecule.

In another aspect of the present invention, primers are used to generate a library of nucleic acids with production centers capable of synthesizing multiple nucleic acid copies that comprise sequences that are either identical or complimentary to sequences in the original analytes. In the first step of this particular aspect of the present invention, the entire population or a subset of the population of nucleic acids analytes is used to synthesize $1^{st}$ strand nucleic acid copies as described previously for linear amplification. In the next step of this aspect of the present invention, the $1^{st}$ cNA strand is made available for further binding/extension events by the removal or destruction of the template strands. This can be carried out by a variety of physical, chemical and enzymatic means. Examples of such methods can consist of but not be limited to denaturation, alkali or RNase treatments. Denaturation can be carried out by exposure to high heat or by the other methods described above for multiple cycles of linear amplification, thereby allowing them to participate in later steps. In the next step, primers are annealed to the $1^{st}$ cNA strand in order to synthesize the complementary strands, thereby generating double-stranded cNA copies of the original analyte population. The primers used for 2$^{nd}$ strand synthesis are designed such that their 5' ends comprise sequences capable of acting as production centers. A description of such production centers is disclosed in Rabbani et al., U.S. patent application Ser. No. 08/574,443, filed on Dec. 15, 1995 (Novel Property Effecting And/Or Property Exhibiting Compositions for Therapeutic and Diagnostic Uses), abandoned in favor of U.S. patent application Ser. No. 08/978,632, filed on Nov. 25, 1997), incorporated herein by reference. An example of a production center that would be particularly useful in the present invention would comprise an RNA promoter segment.

For example, random hexamer primers for 2$^{nd}$ strand synthesis can have the structure:

5'-promoter-$N_1N_2N_3N_4N_5N_6$-3'

In a preferred mode, the promoter is a phage promoter. The sequences specific for their cognate polymerases are sufficiently short that their addition onto an oligonucleotide being used for priming allows synthesis to remain both efficient and inexpensive. At the same time, they are sufficiently long that they are unique compared to the genomic DNA they are being used with. Also, the phage RNA polymerases that recognize these promoters are usually single protein molecules that have no requirement for other subunits or cofactors. Of special use in this aspect of the present invention are phage promoter sequences that are recognized by the T3, T7 and SP6 RNA polymerases. These enzymes are well characterized and are commercially available from a number of sources.

For efficient functionality, the promoters cited as examples above should be in double-stranded form. This may be carried out in several different ways. A potential sequence of events for one such method is graphically depicted in FIG. 4. If the polymerase used for extension has strand displacement activity, the primer binding closest to the 3' end of the 1$^{st}$ strand (Primer A in FIG. 4) remains bound to the template, but the other extended primers (Primer B and Primer C) are released from the template in single stranded form. Thus, a given individual template molecule may give rise to a plurality of complementary copies by multiple priming/extension events with two groups of products: essentially double-stranded molecules that comprise the 1$^{st}$ cNA strands bound to their complements and single-stranded molecules derived from the displaced strands.

Although initially the displaced strands are in single-stranded form, the continued presence of other primers from either 1$^{st}$ or 2$^{nd}$ strand synthesis could allow further binding/extension events that convert the displaced single strands into double-stranded form. Alternatively, there may have been intermediary purification steps taken to separate extended primers from non-extended primers. For example, separation may be useful to minimize or prevent the synthesis of molecules with promoters at each end. Such double-ended constructs may not transcribe efficiently or may produce nucleic acids that hybridize with each other rather than the target elements of the array. Therefore, the same primers that were used to initiate synthesis of the 1$^{st}$ cNA strand can be added to the mixture with the displaced 2$^{nd}$ cNA strands as well as whatever reagents may also be necessary to convert the displaced single-stranded DNA molecules into double-stranded products. Alternatively, random primers without promoters may be used for priming the displaced 2$^{nd}$ cNA strands. The synthesis of a complementary copy for the displaced single strands also converts the promoter segment in the 5' end of these molecules into double-stranded form.

On the other hand, the promoter in the extended primer that remains bound to the original 1$^{st}$ cNA strand template (Primer A in FIG. 4) needs different processes to render it into a functionally efficient form. For instance, the single-stranded 3' tail of the 1$^{st}$ cNA strand could be digested by the 3' to 5' Exonuclease activity of T4 DNA polymerase. Upon reaching the double stranded portion, the enzyme could then use its polymerase activity to extend the shortened 3' end by using the promoter segment of primer A as a template thereby generating a double-stranded promoter. In another approach, oligonucleotides can be provided that are complementary to the single-stranded promoter sequences (FIG. 5a) or the primers used for 2$^{nd}$ strand cNA synthesis can be designed such that they are self-complementary and form stem loop structures that generate double-stranded functional promoters (FIG. 5b). Lastly, the 2$^{nd}$ cNA strands bound to the template can be denatured and the same processes described above for converting the displaced 2$^{nd}$ cNA strands can be used to convert them into double-stranded form.

The creation of functional transcriptional units from the original diverse nucleic acid analytes allows amplification by making multiple transcript copies from each cNA template. By inclusion of the RNA promoter sequence in primers that used the 1$^{st}$ cNA strand as a template, all the resultant transcripts are also complementary to the 1$^{st}$ cNA strand. However, some target arrays that use defined oligonucleotide sequences as target elements have been designed for the purpose of detecting labeled 1$^{st}$ cDNA copies of mRNA rather than their complements. In such a case, the transcription products of the series of reactions described above can be used as templates to synthesize sequences equivalent to labeled 1$^{st}$ cDNA copies by reverse transcription. As described previously, random or selected primers may find use for this purpose. This conversion step may offer other advantages as well since DNA is known to be more stable than RNA and has relatively less secondary structure compared to RNA.

RNA transcripts or cDNA copies of the RNA transcripts created from the processes described above can either be labeled or unlabeled. When the polynucleotides are unlabeled, they can use UDTs for signal generation. As described previously, the original analytes may have inherent UDT sequences that may serve this function or the analytes may be modified by the incorporation of non-inherent UDT sequences. On the other hand, the synthetic steps that are carried out in the series of reactions above provide the opportunity to incorporate non-inherent UDTs during either 1$^{st}$ strand or 2$^{nd}$ strand synthesis by primers with appropriate designs. For example, a primer design for 2$^{nd}$ strand synthesis can have the following structure:

5' promoter-UDT-hexamer-3'.

After binding the primer above to a 1$^{st}$ cNA strand followed by extension, the transcripts could be generated with the structure:

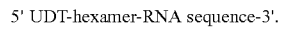
5' UDT-hexamer-RNA sequence-3'.

Although the transcript shown above has a UDT at its 5' end, other designs allow the transcripts to be synthesized with UDTs in their 3' ends. For instance, this can take place by either the sequence of the primer binding site used for the initial 1$^{st}$ strand synthesis being capable of acting as a UDT or by incorporation of a UDT into the primer that is to be used for 1$^{st}$ strand synthesis. As an example of both methods, a transcription unit can be synthesized from poly A RNA by priming of the $1^{st}$ cNA strand with an oligonucleotide primer with the structure:

5' UDT OligoT-3' and priming of the $2^{nd}$ cDNA strand by an oligonucleotide primer having the structure 5' promoter-hexamer-3'.

The double-stranded product of $1^{st}$ cNA and $2^{nd}$ cNA strand synthesis reactions would then have the following structure:

5' promoter-hexamer-$2^{nd}$ strand sequence-PolyA-UDT 3'

Transcription from this construct would generate RNA molecules that have the following structure:

5' hexamer-$2^{nd}$ strand sequence-PolyA-UDT 3'

The product above can bind a UDE either through the an inherent UDT (the Poly A sequence) or through the artificially incorporated UDT. In addition, it should be recognized that the incorporation of UDTs for signal generation can be coupled with incorporation of labeled nucleotides if desired. Thereby, either by direct labeling or by the presence of UDTs, this aspect of the present invention provides for the synthesis of a library of detectable products that will reflect the initial levels of the various nucleic acid analytes of a library.

The use of amplification utilizing RNA synthesis has been previously described by Kwoh and Gingeras, (1989, Proc. Nat. Acad. Sci. USA 86; 1173-1177; incorporated herein by reference) but the purpose of that work was in diametric opposition to the present invention. In Kwoh and Gingeras, primers with specific sequences were used to synthesize the $2^{nd}$ cDNA strand in order to amplify a single defined discrete sequence that was of interest. Thus there is no suggestion or recognition of potential benefits of amplification of a diverse population of various nucleic acids.

In a patent application that was filed in the same year as the publication by Kwoh and Gingeras, a method was described by van Gelder et al. (U.S. Pat. No. 5,716,785; incorporated herein by reference) for linear amplification of a general population of RNA targets by including a phage promoter into the primer used for the $1^{st}$ cDNA strand. Synthesis of the $2^{nd}$ strand were carried out either by nicking of the RNA template by RNase H or by hairpin formation at the end of the $1^{st}$ cDNA strands to provide self-priming events. Furthermore, the claims for this patent and a related patent by the same inventors (U.S. Pat. No. 5,891,636; incorporated herein by reference) specifically includes the phrase "without using an exogenous primer". Thus, in these patents there is firstly a requirement of inclusion of a promoter sequence into the primers used for $1^{st}$ strand synthesis. Secondly there is no appreciation for the use of primers being added to catalyze the $2^{nd}$ strand synthesis. In fact, there is even a teaching away from this latter concept. In addition, all of the foregoing methods synthesize incomplete copies of the primary analytes as the completeness of the copies made by RNase H are dependent upon the distance of the nick that is closest to the 5' end of the mRNA, only a minority will have representation of the sequences closest to the 5' end of the mRNA. In addition, there would never be representation of the end itself since it would be used for retaining the RNA fragment/primer closest to the 5' end. Synthesis by means of hairpin formation also has intrinsically incomplete representation of the 5' end sequences since nuclease degradation of these sequences takes place during elimination of the hairpin. Also, there may be other losses since even nucleases that are considered to be single strand specific are more accurately characterized as having a preference for single-strands since it is well known that there is also some level of activity with segments that are in double-stranded form.

The present invention is in contrast to previously cited art that did not use primers for $2^{nd}$ strand synthesis. These methods of previous art depended upon the presence of RNaseH to create a second strand or else required self-priming events by a foldback mechanism and subsequent treatment with 51 nuclease or its equivalent. In the absence of such a nuclease treatment, transcripts made from hairpin derived constructs would be self-complementary and thus incapable of appreciable hybridization to arrays. In contrast to this prior art, the present invention discloses various methods where exogenous primers are used to synthesize the $2^{nd}$ strand. Also, in some aspects of the present invention, the methods used to synthesize the $2^{nd}$ strand include means that selectively retain information from the 5' ends of analytes. In addition, the present invention describes the potential for the synthesis of multiple transcription units from a single $1^{st}$ strand cNA template thereby providing an additional level of amplification.

It is another aspect of the present invention that the $1^{st}$ cNA strands can be actively prevented from creating $2^{nd}$ cNA strands through a fold-back mechanism by blocking the extendibility of a $1^{st}$ cNA strand. One method of carrying this out is by the addition of a dideoxynucleotide to the 3' terminus of al st cNA copy by terminal transferase. Although this method would prevent a $1^{st}$ cNA strand from participating in self-priming reactions, a blocked $1^{st}$ can strand would retain its capability of being used as a template. In this aspect of the present invention, either the primer used for $1^{st}$ strand cNA synthesis or $2^{nd}$ strand cNA synthesis can comprise an RNA promoter or other replication center.

Another aspect of the present invention discloses the addition or incorporation of artificial primer binding sites to carry out the novel processes described above. For instance, the translation of mRNA into a cDNA copy also frequently includes the terminal addition of a few non-template directed nucleotides into the 3' end of the $1^{st}$ cNA strand by Reverse Transcriptase. In previous art, these added bases have been used as primer binding sites for cloning of full length cDNA molecules. The addition of a few Cytosine nucleotides at the end of a molecule has been sufficient for the binding and extension of a primer that has 3 Guanosine nucleotides at it 3' end (user Manual for SMART cDNA Technology, Clontech Laboratories, Inc., Palo Alto, Calif.). In this system, aborted or stalled cDNA sequences that were incomplete copies of the original mRNA molecules would not be substrates for the addition reaction by Reverse Transcriptase. This provided for a more complete representation of the 5' sequences of the original mRNA in a library of cDNA clones.

The non-template derived addition of Cytosine nucleotides to the $1^{st}$ cDNA strand has been previously used in the process of making a transcription library (Wang et al. 2000, Nature Biotechnology 18; 457-459; incorporated herein by reference). However, this system was basically similar to the method described by van Gelder et al., (op. cit.) since a phage promoter was included in the primers used for synthesis of the $1^{st}$ cDNA strand. As such, this arrangement has the limitation that it has lost the selectivity for molecules that have copied completely their mRNA templates. Primers that bind to interior poly C sequence and initiate extensions are as competent as bindings to poly C's at the end of cDNA (Matz et al., 1999) to synthesize $2^{nd}$ cDNA strands, thereby creating functional double stranded phage promoters.

In contrast to van Gelder et al., and Wang et al., this particular aspect of the present invention provides a promoter in the primer used for the $2^{nd}$ strand synthesis. Thus, the novel processes that have been disclosed previously can be carried out by the use of a primer for $2^{nd}$ strand synthesis that comprises oligo dG sequences at their 3' end for binding to the termini of $1^{st}$ cNA strands. In this aspect of the present invention, priming events that derive from the terminal bindings and extensions will lead to double stranded promoters in molecules. As illustrated in Step (D) in FIG. 6, a primer with a T7 promoter can bind to the terminus of the $1^{st}$ cNA strand. Extension of this primer can create a double stranded molecule where the 3' end of the primer is extended using the cDNA as a template and the 3' end of the cNA is extended using the primer sequences as a template. The net product of such extensions would be a double stranded transcription unit. On the other hand, Step (E) of FIG. 6 shows the binding of a primer with a T7 promoter to an internal segment of the cNA with. In this case, although there can be extension from the 3' end of the primer to create a partially double-stranded molecule, the 3' end of the cNA is unable to use the primer as a template, thus leaving the promoter in a non-functional single-stranded form.

One advantage of the system described above is that the non-template addition of nucleotides can be carried out by enzymes that are already present in the reaction mixture. On the other hand, if desired, Terminal Transferase can be added to increase control over the reaction and improve efficiency. When poly A, T or U sequences are already present in either RNA, DNA or cNA copies, it is preferred that the Terminal transferase use dGTP or dCTP. Primers for $2^{nd}$ strand synthesis can then be designed whose sequences comprise a promoter and a 3' segment complementary to the sequences added by the Terminal Transferase addition step. The steps of this process are shown in FIG. 7, where subsequent extensions to create a double stranded promoter can be carried out as previously described for FIG. 6. Also, since the directed addition of nucleotides takes place only where there is either a double stranded end or a free 3' end, only cDNA molecules that have been completely extended to the ends of the analyte templates will be suitable substrates for terminal addition.

Since these additions can be longer than those derived from non-template additions by Reverse Transcriptase, the primers used for $2^{nd}$ strand synthesis can have longer corresponding homopolymeric segments thereby allowing higher temperatures for binding and extension. This heightened stringency should decrease the frequency of priming events with internal sequences in the $1^{st}$ cNA template strand and provide higher representation of sequences from the 5' end of the original analytes. Therefore, when terminal transferase is used to generate a primer binding site for $2^{nd}$ strand synthesis, the promoter can be in either the $1^{st}$ strand or the $2^{nd}$ strand. The step of terminal transferase addition to the $1^{st}$ cNA can be carried out while it is still bound to its template as described above, or it can be carried out after destruction of the template or separation of the template from the $1^{st}$ cNA strand. This method should continue to enjoy $2^{nd}$ strand synthesis that is preferentially initiated by primers binding and being extended from the 3' termini of $1^{st}$ cNA strands. As described previously, UDTs, as well as labeled or unlabeled nucleotides can all be utilized in carrying out this aspect of the present invention. Also, it is contemplated that higher yields of end products can be achieved by repetitions of one or more steps of the various process that are disclosed herein.

Other means that preferentially carry out priming events at the 3' ends of $1^{st}$ strand cNA's may also find use in the present invention. For instance, a cDNA copy that is a complete copy of its RNA template is a substrate for blunt end ligation by T4 DNA ligase with a double-stranded oligonucleotide. The sequence of the oligonucleotide ligated to the 3' end of the $1^{st}$ cNA strand can be chosen by the user and can function as a primer binding site for making a $2^{nd}$ cNA strand. Similarly a 3' single-stranded tail in the $1^{st}$ cNA strand is a substrate for ligation of a single-stranded DNA oligonucleotide by T4 RNA ligase (Edwards et al., 1991 Nucleic Acids Research 19; 5227-5232; incorporated herein by reference). Lastly, a double-stranded oligonucleotide with a 3' single-stranded tail can be joined to a $1^{st}$ strand cNA through "sticky end" ligation by T4 DNA ligase when the $1^{st}$ cNA and oligonucleotide tails are complementary. As described previously, these cNA tails can be derived from non-template additions by Reverse Transcriptase or by Terminal transferase. Illustrative examples of these processes are given in FIG. 8. Since all of these processes are dependent upon preferential binding of primers to the 3' ends $1^{st}$ strand can molecules, the promoter can be in either the $1^{st}$ or $2^{nd}$ cDNA strand.

In another embodiment of the present invention, a $1^{st}$ strand cNA strand is fragmented by physical, chemical or enzymatic means. Examples of enzymatic means can include but not be limited to restriction enzymes such as Hha I, Hin P1 I and MnI I, DNases such as DNase I and nucleases such as S1 nuclease and Mung Bean Nuclease. These fragments can be used as templates for synthesis of a $2^{nd}$ strand by any of the methods described previously. For example, hybridization and extension of random primers with T7 promoters can be used with the cNA strand fragments as templates in processes similar to those shown in FIGS. 4 and 5. Or if preferred, the homopolymeric addition or ligation steps described above can be carried out to provide specific primer binding sites. FIG. 8 is an illustration of this process using the homopolymeric method. Breaking down the $1^{st}$ strand copy into smaller segments followed by incorporation of a primer during $2^{nd}$ strand synthesis would provide smaller transcription units. This may be advantageous when using modified nucleotides for signal generation. For instance, when there are long stretches in the template strand that are complementary to the labeled nucleotide, the modification to the nucleotide may cause a blockage in downstream transcription or loss of processivity and result in under-representation of those sequences. In this particular aspect of the present invention, the partition of copies of analyte sequences into smaller individual transcription units allows each of the units to direct RNA synthesis independently thereby creating a more complete representation of the library of various nucleic acid sequences.

In another embodiment of the present invention, the novel methods disclosed for synthesis of a library are combined with capture methods to provide more efficient synthesis as well as flexibility in changing salts, buffers, enzymes and other components during multistep processes. The present invention discloses the use of a $1^{st}$ strand primer that is bound to a solid matrix such as a bead followed by the processes described above. For example, the 3' end of Oligo T sequences bound to a solid matrix can be extended using polyA mRNA as a template. In accordance with the methods of the present invention, this $1^{st}$ cNA strand is thereupon used as a template for the $2^{nd}$ cNA strand. When carrying out this aspect of the present invention, a replicative center such as an RNA promoter sequence can be introduced into either the $1^{st}$ or $2^{nd}$ strand depending upon the particular method used. For instance, random primers with promoters in their 5' ends can bind to the extended $1^{st}$ cDNA strands to create $2^{nd}$ strands that have a promoter incorporated into them. This process is depicted in FIG. 10.

The single-stranded promoter on the 5' ends of the $2^{nd}$ cDNA strands can be converted into double-stranded form by any of the methods described previously. For instance, the primer/template complex that remains bound to the bead in FIG. 10 can be treated with T4 DNA polymerase, hybridized with an oligonucleotide complementary to the promoter segment or the primer can be designed with self complementary regions. The latter two methods were previously discussed with reference to FIG. 5. With regard to the displaced $2^{nd}$ cDNA strands in FIG. 10, the presence of unextended oligo-T tails on the matrix material can provide further binding/extension events since the displaced strands carry poly A sequences on their 3' ends. However, if preferred, more oligo-T can be added whether associated with beads or free in solution. Extension of the oligo-T should ultimately result in conversion of the single-stranded promoters of the displaced $2^{nd}$ cDNA strands into functional double-stranded forms.

Another method that can be used in the present invention is to repeat one or more of the steps that have been described in the present invention. For instance, after using a library of analytes to synthesize $1^{st}$ can copies attached to a matrix, the analytes can be separated from the $1^{st}$ cNA copies and used to create another pool of $1^{st}$ cNA copies. Similarly, after synthesis of $2^{nd}$ can strands, the library of $2^{nd}$ cNA strands can be separated from the $1^{st}$ can strands fixed to the matrix. All $2^{nd}$ cNA strands that have copied the 5' ends of the $1^{st}$ cNA strands will have regenerated the sites that were initially used to bind to the primers linked to the beads. If desired, the $2^{nd}$ strands can be rebound to the same beads. Since there are likely to be an enormous number of poly T primers on the beads compared to the number of templates used for $1^{st}$ cNA synthesis, the majority of primers on the matrix remain unextended and can be used for new priming events. Thus, complete copying of these rebound $2^{nd}$ can strands should allow generation of double-strand promoters at the ends of these molecules without a necessity for the use of T4 to do "trimming". If desired the $1^{st}$ cNA strands that are attached to the matrix can be used to generate another pool of $2^{nd}$ cNA strands. The pool or pools of $2^{nd}$ can strands can then be added to fresh beads with primers complementary to their 3' ends. Again, the extension of the primers attached to the matrix will convert all of the $2^{nd}$ can strands into double-stranded form including the promoter sequences that were at their 5' ends. Lastly, after a transcription reaction is carried out, the reaction products can be removed and the nucleic acid on the matrix can be used for more transcription reactions thereby accumulating more transcription products.

Although the example above describes priming of an analyte with a poly A segment by an oligo T primer attached to a matrix, the primers can also be prepared with one or more discrete bases at their 3' ends. As described previously, these primers can be used as a group that represents all the possible variations or they can be used individually depending upon whether general amplification or separation into subclasses was desired. The poly A sequence used above is understood to only be an illustrative example. As described previously, the sequences in analytes used for binding of $1^{st}$ strand primers can be derived from inherent sequences or they may be noninherent sequences in analytes that have been artificially introduced by any of the means that have been described previously. This particular embodiment of the present invention can utilize any of these primer binding sites by appropriate design of the primer sequence bound to the matrix.

In the present invention, the primer sequences for $1^{st}$ strand synthesis can be either directly or indirectly attached to a matrix. Methods for direct attachment of oligonucleotides to matrixes are well known in the art. In addition, beads with covalently attached extendable poly T segments are commercially available from a number of sources. Methods for indirect attachment are also well known in the art. For instance FIG. 11 depicts a sandwich method where a primer has two segments, one of which is complementary to a capture segment attached to the matrix and the other is complementary to the poly A segment of the target RNA. The two segments of the primer may form a continuous nucleotide sequence or there may be a disjunction between the two segments. Hybridization of the two segments of the primer and the complementary sequences on the matrix and the binding site of the analyte can take place simultaneously or they can be carried out in a step-wise fashion. For instance, hybridization of target RNA to the capture element can be carried out in solution followed by capture to the matrix. It is preferred that the segment that is bound to the matrix be rendered incapable of extension. One way this blockage can be carried out is by the use of the 3' end as the attachment point to the matrix as depicted in FIG. 11. Binding and extension events can take place as described previously for FIG. 10 to synthesize $1^{st}$ and $2^{nd}$ cDNA copies of the original poly A mRNA. Conversion of the promoter sequences into double-stranded form can also take place as described above. Transcription can take place either while the transcription units are attached to the matrix or if desired separation from the matrix can take place in a step subsequent to the transcription.

Incorporation of an RNA promoter during $1^{st}$ strand synthesis results in transcripts that comprise sequences that are complementary to sequences in the original analytes. Incorporation of an RNA promoter into the $2^{nd}$ strand synthesis results in the production of transcripts that comprise sequences that are identical to sequences in the original analytes. As described previously, these can easily be converted into complementary cDNA copies if desired.

It is a further subject of the present invention that transcription units can be synthesized without incorporating a promoter sequence into either the $1^{st}$ cNA (as described by Eberwine et al., op. cit.) or the $2^{nd}$ cNA strand (as described in previous embodiments of the present invention). As shown in step D of FIG. 12, when using extended $1^{st}$ cNA strands as templates for synthesis of the $2^{nd}$ cNA strands, a duplicate of the original primer binding sequence is synthesized. Thus, in FIG. 12 a polyA segment is created at the 5' ends for both displaced $2^{nd}$ cNA strands and for $2^{nd}$ cNA strands that remain bound to the beads. After removing these $2^{nd}$ cNA strands, oligonucleotide primers comprising an RNA promoter and oligo-T sequences can be hybridized to the $2^{nd}$ cNA strands. The primers may be attached to a matrix or they may be free in solution. Provision of DNA Polymerase, nucleotides and appropriate cofactors can allow extension of both the 3' ends of the promoter/primers as well as the 3' ends of the cDNA copies thereby creating functional transcriptional units as shown in step F of FIG. 12. Transcription from these DNA molecules will result in products that comprise sequences that are complementary to sequences in the original analytes In previous art the most common use of oligo-T that is attached to a matrix such as cellulose or beads has been for the purpose of a selective isolation of polyA mRNA followed by a release step prior to synthesis of a library. In one instance, a special oligo T primer joined to a T7 promoter was extended using RNA as template to create a library (Eberwine op.cit.). However, this system put the promoter in close proximity to the capture bead, potentially decreasing its ability to be converted into double-stranded form and/or for it to function as a promoter. Also, synthesis of the $2^{nd}$ strand by random priming does not prevent hairpin self-priming. In the absence of a nuclease step, transcription units would direct synthesis of self-complementary RNAs from hairpin template sequences that would be incapable of hybridizing to target arrays. Use of the templates for this non-productive synthesis may cause an inefficiency in the amount of effective labeled transcripts.

A particular benefit of the use of promoters in primers used for $2^{nd}$ cNA synthesis present invention is that although $1^{st}$ cNA strands can be synthesized under conditions that have the potential for self-priming events i.e. creating $2^{nd}$ cDNA strands by a fold-back mechanism, the absence of a promoter in $1^{st}$ cDNA; strand would prevent these constructs from being transcriptionally active. Thus, only $2^{nd}$ cDNA strands that are derived from priming events by oligonucleotides with promoter sequences are functional for transcription. This in contrast to the system previously described by Eberwine (op. cit.). Contrariwise, methods have also been described in the present invention that allow the use of a promoter in the $1^{st}$ strand by either preventing extension of a $1^{st}$ cNA strand or by facilitating $2^{nd}$ strand synthesis from priming events at the ends of $1^{st}$ strand templates.

It is another object of the present invention to provide a method for comparative analysis that requires only a single RNA population to be labeled. This particular aspect takes advantage of competitive binding by an unlabeled population of RNA. Synthesis of this material can take place by any of the means described in the foregoing work. The particular sequences can be homologous to sequences that are present on the arrays or they may be homologous to sequences that are present in the labeled material. By comparison of hybridization of the labeled material in the presence or absence of competitor, relative levels of increased or decreased mRNA synthesis can be established relative to the competitor, ie. differential competition. Adjustments can be made in the relative amounts of unlabeled material being used or the housekeeping genes that are present as controls can allow for normalization values. This method provides the advantage that multiple sequential or parallel hybridizations can be carried out and compared with a single common labeled control population of RNA.

The various steps of the present invention can be carried out sequentially by adding various reagents and incubation steps as required. On the other hand, the series of steps can be segregated by introducing additional steps that either remove or inactivate components of the reaction or where a desired product is separated from a reaction mixture. An example of the former can be heat inactivation of Reverse Transcriptase. An example of the latter can be isolation of RNA/DNA hybrids by selective matrices. These additional steps can be carried out to either improve the efficiency of subsequent steps or for the purpose of preventing undesirable side reactions.

Although the previous examples have disclosed the utility of a phage promoter in carrying out various aspects of the present invention, a production center is able to operate by other means as well. For instance, various means of introducing UDTs that serve as primer binding sites have been previously described in the context of synthesis of $2^{nd}$ copy strands followed by RNA transcription. These primer binding sites can in themselves serve as production centers for multiple copies of various nucleic acids under isothermal conditions.

For instance the use of primers that are designed to create target-dependent stem-loop structures has previously been disclosed in Rabbani et al., U.S. patent application Ser. No. 09/104,067, filed on Jun. 24, 1998 (Novel Processes for Amplifying Nucleic Acid, Post-Termination Labeling Process for Nucleic Acid Sequencing and Producing Nucleic Acid Having Decreased Thermodynamic Stability; for specific isothermal amplification of selected sequences. The content of the aforementioned Ser. No. 09/104,067 is hereby incorporated by reference. In the present invention, UDTs can be added to the various nucleic acids of a library to carry out the amplification disclosed in Rabbani et al., U.S. patent application Ser. No. 09/104,067, cited supra and incorporated herein by reference. FIG. 13 is a depiction of a series of reactions that could be used to carry this out. For instance, a UDT can be ligated to a library of poly A mRNA where the UDT comprises two segments (termed X and Y in this Figure). In the next step, a primer (Primer 1) that comprises two segments, a poly T sequence at the 3' end and a segment termed Z at the 5' end is hybridized to the poly A sequences at the 3' end of the mRNA and extended by reverse transcription to make a $1^{st}$ cNA copy (Steps C and D of FIG. 13) that contains the sequences X' and Y' at the 3' end. Removal of the original template makes the X' segment at the 3' end of the $1^{st}$ cNA copy available for hybridization. A second primer (Primer 2) that has two segments, segment X at the 3' end and segment Y' at the 5' end can be annealed and extended to make a $2^{nd}$ copy (Steps D and E) of FIG. 12. The presence of Primer 2 should also allow a further extension of the $1^{st}$ cNA copy such that a double stranded segment is formed where the Y and Y' segments are capable of self-hybridizing and thereby creating a stem-loop structure with the X and X' segments in the loop portions as described in Rabbani et al., U.S. patent application Ser. No. 09/104,067, cited supra and incorporated herein by reference. Creation of a stem loop at the other end can be carried out by annealing a third primer (Primer 3) which comprises two segments, segment Z at the 3' end and a Poly A segment at the 5' end using a $2^{nd}$ cNA copy as a template. The availability of $2^{nd}$ cNA copies as templates can be derived from multiple priming events by Primer 2 at the other end (as described in Rabbani et al., U.S. patent application Ser. No. 09/104,067, cited supra and incorporated herein by reference, or by denaturation of the $1^{st}$ and $2^{nd}$ strands from each other. Extension of Primer 3 creates a structure that has the Poly T and Poly A segments forming a stem and the Z and Z' segments forming the loops. Further binding and extension reactions under isothermal conditions can proceed as described previously for unique targets. It should be noted that the particular sequences used for X, Y and Z are arbitrary and can be chosen by the user. For instance, if the Z segment of Primer 1 used in step C of FIG. 13 was designed with X and Y sequences at the 5' end, the unit length amplicon would have X' and Y segments at the 3' end of each strand. As such, amplification could be carried out using only Primer 2.

Another example of the use of non-inherent UDTs being used as primer binding sites for isothermal amplification is shown in FIG. 14 for use with the Strand Displacement Amplification system described by Walker et al., in U.S. Pat. No. 5,270,184 herein incorporated by reference. In this particular example, Incorporation of segment X takes place by two different methods. In step B of FIG. 14, segment X is introduced by ligation to an analyte of the library. In step C segment X is attached to a poly T primer and becomes incorporated by strand extension. The presence of the X segment at the 5' end of each end of the amplicon unit allows primer binding by a single Strand Displacement primer. Methods for the designs of primers with appropriate sequences at their 5' ends have been described by Walker et al., (op. cit.). With regard to the particular enzyme being used as part of the SDA system, the presence of a particular restriction site between primer binding sites may limit the ability of some sequences to be amplified in a reaction designed for general amplification of a library. This may be overcome by choosing relatively uncommon sequences or carrying out parallel reaction with different enzymes.

It should be pointed out that in the examples shown in FIGS. 13 and 14, the presence of primer binding sites at each end allows exponential amplification. However, these processes can be changed to linear amplification by designing amplicons that have binding sites for isothermal amplification at only one end of the amplicon.

Incorporation of a primer binding site that can be used for isothermal production of multiple copies can take place by any of the steps described previously that used a promoter in the example. For instance, FIGS. 13 and 14 show addition of an isothermal binding site directly to an analyte and also show incorporation of an isothermal binding site during synthesis of a first copy. FIG. 15 shows a similar situation, but in this example segment X is incorporated during $1^{st}$ cNA synthesis, segment Q is added after first strand synthesis and segment Z is added during $2^{nd}$ cNA strand synthesis. As described previously, one or more of these segment can comprise primer binding sites for isothermal synthesis. It should also be pointed out that in FIGS. 13 through 15 both inherent and non-inherent UDTs were used as part of the examples.

In another aspect of the present invention, UDTs are used as primer binding sites for amplification on an array. In this particular aspect, each locus on an array comprises two sets of primers. The first set of a locus comprises Selective Primer Elements (SPE's) that are specific for a particular analyte. The second set of a locus comprises Universal Primer Elements (UPE's) that are identical or complementary to sequences in UDT elements. As described previously, UDTs can be derived from naturally occurring sequences or they may be artificially incorporated. The SPE's at a locus would be able to bind to the complementary sequences in the nucleic acids of a library, thereby binding discrete species of nucleic acids to that particular locus of the array. The use of appropriate conditions, reagents and enzymes would allow an extension of an SPE using the bound nucleic acid as a template.

As an example of this aspect of the present invention, FIG. 16 depicts an array with three different loci termed Locus P, Locus Q and Locus R. At each of the loci, there is a set of SPE's bound to the array that are complementary to a particular sequence in cDNA copies made from one of three species of poly A mRNA termed P, Q and R respectively. In addition, each locus of the array in FIG. 16 has a set of UPE's that comprises poly T sequences. Synthesis of a cDNA copy of each of the mRNA templates by Poly T priming of their polyA tails creates cDNA P, cDNA Q and cDNA R respectively. Binding of the $1^{st}$ cDNA strand of an analyte to an SPE should be selective for each species at a particular locus. On the other hand, there should be little or no binding of the cDNA copies to the universal Poly T sequences in the UPE's of the array of FIG. 16. The addition of enzymes and reagents for extension should generate $2^{nd}$ cDNA copies of P, Q and R at the LP, LQ and LR sites on the array by extension of SPE's using the bound cDNA as templates. Each of these $2^{nd}$ cDNA copies would comprise unique sequences complementary to the $1^{st}$ cDNA strand templates. However, in addition to these unique sequences, the $2^{nd}$ strand copies would include a common poly A sequence at their 3' ends. At this stage it may be preferable to remove unhybridized analytes as well as templates used for $2^{nd}$ strand synthesis. This is most easily carried out by heat denaturation followed by washing steps. The product at this stage is an array that has extended and un-extended SPE's at each locus where the number of extended SPE's should be in proportion to the amount of the original corresponding analytes. The extended SPE's can now serve as templates when an unextended poly T UPE is in sufficient proximity. The design and placement of pairs of unique primers for solid phase amplification has been previously described in detail in U.S. Pat. No. 5,641,658, hereby incorporated by reference. Methods for synthesis of arrays with two different sequences at each locus has also been described by Gentalen and Ghee, 1999 (Nucl. Acids Res. 27; 1485-1491) incorporated by reference. The same primer design rules may also be applied to the present invention that uses non-unique primers. Extension of a UPE with a nearby extended SPE as a template creates a new template that can in turn be used as a template for a nearby unextended SPE. This process can proceed through a series of binding and extension steps that alternatively using SPE's and UPE's to accumulate nucleic acids that are derived from target nucleic acids homologous to the sequences in the SPE at each locus. An illustration of these steps is given in FIGS. 16 through 19.

Methods for the design and synthesis of arrays for solid phase amplification have been described in U.S. Pat. No. 5,641,658 and Weslin et al., 2000, (Nature Biotechnology 18; 199-204; both documents incorporated herein by reference) for utilization of totally unique sets of primers. Methods of assaying the extent of synthesis are also described in these references. For example, labeled precursors can be included in the reaction to synthesize a labeled amplification product. Alternatively, normal precursors can be used with signal generation provided by intercalating dyes binding to amplification products.

This invention provides unique compositions and processes for solid phase amplification. Among such compositions is one that comprises an array of solid surfaces comprising discrete areas, wherein at least two of the discrete areas each comprises a first set of nucleic acid primers; and a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ from each other by at least one base; and wherein the nucleotide sequences of the second set of nucleic acid primers of a first discrete area and the nucleotide sequences of the second set of nucleic acid primers of a second discrete area are substantially the same or identical. Previous descriptions for any of the above-recited elements have been given elsewhere in this disclosure, and resort may be made to those descriptions in connection with this process.

A related composition of this invention is one comprising an array of solid surfaces comprising a plurality of discrete areas; wherein at least two of the discrete areas each comprises a first set of nucleic acid primers; and a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ substantially from each other; and wherein the nucleotide sequences of the second set of nucleic acid primers of a first discrete area and the nucleotide sequences of the second set of nucleic acid primers of a second discrete area are substantially the same or identical. See this disclosure above and below for a description of any of the elements in this process.

Related to the last-mentioned compositions are processes for producing two or more copies of nucleic acids of interest in a library comprising the steps of a) providing (i) an array of solid surfaces comprising a plurality of discrete areas; wherein at least two of the discrete areas each comprises: (1) a first set of nucleic acid primers; and (2) a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ from each other by at least one base; and wherein the nucleotide sequences of the second set of nucleic acid primers of a first discrete area and the nucleotide sequences of the second set of nucleic acid primers of a second discrete area are substantially the same or identical; (ii) a library of nucleic acid analytes which may contain the nucleic acids of interest; (iii) polymerizing means for synthesizing nucleic acid copies of the nucleic acids of interest; b) contacting a primer of the first set with a complementary sequence in the nucleic acid of interest; c) extending the primer in the first set using the nucleic acid of interest as a template to generate an extended first primer; d) contacting a primer in the second set with a complementary sequence in the extended first primer; e) extending the primer in the second set using the extended first primer as a template to generate an extended second primer; f) contacting a primer in the first set with a complementary sequence in the extended second primer; g) extending the primer in the first set using the extended second primer as a template to generate an extended first primer; and h) repeating steps d) through g) above one or more times. Elements above are described elsewhere herein.

Another related process useful for detecting or quantifying more than one nucleic acid of interest in a library comprises the steps of a) providing (i) an array of solid surfaces comprising a plurality of discrete areas; wherein at least two of such discrete areas each comprises: (1) a first set of nucleic acid primers; and (2) a second set of nucleic acid primers; wherein the nucleotide sequences in the first set of nucleic acid primers are different from the nucleotide sequences in the second set of nucleic acid primers; wherein the nucleotide sequences of a first set of nucleic acid primers of a first discrete area and the nucleotide sequences of a first set of nucleic acid primers of a second discrete area differ from each other by at least one base; and wherein the nucleotide sequences of the second set of nucleic acid primers of a first discrete area and the nucleotide sequences of the second set of nucleic acid primers of a second discrete area are substantially the same or identical; (ii) a library of nucleic acid analytes which may contain the nucleic acids of interest; (iii) polymerizing means for synthesizing nucleic acid copies of the nucleic acids of interest; and (iv) non-radioactive signal generating means capable of being attached to or incorporated into nucleic acids; b) contacting a primer of the first set with a complementary sequence in the nucleic acid of interest; c) extending the primer in the first set using the nucleic acid of interest as a template to generate an extended first primer; d) contacting a primer in the second set with a complementary sequence in the extended first primer; e) extending the primer in the second set using the extended first primer as a template to generate an extended second primer; f) contacting a primer in the first set with a complementary sequence in the extended second primer; g) extending the primer in the first set using the extended second primer as a template to generate an extended first primer; h) repeating steps d) through g) above one or more times; and i) detecting or quantifying by means of the non-radioactive signal generating means attached to or incorporated into any of the extended primers in steps c), e), g), and h). Elements above are described elsewhere herein.

For many uses, the UPE's will be present on the array during hybridization of the analyte to complementary SPE's. However, there may be circumstances where the presence of UPE's in this step may be deleterious. For example, binding of the diverse nucleic acids of a library should preferably take place only through the action of the SPE's on the array. In contrast to the example given above, there may be cases where due either to the nature of the library or the choice of UPE sequences, hybridization can take place between the library and the UPE's of an array. This event could result in a loss of efficiency in the reaction by binding of target nucleic acids to inappropriate areas of the array. For instance, the SPE's at a particular locus would be unable to use complementary nucleic acid targets as a template if these targets are inappropriately bound to another physical location through binding of UPE's. Furthermore, UPE's would be rendered non-functional by being extended and synthesizing nucleic acid copies that lack complementary to the SPE's at that particular locus.

Accordingly, it is a subject of the present invention that UPE's may be either non-functional or absent during the initial hybridization of a library to the SPE's in the array. In one method of carrying this out, advantage is taken of the universal nature of the UPE's. Although each particular species of SPE is relegated to a specific area of the array, the UPE's are intended to be present in multiple areas of the array. As such, an array can be synthesized where each locus comprises a set of SPE's and a set of chemically activated sites that are compatible with reactive groups on UPE's. After the initial hybridization of nucleic acid targets to their appropriate SPE's, the UPE's with appropriate groups can be added universally to the array by a simultaneous attachment to all of the active sites on the array. An example of compatible modifications that could be used in this aspect of the present invention could be arrays that have maleimide groups at each locus and UPE's that have amine groups attached to their 5' ends.

An alternative approach is for synthesize the array with UPE's that have been modified such that they are temporarily unable to function. For example, the UPE's could be synthesized with 3' $PO_4$ groups thereby blocking any potential extension reactions. After hybridization of nucleic acids to the various SPE's of the array followed by extension of SPE's, the nucleic acids used as templates could be removed from the reaction. After this step, the 3' end of the UPE's could be rendered functional by removal of the 3' $PO_4$ groups by treatment with reagents such as bacteriophage polynucleotide kinase or alkaline phosphatase. Thereafter, successive reactions can take place as described previously.

An alternative approach would be the use of hybridization properties of nucleic acids. For example, the Tm of hybridization between nucleic acids is a function of their length and base composition. Therefore, the SPE's and UPE's can be designed with Tm's that are sufficiently different that salt or temperature conditions can be used that selectively allow hybridization of the nucleic acids in the sample to SPE's. The salt and temperature conditions can be altered later to allow hybridization to the UPE's on the array and carry out the appropriate series of reactions.

Another example would be the use of competitive hybridization. Nucleic acids or their analogues can be added that are homologous to the UPE's. By either pre-hybridization or by including a high excess of such competitors, the UPE's should all be occupied with the competitor nucleic acids thereby allowing binding of the nucleic acids of the library to SPE's only. Furthermore, the competitors can be synthesized in such a way that even though they are bound to the UPE's they are unable to serve as templates for extension of the UPEs. Examples of means that can be used for this purpose can include but not be limited to peptide nucleic acids and oligonucleotides with multiple abasic sites. After extension of the SPE's, both the templates used for extension of SPE's and the competitor oligonucleotides bound to the UPE's can be removed concurrently rendering both the extended SPE's and UPE's available for binding to each other.

The poly A RNA in the example shown in FIGS. 16-19 made use of an inherent UDE in eucaryotic mRNA. As described previously, UDEs can also be added artificially either by polymerization or ligation. For instance, a selected arbitrary sequence can be added to the 5' ends of a library of RNA analytes by the action of T4 RNA ligase. An array could then be used that has SPE's for unique RNA sequences and UPE's with the same sequences as the ligated segment. After localization of the various species of RNA to their appropriate location on an array, an enzyme appropriate for reverse transcription can be added as well as the appropriate buffers and reagents to extend the SPE's thereby synthesizing $1^{st}$ strand cDNA copies linked to the array. Removal of the RNA template would then allow the complement of the UPE in the cDNA copy to bind to a nearby UPE on the array followed by a set of reactions as described previously. Since the choice of sequences for artificially added UPE's is of arbitrary nature, this aspect of the present invention can be applied to a simultaneous assay of different pools of analytes by adding different discrete UPE sequences to each library. In contrast to this, the prior art cited above makes no provision for distinguishing between collection of analytes from different sources that have the same sequences. An illustration of an array that could be used for this purpose is given in FIG. 20 where two libraries are being compared. One library has been prepared by joining sequences for UPE 1 to the nucleic acids and a second library has been prepared that has sequences for UPE 2 joined to the nucleic acids. It should be noted that in FIG. 20, Locus 1 of the array has the same SPE's as Locus 9 but they differ in the identity of the UPE where UPE 1 is at Locus 1 and UPE 2 is at locus 9. This is also true for Locus 2 compared to Locus 10 and so on. Thus, binding of the same sequence can take place at either Locus 1 or Locus 9, but the extent of amplification that will take place at each locus will be dependent upon the amount of bound material that contains the appropriate UPE sequence.

In addition, although the examples above have used RNA or cDNA copies as libraries for this aspect of the present invention, it has been previously disclosed that DNA may also be the initial analyte. As an example of this aspect of the present invention, DNA can be digested with a restriction enzyme to create a library of fragments. A double-stranded UDE can then be ligated to these fragments by the action of T4 DNA ligase. The ligated products can then be denatured and hybridized to an array of SPE's. For example, to investigate potential SNP's at a site "X" on a target nucleic acid, sets of SPE's can be designed that differ by a single nucleotide at their 3' ends. The subsequent efficiency of extensions would then be dependent on how well the nucleotide at site "X" of the target template matched the 3' base of the SPE. As an internal control, a set of SPE's can be designed that will utilize each strand at site "X" thereby duplicating the information. This process is illustrated in FIG. 21. In this particular example, it is preferred that binding between the nucleic acid and the UPE on the array be prevented since the ligated fragments will have sequences complementary to the UPE's. Examples of means that can be used to carry this out have been described previously whereby UPE's are absent or non-functional during hybridization of the nucleic acids to the SPE's. On the other hands, the nucleic acids that are being analyzed can be treated such that sequences that are complementary to UPE's are removed. For instance, after the ligation step described above, nucleic acids can be treated with a 3' to 5' double-stranded Exonuclease. This should selectively remove sequences complementary to the UPE's while retaining sequences that are identical to sequences in the UPE's. Regeneration of the sequence complementary to the UPE should then take place only after extension of an SPE. Also as disclosed above, the use of artificial addition of UPE sequences allows the simultaneous analysis of different pools by a selective choice of different UPE sequences for each pool.

It is a further intent of the present invention that rather than choosing specific sequences derived from prior sequence information, a general array can be made that offers complete representation of all possible sequences. For instance, a library of SPE's that are 4 bases in length with permutations of all 4 variable bases would comprise 4×4×4×4 distinct sequences, i.e. a total of 256 permutations. With a complexity of all potential octamer oligonucleotides with the four variable bases, there would be a total of 256×256 for a total of 65,536 permutations. In prior art, an array covering all the possible amplification products would require two unique primers for each individual amplification. Thusly, there would be a requirement for a total of 65,536×65,536 for a total of $4.3 \times 10^9$ permutations for pairs of unique octamer primers on the array. Such high numbers may be too expensive or too complex to have practical application. On the other hand, the present invention overcomes this limitation by virtue of the use of UPE's. Accordingly, only the SPE's need to encompass all the possible octamer sequences which results in a requirement for a total of 65,536 different sequences, a number that is easily within the ability of current technology. The number of different nucleic acid that will be amplified at each locus will depend upon the complexity of the library of nucleic acids applied as templates as well as the conditions used for carrying out amplification. The degree of complexity of the array can also be altered by increasing or decreasing the number of nucleotides comprising the SPE's. Conversely, it has previously been pointed out that a degree of differentiation can be achieved by adding one or more discrete bases to the UPE. For example, the use of a single variable nucleotide at the end of a polyT UPE would decrease the complexity of the analytes in a library that could be amplified since on average, only one out of three of the various diverse nucleic acid analytes bound to SPE's would be able to carry out strand extension. On the other hand, the inclusion of all 3 sets of UPE's that each carries one of the 3 potential bases in combination with complete representation of octamer SPE's would increase the complexity of arrays from 65,536 sequences to a total of $1.97 \times 10^5$ ($3 \times 65,536$) permutations. By using variable nucleotides in the last two nucleotides at the 3' end of the UPE on an array with SPE octamers, the complexity would be $8.0 \times 10^5$ ($12 \times 65,536$) permutations. It also should be understood that the complexity of the array can have an incomplete representation of all potential SPE sequences. For instance, octamers that have Tm's that are much higher or lower than the average Tm of a random population may be not be desired to be present. Also, octamers that have self-complementary 3' and 5' ends may exhibit poor binding ability. When more than one species of UPE is being used, this aspect can be carried out with amplification carried out simultaneously with each UPE. More preferably, reactions are carried out in parallel with a given UPE on an array for each set of reactions.

In another aspect of the present invention, a mixed phase amplification is carried out where SPE's at fixed locations on an array are used for $1^{st}$ strand synthesis, but the primers used for synthesis of $2^{nd}$ strands are not attached to the matrix of the array. In this aspect of the present invention, a pool of primers for $2^{nd}$ strands in solution can make use of normal nucleic acid kinetics to find $1^{st}$ strand templates fixed to distinct loci on an array for $2^{nd}$ strand priming events.

FIGS. 22-25 show an example of a series of binding and extension reactions with only the SPE's fixed to an array. In this example, SPE-P1 is a primer fixed to Locus P that is complementary to the (+) strand of target P and P2 is a primer that is free in solution and is complementary to the (−) strand of target P. SPE-Q1 is a primer fixed to Locus Q that is complementary to the (+) strand of target Q and Q2 is a primer that is free in solution and is complementary to the (−) strand of target Q.

It can be seen in FIGS. 22-25 that the specificity of the reaction and anchoring of the amplification to a specific locus can be entirely directed by this $1^{st}$ strand copying reaction. As such, the identity of the primers that are free in solution are not important as long as they are capable of synthesizing nucleic acids that can specifically bind to the SPE's on the array. Thus although, unique specific sequences were used in FIGS. 22-25 for illustration of $2^{nd}$ strand priming/extension reactions, in this aspect of the invention where a mixed phase amplification is carried out, the primers for synthesis of $2^{nd}$ strands could also be a carried out by a mixture of UPE's or they can even comprise a pool of or random primers. This particular aspect of the present invention also finds use with general arrays that represent multitudes of variations of sequences. For instance, an array that is created by in situ synthesis as described by Affymatrix can be synthesized with some or all of the 65,536 permutations of an octamer array and then used in conjunction with UPE's in solution.

Another aspect of the present invention discloses novel methods, compositions and kits for the preparation and use of protein and ligand arrays which serve to increase the exposure of the binding substance on the array and decrease non-specific binding to the matrix itself. In one embodiment, chimeric compositions are disclosed that are comprised of two segments, a nucleic acid portion and a non-nucleic portion. The nucleic acid portion is used to achieve a practical and more accessible method for attaching the non-nucleic acid portion to a solid support. In one method of use, the nucleic acid portion is directly bound to the surface of the array where it serves as a linker between the array surface and the non-nucleic acid portions of the chimeric compositions. In addition, due to the phosphate charges of the nucleic acid, each chimeric composition at a locus should exhibit repulsive forces that should minimize interactions between the chimeric compositions.

Since use is being made of its physical properties rather than its sequence identity, any particular sequence can be used generically for all the various chimeric compositions. Information on the identity of the non-nucleic acid portion is not derived from the nucleic acid portion but rather form the spatial location on the array where the chimeric composition has been fixed or immobilized. This is in contrast to prior art, which intrinsically required a diversity of specific sequences for the nucleic acid portion and a subsequent "decoding" of the nucleic acid portion. In another embodiment of the present invention, the nucleic acid portion of the chimeric composition comprises discrete sequences that allow binding of the chimeric composition to the array through hybridization to complementary sequences that are immobilized on the support.

The nucleic acid portion of a chimeric composition can be comprised of deoxynucleotides, ribonucleotides, modified nucleotides, nucleic acid analogues such as peptide nucleic acids (PNAs), or any combination thereof. The sequence of the nucleic acid portion is of completely arbitrary nature and may be chosen by the user. In one aspect of the present invention, advantage is taken of the intrinsic properties of nucleic acid hybridization for the attachment of the non-nucleic acid portion to the solid surface used for the array. Thus, the present invention allows the high specificity, tight binding and favorable kinetics that are characteristic of nucleic acid interactions to be conveyed to a non-nucleic acid portion that does not enjoy these properties.

The non-nucleic acid portion of the chimeric composition of the present invention can be comprised of peptides, proteins, ligands or any other compounds capable of binding or interacting with a corresponding binding partner. Peptides and proteins can be comprised of amino acid sequences ranging in length from small peptides to large proteins. This peptides and proteins can also comprise modified amino acids or analogues of amino acids. The amino acids or analogues can comprise any desirable sequence. For instance, the amino acid sequences can be derived from enzymes, antibodies, antigens, epitopes of antigens, receptors and glycoproteins. When peptides or proteins are used as the non-nucleic acid portion of the chimeric composition, the sequences of the nucleic acid portion are of arbitrary nature and have no correspondence to the amino acid sequences of the peptides or proteins. Other molecules besides peptides and proteins may also find use in the present invention. Examples of other constituents that could be used for the non-nucleic acid portion can comprise but not be limited to ligands of MW of 2000 or less, substrates, hormones, drugs and any possible protein binding entity.

As described previously, the particular sequence of the nucleic acid is determined by the user. In one method of use of the present invention, each individual species that is used as the non-nucleic acid portion can be covalently joined to a unique nucleic acid sequence. Hybridization of a the nucleic acid portion of the chimeric composition to a complementary sequence at a particular locus on an array thereby determines the identity of the particular species of the non-nucleic acid portion that is now bound to that locus. For example, one hundred different chimeric compositions can be synthesized that each comprises a unique peptide and a unique nucleic acid sequence. Hybridization can then be carried out with an array that has one hundred different loci, where each locus has nucleic acids complementary to one of the unique nucleic acid sequences. Hybridization thereby results in the localization of each unique peptide to one particular locus on the array, transforming a nucleic acid array into a peptide array. A useful method for selection of sequences that could be used for the nucleic acid portion has been described by Hirschhorn et al., (op.cit.) hereby incorporated by reference. Also, since no relationship is required between the non-nucleic portion and the nucleic acid portion, a different set of one hundred chimeric compositions can be designed that have different species used for the non-nucleic acid portion but use the same set of one hundred sequences for the nucleic acid portion. In this way, a generic nucleic acid array can be used to create different peptide arrays by changing the identities of the chimeric compositions.

Alternatively, non-nucleic acid protein binding substances can be attached to oligonucleotides which all comprise the same sequence. For example, chimeric compositions with various non-nucleic portions could be synthesized where the nucleic acid portion of each chimeric compositions comprised a common poly T sequence. The matrix can be prepared so that the oligonucleotides at each site consist of complementary Poly A sequences. The chimeric compositions can then be applied to the matrix using an addressable arraying system that has been described by Heller et al. in U.S. Pat. No. 5,605,662 (herein incorporated by reference). By these means, each particular chimeric composition can be applied individually to the matrix using an electronically controlled system and immobilized through hybridization to the appropriate site.

The chimeric compositions at a particular locus of an array do not have to be completely uniform in nature, i.e. an oligonucleotide sequence can be attached to several different species of non-nucleic acid portions. For example, a series of one hundred peptides can be placed on the array in only four different sites by making Pool 1 with twenty-five peptides conjugated to oligonucleotide 1, Pool 2 with twenty-five peptides conjugated to oligonucleotide 2, Pool 3 with twenty-five peptides conjugated to oligonucleotide 3 and Pool 4 with twenty-five peptides conjugated to oligonucleotide 4. Attachment of the various pools of chimeric compositions to each locus can be carried out by having oligonucleotide 1, 2, 3 and 4 comprising unique sequences complementary to different oligonucleotides at each site or as described above, an addressable arraying system can be used to localize each pool using nucleic acid portions with identical sequences. The chimeric compositions comprised of nucleic acid and non-nucleic acid portions can be synthesized using any method known to those skilled in the art. Methods that may find use with the present invention are described in a review by Tung, C.-H.; (2000 Bioconjugate Chemistry 11, 5, 605-618) and Engelhardt et al., U.S. Pat. No. 5,241,060, issued Aug. 31, 1993 and Pergolizzi et al., U.S. patent application Ser. No. 08/479,995, filed Jun. 7, 1995, for Analyte Detection Utilizing Polynucleotide Sequences, Composition, Process and Kit, based on priority U.S. patent application Ser. No. 06/491,929, filed May 5, 1983, all incorporated herein by reference. In one approach, peptides and oligonucleotides are synthesized separately using standard automated procedures and then covalently bonded together. For example, a thiol group can be added either to the 5'-terminus of the oligonucleotide or internally in the nucleic acid portion of the chimeric composition. Addition of a maleimido group to the N-terminus or in an internal position of the peptide allows a reaction with the thiol group of the oligonucleotide to form a chimeric composition comprised of a nucleic acid and a peptide (Eritja et al., (1991) Tetrahedron, 47; 4113-4120. Arar et al.; (1993) Tetrahedron Lett 34; 8087-8090, Ede et al., (1994) Bioconjugate Chemistry 5; 373-378, Stetsenko and Gait, (2000) J. Org. Chem. 65; 4900-4908). Alternatively the chimeric composition can be prepared by the stepwise addition of amino acids and nucleotides on the same solid support, (de la Torre et al., (1994) Tetrahedron Lett 35; 2733-2736, Bergmann and Bannwarth (1995) Tetrahedron Lett. 36; 1839-1842, Robles et al., (1999) Tetrahedron 55; 13,251-13,264, Antopolsky et al., (1999) Helv. Chim Acta 82; 2130-2140). In these publications each of which is incorporated by reference herein, the peptide was synthesized first followed by the addition of bases to synthesize the oligonucleotide portion. In standard peptide synthesis, the N-terminus and the side chains of the amino acids are protected by Fmoc and tert-butyl groups respectively. At each cycle the Fmoc group is removed with 20% piperidine and the side chains are deprotected with 90% trifluoroacetic acid. However when both oligonucleotides and peptides were synthesized as part of a single composition, different chemistries had to be used. For example, base labile Fmoc and 9-fluorenylmethyl groups were used as the amino acid side chain protecting groups to avoid exposing the DNA to strong acids (de la Torre, op cit.; de la Torre et. al., 1999 Bioconjugate Chem. 10; 1005-1012; Robles et al op cit.), all such publications being incorporated by reference herein. Methods for making chimeric compositions of peptides fused to PNA analogues of nucleic acids have been described by Cook et al. in U.S. Pat. No. 6,204,326, incorporated herein by reference. Furthermore, chimeric compositions comprised of nucleic acids and peptides can be synthesized directly on a solid surface to create an array using the methods described by Sundberg et al in U.S. Pat. No. 5,919,523 incorporated herein by reference.

The solid support can be any material used for arrays including, but not limited to nylon or cellulose membranes, glass, synthetic, plastic, metal. The materials can be opaque, reflective, transparent or translucent. They can be porous or they can be non-porous. Nucleic acids that are either part of chimeric compositions or meant to be complementary to chimeric compositions can be affixed to the solid support by any previously known methods used to prepare DNA arrays.

Binding of analytes to appropriate binding partners can be carried out in either a mixed phase or a liquid phase format. For instance, the present invention has disclosed the direct fixation of binding substances to the array by the use of rigid arm linkers and chimeric compositions. The binding substance on the array (the solid phase) can be exposed to a solution (the liquid phase) that contains the analytes of interest. Interactions between the binding substance on the array and analytes in solution can then later be quantified. Examples of the interactions that may find use in the present invention can comprise but not be limited to peptide-protein, antigen-antibody, ligand-receptor or enzyme-substrates. For example, an array can be prepared with a series of peptides to determine their ability to bind to a particular antibody. The array is incubated in a solution containing the antibody followed by washing away the unbound material. Detection of the antibody bound to various components on the array can then be carried out by any of a number of conventional techniques. For instance, in this example the antibody that is applied to the array can be labeled with biotin for indirect detection, or a fluorescent compound for direct detection. Alternatively, the antibody analyte is unlabeled and a secondary antibody can be utilized which either has a fluorescent label for direct detection or indirect label such as biotin. Thus, in this example the antibody-antigen interaction occurs with the antigen bound to the solid matrix.

The present invention has also disclosed the use of chimeric compositions that are indirectly bound to the array through hybridization of the nucleic acid portions of the chimeric compositions to complementary nucleic acids fixed or immobilized to the array. These can be used in the same mixed phase format that has been described above by hybridization of the chimeric compositions to the array followed by binding of analytes. However, the use of hybridization to immobilize the chimeric compositions to specific loci on the array allows the use of a completely liquid phase format for binding of analytes to the chimeric compositions. In this way, the chimeric compositions can be combined with the target molecules in solution under optimal conditions for interactions between the analyte and the non-nucleic acid portions of the chimeric compositions. The resultant solution, containing the chimeric compositions free in solution as well as the chimeric compositions that are bound into complexes with the analytes, can then be applied to the matrix and the various chimeric compositions will be localized to various locations on the array through hybridization to the nucleic acid portion to complementary sequences on the array. An illustration of this process is given in FIG. 26.

The hybridization can be carried out under mild conditions, which will not interfere with the ligand-receptor or protein-protein complex. Protein-protein interactions are generally characterized by low Km's, in the order of magnitude of $10^{-5}$ to $10^{-9}$. In this aspect of the present invention, the protein interactions can occur in solution rather than on a solid surfaces which will allow superior kinetics of binding and will also allow a wider variety of conditions for protein binding than can be obtained in the mixed format. Also, by chimeric compositions and analytes together in solution, direct interaction or interference with the matrix is avoided, thereby decreasing the background. Therefore, to use the example cited before, the solution containing the antibody target is combined with a solution containing the chimeric composition. Thus, by using the methods of the present invention, the proteins will remain in solution throughout the process preventing any problems associated with dehydrating the protein bound to the solid matrix.

The method of the present invention can be used to study many systems that involve interactions between compound. These can include but not be limited to antigen-antibody relationships, protein-protein interactions, enzyme-substrate receptor-ligand interactions, ligand-receptor, hormone-receptor, carbohydrate-lectins, drug screening, and patterns of expression of proteins in a cell or tissue. Another method of use of the present invention is that instead of using unique nucleic acid portions for each individual non-nucleic acid portion, one specific binding substance can be combined with various nucleic acid sources to form a group of chimeric compositions with a common non-nucleic acid portion and a unique nucleic acid portion. Each particular chimeric composition can be combined with an analyte from a different source and applied to the array by hybridizing the nucleic acid portions to their complementary sequences on the array. The proteins bound to the array can then be detected following standard procedures. By these means, the amount of targets from each source that can interact with the binding substance in the chimeric compositions can be simultaneously determined.

For instance, a set of twenty different compositions can be synthesized where each member of the set will have a different nucleic acid portion but the same peptide. Another set can be made with a different peptide that is linked to twenty other nucleic acid portions. More sets can be made on the same basis. Protein extracts can then be made from twenty different tissues and each extract can be combined with a different member of the set of chimeric compositions. Thus, the nucleic acid portion serves as a marker for not only the peptide but also for the particular tissue that was used as the source. For instance, a group of sets can be made with peptides that have affinities for different receptors. After incubation of the mixtures with the chimeric compounds, the mixtures are applied to the array and detected. In this way, each particular receptor that is being studied can be quantified and compared simultaneously between various tissues. Alternatively, the same nucleic acid sequence can be used in common for each source by using the addressable system described previously, and carrying out hybridization to each locus after addition of each individual reaction mixture.

The same method can be applied to tissues or cell cultures that are from the same source but are treated differently. For example, in a drug discovery program, nine different drugs can be added to individual cell cultures to determine the effect on specific proteins. Chimeric compositions are designed and synthesized with peptides that are known to react with each of proteins that is to be monitored. As in the previous example, a specific nucleic acid sequence will serve as a marker for each peptide and each particular treatment. The proteins are extracted from each of the ten cell cultures (nine drug treated plus an untreated control) and incubated with the chimeric compositions. The mixtures are applied to the array and the amount of analyte bound to the corresponding peptides at each locus of the array is measured for the various drug conditions. If desired, the present invention can also be used for the isolation of analytes. This can be carried out by either disrupting the interaction between the analyte and the non-nucleic acid portion of the chimeric compositions or by denaturing the nucleic acid portion from the complementary sequence fixed or immobilized to the array. It is also contemplated that removal of chimeric compositions from the array may also allow the reuse of the array in other experiments.

In further detail, this invention provides novel chimeric compositions and processes using such chimeric compositions. One such composition of matter comprises an array of solid surfaces comprising a plurality of discrete areas, wherein at least two of such discrete areas comprise: a chimeric composition comprising a nucleic acid portion; and a non-nucleic acid portion, wherein the nucleic acid portion of a first discrete area has the same sequence as the nucleic acid portion of a second discrete area, and wherein the non-nucleic acid portion has a binding affinity for analytes of interest.

Another composition of matter comprises an array of solid surfaces comprising a plurality of discrete areas; wherein at least two of the discrete areas comprise a chimeric composition hybridized to complementary sequences of nucleic acids fixed or immobilized to the discrete areas, wherein the chimeric composition comprises a nucleic acid portion, and a non-nucleic acid portion, the nucleic acid portion comprising at least one sequence, wherein the non-nucleic acid portion has a binding affinity for analytes of interest, and wherein when the non-nucleic acid portion is a peptide or protein, the nucleic acid portion does not comprises sequences which are either identical or complementary to sequences that code for such peptide or protein.

Mention should be made of a process for detecting or quantifying analytes of interest, the process comprising the steps of 1) providing a) an array of solid surfaces comprising a plurality of discrete areas, wherein at least two of such discrete areas comprise a chimeric composition comprising a nucleic acid portion, and a non-nucleic acid portion; wherein the nucleic acid portion of a first discrete area has the same sequence as the nucleic acid portion of a second discrete area; and wherein the non-nucleic acid portion has a binding affinity for analytes of interest; b) a sample containing or suspected of containing one or more of the analytes of interest; and c) signal generating means; 2) contacting the array a) with the sample b) under conditions permissive of binding the analytes to the non-nucleic acid portion; 3) contacting the bound analytes with the signal generating means; and 4) detecting or quantifying the presence of the analytes.

Another process for detecting or quantifying analytes of interest comprises the steps of 1) providing a) an array of solid surfaces comprising a plurality of discrete areas; wherein at least two of such discrete areas comprise a chimeric composition comprising a nucleic acid portion; and a non-nucleic acid portion; wherein the nucleic acid portion of a first discrete area has the same sequence as the nucleic acid portion of a second discrete area; and wherein the non-nucleic acid portion has a binding affinity for analytes of interest; b) a sample containing or suspected of containing one or more of the analytes of interest; and c) signal generating means; 2) labeling the analytes of interest with the signal generating means; 3) contacting the array a) with the labeled analytes under conditions permissive of binding the labeled analytes to the non-nucleic acid portion; and 4) detecting or quantifying the presence of the analytes.

Another process for detecting or quantifying analytes of interest comprises the steps of 1) providing a) an array of solid surfaces comprising a plurality of discrete areas; wherein at least two of such discrete areas comprise nucleic acids fixed or immobilized to such discrete areas, b) chimeric compositions comprising: i) a nucleic acid portion; and ii) a non-nucleic acid portion; the nucleic acid portion comprising at least one sequence, wherein the non-nucleic acid portion has a binding affinity for analytes of interest, and wherein when the non-nucleic acid portion is a peptide or protein, the nucleic acid portion does not comprise sequences which are either identical or complementary to sequences that code for the peptide or protein; c) a sample containing or suspected of containing the analytes of interest; and d) signal generating means; 2) contacting the array with the chimeric compositions to hybridize the nucleic acid portions of the chimeric compositions to complementary nucleic acids fixed or immobilized to the array; 3) contacting the array a) with the sample b) under conditions permissive of binding the analytes to the non-nucleic acid portion; 4) contacting the bound analytes with the signal generating means; and 5) detecting or quantifying the presence of the analytes.

Another process for detecting or quantifying analytes of interest comprises the steps of 1) providing a) an array of solid surfaces comprising a plurality of discrete areas; wherein at least two of the discrete areas comprise nucleic acids fixed or immobilized to the discrete areas, b) chimeric compositions comprising i) a nucleic acid portion; and ii) a non-nucleic acid portion, the nucleic acid portion comprising at least one sequence, wherein the non-nucleic acid portion has a binding affinity for analytes of interest, and wherein when the non-nucleic acid portion is a peptide or protein, the nucleic acid portion does not comprise sequences which are either identical or complementary to sequences that code for the peptide or protein; c) a sample containing or suspected of containing the analytes of interest; and d) signal generating means; 2) contacting the chimeric compositions with the sample b) under conditions permissive of binding the analytes to the non-nucleic acid portion; 3) contacting the array with the chimeric compositions to hybridize the nucleic acid portions of the chimeric compositions to complementary nucleic acids fixed or immobilized to the array; 4) contacting the bound analytes with the signal generating means; and 5) detecting or quantifying the presence of the analytes.

Another useful process comprises the steps of 1) providing a) an array of solid surfaces comprising a plurality of discrete areas; wherein at least two of the discrete areas comprise nucleic acids fixed or immobilized to the discrete areas, b) chimeric compositions comprising i) a nucleic acid portion; and ii) a non-nucleic acid portion; the nucleic acid portion comprising at least one sequence, wherein the non-nucleic acid portion has a binding affinity for analytes of interest, and wherein when the non-nucleic acid portion is a peptide or protein, the nucleic acid portion does not comprise sequences which are either identical or complementary to sequences that code for the peptide or protein; c) a sample containing or suspected of containing the analytes of interest; and d) signal generating means; 2) contacting the array with the chimeric compositions to hybridize the nucleic acid portions of the chimeric compositions to complementary nucleic acids fixed or immobilized to the array; 3) labeling the analytes of interest with the signal generating means; 4) contacting the array with the labeled analytes to bind the analytes to the non-nucleic acid portion; and 5) detecting or quantifying the presence of the analytes.

Another process for detecting or quantifying analytes of interest comprises the steps of 1) providing a) an array of solid surfaces comprising a plurality of discrete areas; wherein at least two of the discrete areas comprise nucleic acids fixed or immobilized to the discrete areas, b) chimeric compositions comprising: i) a nucleic acid portion; and ii) a non-nucleic acid portion; the nucleic acid portion comprising at least one sequence, wherein the non-nucleic acid portion has a binding affinity for analytes of interest, and wherein when the non-nucleic acid portion is a peptide or protein, such nucleic acid portion does not comprise sequences which are either identical or complementary to sequences that code for the peptide or protein; c) a sample containing or suspected of containing the analytes of interest; and d) signal generating means; 2) contacting the array with the chimeric compositions to hybridize the nucleic acid portions of the chimeric compositions to complementary nucleic acids fixed or immobilized to the array; 3) labeling the analytes of interest with the signal generating means; 4) contacting the array with the labeled analytes to bind the analytes to the non-nucleic acid portion; and 5) detecting or quantifying the presence of the analytes.

The elements recited in the last several chimeric compositions and processes using such chimeric compositions are described elsewhere in this disclosure.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Amplification of a Library of RNA Targets with $2^{nd}$ Strand Synthesis Carried Out by Random Primers with T7 Promoter Sequences 1) First Strand Synthesis Two mixtures of 250 ng of rabbit globulin mRNA (Life Technologies, Rockville, Md.) and 200 ng of Oligo $(dT)_{24}$ (SEQ ID NO: 4) (In house or purchased?) in 5 ul were heated at 70° C. for 10 minutes followed by a 2 minute incubation on ice. This material was then used in 10 ul reactions containing 50 mM Tris-HCl (pH 8.3), 75 mM KCl, 3 mM $MgCl_2$, 10 mM DTT, 600 uM dNTPs and 120 units of Superscript II RNase $H^-$ Reverse Transcriptase (Life Technologies, Rockville, Md.) with incubation at 42° C. for 60 minutes.

2) Second Strand Synthesis

KOH was added to the reactions for a final concentration of 200 mM. Incubation was carried out at 37° C. for 30 minutes followed by neutralization with an equimolar amount of glacial acetic acid. Primers with the following sequence were used for $2^{nd}$ strand synthesis:

(SEQ ID NO: 5)
5'-GGCCAGTGAATTGTAATACGACTCACTATAGGGAGGCGGN$_{1-9}$-3'

Primers with the sequence above (TPR primers) consist of a T7 promoter sequence at their 5' ends and 9 nucleotides with random sequences at their 3' ends. 400 pmoles of TPR primers and other appropriate reagents were added for a final reaction mix of 30 ul containing 86.6 mM Tris-HCl (pH 7.6), 32 mM KCl, 200 mM KOAc (??), 15.6 mM $MgCl_2$, 3.3 mM DTT, 10 mM Dithioerythritol (DTE), 10 mM $(NH_4)_2SO_4$, 0.15 mM-NAD, 200 ug/ml nuclease-free BSA (Bayer, Kankakee, Ill.), Annealing was carried out by heating the mixture to 65° C. and slow cooling to room temperature followed by incubation on ice for 5 minutes. Extension of the primers was carried out by addition of 1.2 ul of 10 mM dNTPs, 4 units of *E. coli* DNA ligase (New England Biolabs, Beverly, Mass.) and either 12 units of DNA polymerase I (New England Biolabs, Beverly, Mass.) or 6 units of the Exo (−) version of the Klenow fragment of DNA Polymerase I (New England Biolabs, Beverly, Mass.). Incubation was carried out at 15° C. for 5 minutes followed by 37° C. for 120 minutes. The reactions were purified by extraction with Phenol/Chloroform with Phase-Lock Gels (Eppendorf, Westbury, N.Y.) and Ethanol precipitated.

3) Transcription

Transcription was carried out by using the BioArray High Yield Transcription Kit (T7) (ENZO Diagnostics, Farmingdale, N.Y.) following the manufacturers instructions with a final volume of 40 ul. The reaction mixes also contained 10 uCi of $^3$H-ATP with a specific activity of 45 Ci/mMol (Amersham Pharmacia, Piscataway, N.J.). Incorporation was measured by addition of 5 ul of the transcription reaction to 1 ml of 10% TCA, 50 ug/ml Poly A, 5 mM EDTA followed by incubation on ice for 30 minutes. Precipitates were collected on 25 mm glass fiber filters (Whatman, Lifton, N.J.) followed by three washes with 5% TCA and three washes with ethanol 4) Results and Conclusions

| Sample 1 with DNA polymerase I | 4,243 cpm |
|---|---|
| Sample 2 with Exo (−) Klenow | 19,662 cpm |

This example demonstrated that RNA transcripts were obtained from a library of nucleic acids by the steps described above and that under the conditions used, the Exo (−) version of Klenow resulted in more product compared to the use of DNA polymerase I.

Example 2

Amplification of a Library of RNA Targets with $1^{st}$ Strand Synthesis Using Oligo-T Magnetic Beads and $2^{nd}$ Strand Synthesis Carried Out by Random Primers with T7 Promoter Sequences 1) Preparation of Beads 50 ul of Dynal Oligo $(dT)_{25}$ (SEQ ID NO: 6) magnetic beads (Dynal Inc., Lake Success, N.Y.) were washed two times with 100 ul of Binding Buffer (20 mM Tris-HCl (pH 7.5), 1.0 M LiCl, 2 mM EDTA) and then resuspended in 50 ul of Binding Buffer.

2) Binding of RNA to Beads

RNA targets were prepared by diluting I ug of mouse poly A RNA (Sigma Chemical Co, St. Louis, Mo.) or I ug of wheat germ tRNA (Sigma Chemical Co, St. Louis, Mo.) into RNase-free $H_2O$ (Ambion, Austin, Tex.) for a final volume of 50 ul, and heating the RNA solution at 65° C. for 5 minutes. The RNA solution was combined with the beads prepared in Step 1 and mixed for 15 minutes at room temperature with a Dynal Sample Mixer (Dynal Inc., Lake Success, N.Y.). Unbound material was removed by magnetic separation with a Dynal Magnetic Particle Concentrator (Dynal, Inc. Lake Success, N.Y.) followed by two washes with 200 ul of Wash Buffer B (10 mM Tris-HCl (pH 7.5), 150 mM LiCl, 1 mM EDTA) and three washes with 250 ul of First Strand Buffer (50 mM Tris-HCl (pH 8.3), 75 mM KCl, 3 mM $MgCl_2$)

3) First Stand Synthesis

The beads from Step 2 were resuspended in 50 mM Tris-HCl (pH 8.3), 75 mM KCl, 3 mM $MgCl_2$, 10 mM DTT, 500 uM dNTPs and 400 units of Super Script II RNase $H^-$ Reverse Transcriptase (Life Technologies, Rockville, Md.) and incubated for 90 minutes at 42° C.

4) Second Strand Synthesis

RNA templates were removed by heating the First Strand Synthesis reaction mixture of step 3 at 90° C. for 5 minutes followed by removal of the supernatant after magnetic separation. The beads were washed two times with 100 ul of Buffer C (70 mM Tris-HCl (ph 6.9) 90 mM KCl, 14.6 mM $MgCl_2$, 10 mM DTE, 10 mM $(NH_4)_2SO_4$ and 200 ug/ml nuclease-free BSA) and resuspended in 50 ul of Random Priming Mix A (86.7 mM Tris-HCl (pH 7.6), 113.3 mM KCl, 17 mM $MgCl_2$, 11.3 mM DTT, 11.3 mM $(NH_4)_2SO_4$, 227 ug/ml nuclease-free BSA) containing 360 pmoles of TPR primers. Primers were allowed to anneal on ice for 15 minutes. Unbound primers were removed by magnetic separation. The beads were resuspended in 50 ul of Random Priming Mix A (without the TPR primers) with 10 units of the Klenow fragment of DNA Polymerase I (New England Biolabs, Beverly, Mass.) and 400 mM dNTP's. Incubation was carried out for 5 minutes at 4° C., 30 minutes at 15° C., and 30 minutes at 37° C. For some samples, an additional 25 ul of Oligo T magnetic beads prepared as described in Step 1 were washed with Buffer C and added to the reaction mix. Also, for some samples, 3 units of T4 DNA Polymerase (New England Biolabs, Beverly, Mass.) and 2 ul of a 10 mM stock of dNTPs were added to the reaction mixtures. Samples with these further steps were incubated for 30 minutes at 37° C. At the conclusion of the varied reactions, the beads were magnetically separated from the reagents and the beads were used to carry out transcription assays.

5) Transcription Synthesis

Transcription reactions were carried out by resuspending the beads in reagents from the BioArray High Yield Transcription Kit (T7) (ENZO Diagnostics, Farmingdale, N.Y.) using the manufacturer's instructions with a final volume of 40 ul. The reaction mixtures also contained 10 uCi of $^3$H-ATP with a specific activity of 45 Ci/mMol (Amersham Pharmacia, Piscataway, N.J.). Extent of transcription was measured by using TCA precipitation as described previously.

6) Results

| Sample | Target | Extra Beads | T4 DNA polymerase | cpm Incorporated |
|---|---|---|---|---|
| 1 | Poly A | (−) | (−) | 8,535 |
| 2 | Poly A | (−) | (+) | 15,483 |
| 3 | Poly A | (+) | (−) | 16,048 |
| 4 | Poly A | (+) | (+) | 18,875 |
| 5 | tRNA | (+) | (+) | 2,548 |

7) Conclusions

This example demonstrated that transcripts were obtained from a library of nucleic acids by the steps described above. Addition of extra beads can increase the amount of synthesis. The reaction can be carried out without a T4 DNA polymerization step but the amount of synthesis can be increased by the addition of such a reagent.

Example 3

Dependency on Reverse Transcriptase for Amplification of a Library of RNA Targets with Oligo-T Magnetic Beads and Random Primers with T7 Promoter Sequences 1) Preparation of Beads This step was carried out as described in Step 1 of Example 2, except the amount of beads was increased to 100 ul for each reaction 2) Binding of RNA to Beads RNA targets were prepared by diluting 1 ug of mouse poly A mRNA (Sigma Chemical Co, St. Louis, Mo.) into nuclease-free H$_2$O (Ambion Inc., Austin Tex.) for a final volume of 50 ul, and heating the RNA solution at 65° C. for 15 minutes. The RNA solution was combined with the beads prepared in Step 1 and mixed for 15 minutes at Room Temperature with a Dynal Sample Mixer (Dynal Inc., Lake Success, N.Y.). Unbound material was removed by magnetic separation followed by two washes with 200 ul of Wash Buffer B and two washes with 100 ul of First Strand Buffer.

3) First Strand Synthesis

This step was carried out as described in step 3 of Example 2 except that a pair of duplicate samples had the Reverse Transcriptase omitted 4) Second Strand Synthesis RNA templates were removed by heating the First Strand Synthesis reaction mixture of step 3 at 90° C. for 4 minutes followed by removal of the supernatant after magnetic separation. The beads were washed two times with 100 ul of Wash Buffer B and resuspended in 50 ul of Random Priming Mix A containing 360 pmoles of TPR primers. Primers were allowed to anneal on ice for 15 minutes. Unbound primers were removed by magnetic separation and the beads were washed twice with 100 ul of cold Buffer D (20 mM Tris-HCl (pH 6.9), 90 mM KCl, 4.6 mM MgCl$_2$, 10 mM (NH$_4$)$_2$SO$_4$. The beads were then suspended in 40 ul of Buffer C that also contained 1 mM dNTPs and 10 units of the Klenow fragment of DNA Polymerase I (New England Biolabs, Beverly, Mass.). Incubation was carried out for 5 minutes at 4° C., 30 minutes at 15° C., and 30 minutes at 37° C. The reaction was carried out further by the addition of 2 ul (6 units) of T4 DNA Polymerase (New England Biolabs, Beverly, Mass.) and 2 ul of a 10 mM stock of dNTPs, followed by incubation for 30 minutes at 37° C.

5) Transcription Synthesis

The beads were washed two times with 100 ul of Wash Buffer B and once with 100 ul of 10 mM Tris-HCl (pH 7.5). The beads were resuspended in 10 ul of 10 mM Tris-HCl (pH 7.5) and mixed with reagents from a BioArray High Yield Transcription Kit (T7) (ENZO Diagnostics, Farmingdale, N.Y.) using the manufacturer's instructions. The volume of the reaction was 30 ul and the incubation was carried out for 2 hours at 37° C.

6) Results and Conclusions

Figure 27:
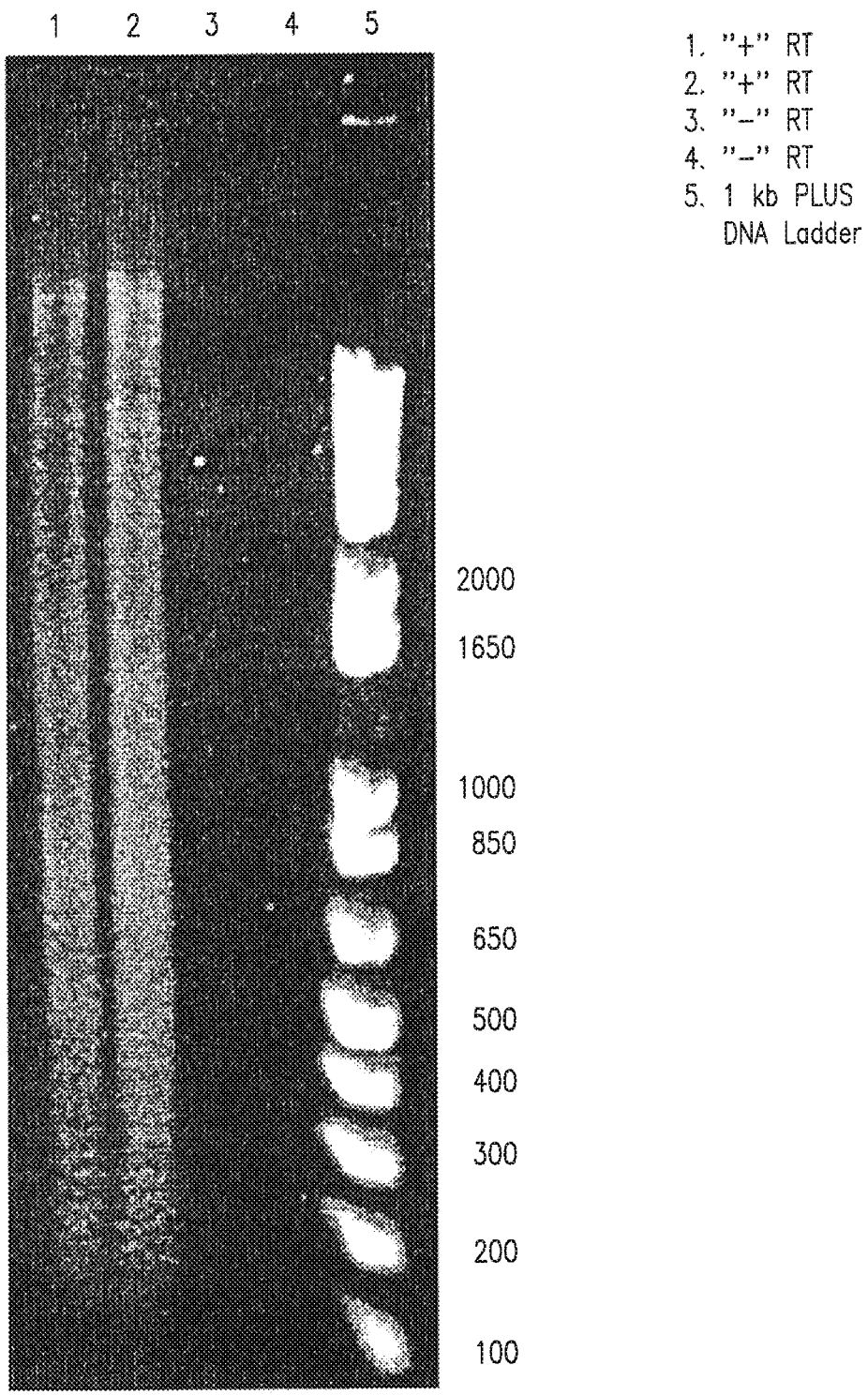
FIG. 27 is a gel analysis illustrating the dependency on Reverse Transcriptase for the amplification of a library in accordance with this invention and Example 3 below.

Analysis of the reaction was carried out by gel electrophoresis of 10 ul of the transcription reaction using 1% Agarose in 0.5×TBE buffer. The results of this experiment are in FIG. 27 for duplicate samples and demonstrate that transcripts were obtained from a library of nucleic acids by the steps described above and this synthesis was dependent upon the presence of Reverse Transcriptase activity.

Example 4

Multiple Rounds of Synthesis of 2$^{nd}$ Strands by Random Primers with T7 Promoters Steps 1, 2 and 3 for Preparation of beads, binding of mRNA and 1$^{st}$ strand synthesis were carried out as described in steps 1 through 3 of Example 3.

4) Second Strand Synthesis

After 1$^{st}$ strand synthesis, the liquid phase was removed by magnetic separation and the beads resuspended in 100 ul of Detergent Wash No. 1 (10 mM Tris-HCl (pH 7.5), 1% SDS) and heated at 90° C. for 5 minutes. The supernatant was removed by magnetic separation and the beads were washed with 100 ul of Detergent Wash No. 2 (40 mM Tris-HCl (pH 8.0), 200 mM KCl, 0.2 mM EDTA, 0.01% Tween 20, 0.01% Nonidet P40). The beads were washed two times with 100 ul of Wash Buffer B and resuspended in 50 ul of Random Priming Mix A containing 360 pmoles of TPR primers. Primers were allowed to anneal on ice for 15 minutes. Unbound primers were removed by magnetic separation and the beads were washed twice with 100 ul of cold Buffer D (20 mM Tris-HCl (pH 6.9), 90 mM KCl, 4.6 mM MgCl$_2$, 10 mM DTT, 10 mM (NH$_4$)$_2$SO$_4$). The beads were then suspended in 40 ul of Buffer C that also contained 1 mM dNTPs and 10 units of the Klenow fragment of DNA Polymerase I (New England Biolabs, Beverly, Mass.). Incubation was carried out for 5 minutes at 4° C., 30 minutes at 15° C., and 30 minutes at 37° C. The reaction was carried out further by the addition of 2 ul (6 units) of T4 DNA Polymerase (New England Biolabs, Beverly, Mass.) and 2 ul of a 10 mM stock of dNTPs, followed by incubation for 30 minutes at 37° C. The beads were then washed two times with 100 ul of Wash Buffer B, resuspended in 50 ul of 10 mM Tris-HCl (pH 7.5) and heated at 90° C. for 5 minutes. The supernatant was removed after magnetic separation and store as supernatant No. 1. The beads were then washed once with 100 ul of Detergent Wash No. 2, two times with 100 ul of Wash Buffer B and resuspended in 50 ul of Random Priming Mix A containing 360 pmoles of TPR primers. Primer annealing and extension was carried out as described above. The beads were then washed two times with 100 ul of Wash Buffer B, resuspended in 50 ul of 10 mM Tris-HCl (pH 7.5) and heated at 90° C. for 5 minutes. The supernatant was removed after magnetic separation and store as supernatant No. 2. The series of washes, annealing and extension steps were carried out again using the steps described above. The beads were then washed two times with 100 ul of Wash Buffer B, resuspended in 50 ul of 10 mM Tris-HCl (pH 7.5) and heated at for 5 minutes. The supernatant was removed after magnetic separation and stored as supernatant No. 3.

5) Synthesis of Complements to the $2^{nd}$ Strands

A pool was created by combining supernatant No. 1, supernatant No. 2 and supernatant No. 3. This pool comprises a library of $2^{nd}$ strands free in solution with T7 promoters at their 5' ends and poly A segments at their 3' ends. Fresh magnetic beads with poly T tails were prepared and annealed to the pool of $2^{nd}$ strands by the same processes described in Steps 1 and 2 of Example 2. Extension was then carried out by resuspension of beads in 50 ul of Buffer C that also contained 1 mM dNTPs and 10 units of the Klenow fragment of DNA Polymerase I (New England Biolabs, Beverly, Mass.). Incubation was carried out at 37° C. for 90 minutes. Transcription was then carried out as described in step 5 of Example 3 except the reaction volume was reduced to 20 ul.

6) Results and Conclusions

Figure 28:
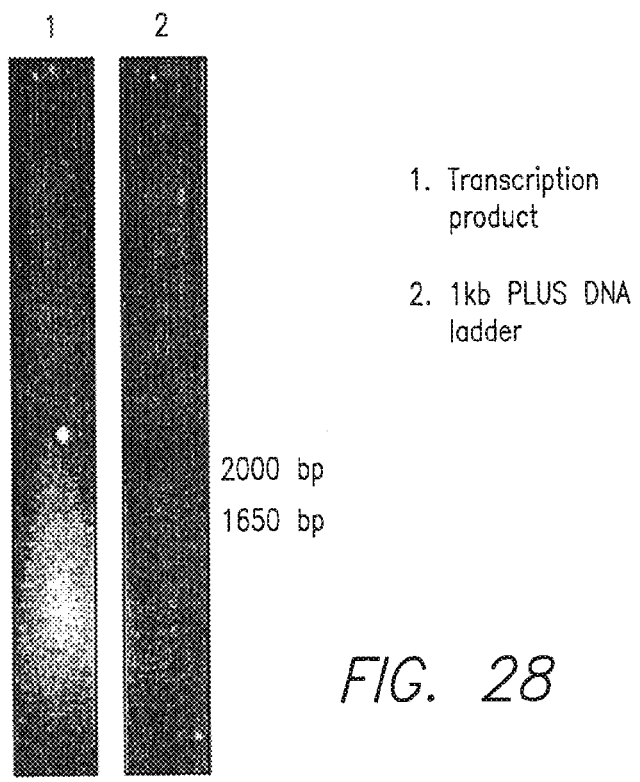
FIG. 28 is a gel analysis that demonstrates transcription after multiple rounds of 2nd strand synthesis as described further below in Example 4.

The results of this experiment are in FIG. 28 and demonstrated that transcripts were obtained from a library of polyA mRNA by the steps described above. This example demonstrated that a library of $2^{nd}$ strands was obtained after multiple rounds of $2^{nd}$ strand synthesis, isolated free in solution and then used to create functionally active production centers Example 5

Additional RNA Synthesis from Transcription Constructs

The library of transcription constructs described in Example 4 were used for a second round of transcription. After removal of transcription products for analysis in Example 4, the beads were resuspended in 100 ul of 10 mM Tris-HCl (pH 7.5) and left overnight at 4° C. The next day, the beads were washed with 100 ul of Detergent Wash No. 2, resuspended in 100 ul of Detergent Wash No. 1 and heated at 42° C. for 5 minutes followed by two washes with 100 ul of Detergent Buffer No. 2, two washes with 100 ul of Wash Buffer B and two washes with 100 ul of 10 mM Tris-HCl (pH 7.5). A transcription reaction was set up as described previously with a 20 ul volume.

Results and Conclusions

Figure 29:
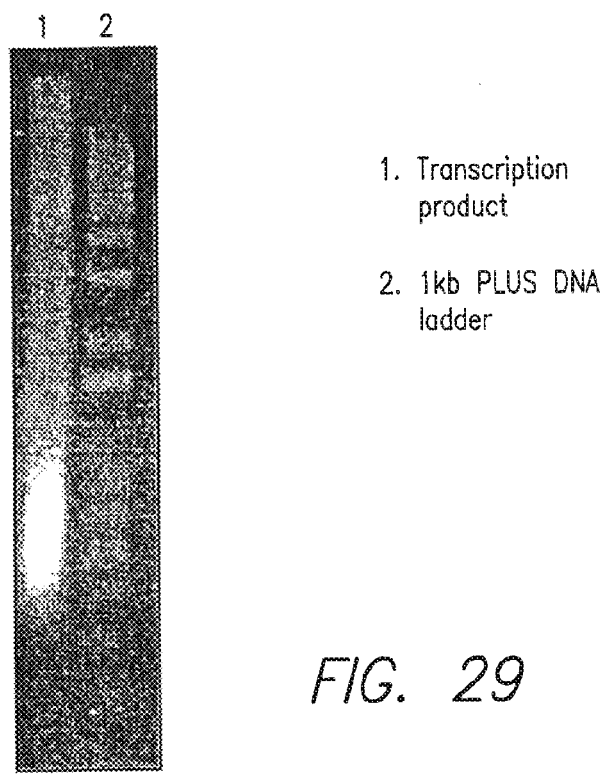
FIG. 29 is also a gel analysis that shows second round of RNA transcription from a library as described in Example 5 below.

Results of the transcription reaction are shown in FIG. 29 and show that the nucleic acids synthesized in Example 4 were stable and could be used for additional transcription synthesis.

Example 6

Terminal Transferase Addition of Poly G Tail to $1^{st}$ Strands for Binding of Primers with T7 Promoter 1) Preparation of Beads 50 ul of Dynal Oligo $(dT)_{25}$ (SEQ ID NO: 6) magnetic beads (Dynal Inc., Lake Success, N.Y.) were washed two times with 100 ul of Binding Buffer (20 mM Tris-HCl (pH 7.5), 1.0 M LiCl, 2 mM EDTA) and then resuspended in 50 ul of Binding Buffer.

2) Binding of RNA to Beads

RNA targets were prepared by diluting 3 ul of 0.5 ug/ul mouse poly A RNA (Sigma Chemical Co, St. Louis, Mo.) with 32 ul of RNase-free $H_2O$ (Ambion, Austin, Tex.) and 40 ul of Binding Buffer, and heating the RNA solution at 65° C. for 5 minutes. The RNA solution was combined with the beads prepared in Step 1 and mixed for 30 minutes at room temperature.

3) First Strand Synthesis

Unbound material was removed by magnetic separation followed by two washes with 200 ul of Wash Buffer B and one wash with 100 ul of First Strand Buffer. The beads were resuspended in a 50 ul mixture of 50 mM Tris-HCl (pH 7.5), 75 mM KCl, 3 mM $MgCl_2$, 10 mM DTT, 500 uM dNTPs and 400 units of Super Script II RNase H⁻ Reverse Transcriptase (Life Technologies, Rockville, Md.) and incubated for 90 minutes at 42° C. At the end of the $1^{st}$ strand synthesis reaction, the liquid phase was removed by magnetic separation and the beads resuspended in 100 ul of Detergent Wash No. 1 and heated at 90° C. for 5 minutes. The supernatant was removed by magnetic separation and the beads were washed with 100 ul of Detergent Wash No. 2, two times with 100 ul of Wash Buffer B and resuspended in 300 ul of 10 mM Tris-HCl (pH 7.5).

4) Second Strand Synthesis

Two methods were used for carrying out second strand synthesis. The first method was as described for the previous examples, I.e the use of TPR primers that have a T7 promoter on their 5' ends and random sequences at their 3' ends. The second method was the use of T7-C9 primers that have a T7 promoter at their 5' ends and a poly C segment at their 3' ends. The sequence of the T7-C9 primers is as follows:

(SEQ ID NO: 1)
5' GGCCAGTGAATTGTAATACGACTCACTATAGGGATCCCCCCCCC-3'

The product of Step 3 was divided into two portions. The first portion (Sample No. 1) consisted of 100 ul and was set aside to be used for random priming. The second portion (the remaining 200 ul) was processed further by magnetically separating the buffer from the beads and resuspending the beads in 100 ul and adding 100 ul of Poly A Mix (1.6 ug/ul Poly A, 10 mM Tris-HCL (pH 7.5), 0.5 M LiCl, 1 mM EDTA). The Poly A was obtained from (Amersham Pharmacia, Piscataway, N.J.) and had an average length of 350 nucleotides. The beads and Poly A were mixed together for 30 minutes at room temperature with a Dynal Sample Mixer (Dynal Inc., Lake Success, N.Y.). The beads were washed two times with Wash Buffer B and resuspended in 200 ul of 10 m Tris-HCl (pH 7.5). This was divided into two 100 ul portions, Sample No. 2 and Sample No. 3. Sample No. 3 was processed further by magnetically separating the buffer from the beads and resuspending the beads in an 80 ul reaction mixture using reagents and directions from the 3' Oligonucleotide Tailing System (ENZO Biochem, Farmingdale, N.Y. 11561) with 0.5 mM dGTP present. Sample No. 3 was incubated for one hour at 37° C. followed by removal of the reagents by magnetic separation. The beads were then resuspended in 100 ul of Detergent Buffer No. 1 and heated at 90° C. for 3 minutes. The beads were then washed once with 100 ul of Detergent Wash No. 2 and twice with 100 ul of Wash Buffer B. Sample No. 3 was resuspended in 100 ul of 10 mM Tris-HCl (pH 7.5). All three samples (Sample No. 1, Sample No. 2 and Sample No. 3) were washed once with 100 ul Wash Buffer E (100 mM Tris-HCl pH7.4) 20 mM KCl, 10 mM $MgCl_2$, 300 mM $(NH_4)_2SO_4$) and then resuspended in 50 ul of Buffer E. Primers for $2^{nd}$ strand synthesis were added to each sample: 4 ul of 100 pMole/ul of TPR primers to Sample No. 1 and 4 ul of 10 pMole/ul of T7-C9 primers to Samples No. 2 and No. 3. Samples were then incubated on ice for 15 minutes followed by one wash with 100 ul of ice cold Buffer E and one wash with ice cold Buffer D. Each sample was resuspended in 40 ul of Buffer D that also contained 1 mM dNTPs and 200 units of the Klenow fragment of DNA Polymerase I (New England Biolabs, Beverly, Mass.). Incubations were carried out for 30 minutes at 15° C. followed by 30 minutes at 37° C.

All three samples were further processed by the addition of 2 ul (3 units) of T4 DNA polymerase (Source, Location) and 2 ul of 10 mM dNTPs followed by incubation at 37° C. for 30 more minutes. Samples were washed twice with 100 ul of 10 mM Tris-HCl (pH 7.5). A Transcription reaction was set up as described previously with a 20 ul volume.

5) Results and Conclusions

Analysis of the reaction was carried out by gel electrophoresis with 2 ul and 10 ul samples of the transcription reaction using 1% Agarose in 0.5×TBE buffer. The results of this experiment are in FIG. 30 and demonstrated that non-inherent UDTs were added to the ends of a library of $1^{st}$ strand copies by the methods described above. The non-inherent UDTs served as primer binding sites for primers with poly C at their 3' ends for synthesis of a library of $2^{nd}$ strands. The difference in the amount of RNA transcription between Samples No. 2 and No. 3 serves as a further indication that comparatively little priming took place at internal sites under the conditions used.

Example 7

Terminal Transferase Addition of Poly G Tail to $1^{st}$ Strands for Binding of Primers with T7 Promoter (Incorporation Assay)

Figure 30:
FIG. 30 is a gel analysis also shows transcription from library made after poly dG tailing in accordance with the present invention and Example 6 below.

The transcription products of Example 6 were analyzed by gel electrophoresis as shown in FIG. 30. To obtain numerical evaluation of the method described in that example, the libraries attached to the beads in Samples No. 1, No. 2 and No. 3 were used in another transcription reaction using $^3$H-incorporation. Transcription was carried out as described in Example 3.

The results were as follows:

| | Random priming |
|---|---|
| Sample No.1) T7-C9 primers without TdT addition step | 6,660 cpm |
| Sample No.2 T7-C9 primers with TdT addition step | 1,144 cpm |
| Sample No.3 | 21,248 cpm |

This second assay agrees with the conclusions of Example 6; i.e. the T7-C9 primers can be used in the present method and more priming took place with the terminally added poly G sequences compared to internal sequences.

Example 8

Incorporation of Promoters after $2^{nd}$ Strand Synthesis

1) Preparation of Beads

Preparation of beads for each sample was carried out as described in step 1 of Example 3

2) Binding of RNA to Beads

In each sample, 1 ug of poly mRNA was bound to beads as described in step 2 of Example 3 with the addition of having 120 units of Prime RNase Inhibitor (Eppendorf, Westbury, N.Y.) present.

3) First Strand Synthesis

First strand synthesis was carried out as described in step 3 of Example 3 except the reaction was also supplemented with 120 units of Prime RNase Inhibitor 4) Second Strand Synthesis Poly dG addition was carried out as described for sample No. 3 in Example 6. Second strand synthesis was performed as described in Example 6 except that 80 pMoles of primers were used in 100 ul reactions. For Samples No. 1 and No. 2, the 2nd strand primers were the T7-C9 primers previously described. For Samples No. 3 and No. 4, the 2nd strand primers were C9 primers with the sequence: 5'-CCCCCCCCC-3'. At the end of the reaction, all samples were washed twice with 100 ul 10 mM Tris-HCl (pH 7.5).

5) Third strand synthesis

Samples No. 2, No. 3 and No. 4 were processed further by resuspension of the beads in 26 ul of 10 mM Tris-HCl (pH 7.5) and heating at 90° C. for 3 minutes. The second strands released by this process were isolated apart from the beads by magnetic separation and mixed with 40 pMoles of $3^{rd}$ strand primers for a final volume of 30 ul. For Sample No. 3, the $3^{rd}$ strand primers were T7-$T_{25}$ primers with the sequence (SEQ ID NO: 2)
5' GGCCAGTGAATTGTAATACGACTCACTATAGGGATC(T)$_{25}$-3'

For Samples No. 2 and No. 4, the $3^{rd}$ strand primers were T3-$T_{25}$ primers with the sequence:

(SEQ ID NO: 3)
5' CTCAACGCCACCTAATTACCCTCACTAAAGGGAGAT(T)$_{25}$-3'

After mixing, Samples No. 2, No. 3 and No. 4 were kept on ice for 15 minutes. Extension reactions were then set up in 1×M-MuLV Buffer (New England Biolabs, Beverly Mass.) with 10 units of M-MuLV Reverse Transcriptase (New England Biolabs, Beverly Mass.) and 1 mM of each dNTP in a final volume of 40 ul. Incubation was carried out for one hour at 37° C. 6 units of T4 DNA Polymerase (New England Biolabs, Beverly, Mass.) were added to Samples No. 1, No. 2, No. 3 and No. 4 and incubation carried out for a further 15 minutes at 37° C. Reactions were stopped by the addition of EDTA (pH 8.0) to a final concentration of 10 mM. The DNA from Samples 2, No. 3 and No. 4 was then purified by adjusting the volumes to 150 ul by adding appropriate amounts of 10 mM Tris-HCl. Reactions were mixed with an equal volume of Phenol:chloroform:isoamyl alcohol (25:24:1) and transferred to 2 ml Phase Lock Gel Heavy tubes (Eppendorf, Westbury, N.Y.). Tubes were vorteed for 1-2 minutes and centrifuged for 10 minutes at 16,000 rpm in a microfuge. The aqueous phase was then transferred to another tube and DNA precipitated with Ethanol and Ammonium Acetate.

6) Transcription

Beads (Sample No. 1) and precipitates (Samples No. 2, No. 3 and No. 4) were resuspended with components from the BioArray High Yield Transcription Kit (T7) (ENZO Diagnostics, NY) and transcription carried out in a 20 ul volume following the manufacturer's directions with the addition of 5 uCi $^3$H-CTP, 20 Ci/mMol (Amersham Pharmacia Biotech, Piscataway, N.J.). In addition some reactions were carried out as described above, but T3 RNA polymerase from the BioArray High Yield Transcription Kit (T3) (ENZO Diagnostics, NY) was substituted. Reactions were carried out for 120 minutes at 37° C.

7) Results

| Sample No. | $2^{nd}$ strand Primer | $3^{rd}$ strand Primer | RNA Polym | CPM |
|---|---|---|---|---|
| No.1 | T7-C9 | — | T7 | 12,392 |
| No.2 | T7-C9 | T3-$T_{25}$ | T7 | 29,160 |
| No.2 | T7-C9 | T3-$T_{25}$ | T3 | 14,784 |
| No.3 | C9 | T7-$T_{25}$ | T7 | 22,622 |
| No.4 | C9 | T3-$T_{25}$ | T3 | 12,221 |

8) Conclusions

This example demonstrated that a promoter can be introduced during $3^{rd}$ strand synthesis to create functional production centers. This example also demonstrated that in addition to a T7 promoter, a T3 promoter was also functional in the present method. This example also demonstrated that different production centers could be introduced into each end of a construct (Sample No. 2) and both production centers were functional.

Example 9

Multiple Rounds of $2^{nd}$ Strand Synthesis with Thermostable Polymerases

1) Preparation of Beads, Binding of RNA to Beads and First strand synthesis were carried out as described in Example 8.

2) Second Strand Synthesis and Recycling

Poly dG addition was carried out as described for sample No. 3 in Example 6 and the beads with tailed 3' ends were used for $2^{nd}$ strand synthesis under various conditions. 50 ul Reactions mixes were set up as follows: Sample No. 1 consisted of 1×Taq PCR Buffer (Epicentre, Madison, Wis.), 3 mM MgCl$_2$, 1×PCR Enhancer (Epicentre, Madison, Wis.), 0.4 mM dNTPs, 40 pMoles C9 primers and 5 units of Master Amp™ Taq DNA Polymerase (Epicentre, Madison, Wis.); Sample No. 2 was the same as sample No. 1 except 100 pMoles of C9 primers were used; Sample No. 3 consisted of 1×Tth PCR Buffer (Epicentre, Madison, Wis.), 3 mM MgCl$_2$, 1×PCR Enhancer (Epicentre, Madison, Wis.), 0.4 mM dNTPs, 40 pMoles C9 primers and 5 units of Master Amp™ Tth DNA Polymerase (Epicentre, Madison, Wis.); Sample No. 4 was the same as sample No. 3 except 100 pMoles of C9 primers were used Samples No. 1 and No. 3 went through one binding/extension cycle while samples No. 2 and No. 4 went through 5 such cycles. Each binding extension/extension cycle was carried out in a thermocycler under the following conditions:

2 minutes at 90° C.
5 minutes at 4° C.
5 minutes at 37° C.
5 minutes at 50° C.
15 minutes at 72° C.

At the end of each cycle, samples No. 2 and No. 4 were briefly shaken to resuspend the beads. After the completion of either 1 or 5 cycles, the mixtures were heated at 90° C. for 3 minutes and the aqueous portion collected after magnetic separation. Each sample was phenol extracted and ethanol precipitated as described previously in step 5 of Example 8 for samples No. 3 and No. 4.

3) Third Strand Synthesis

Pellets were resuspended in 26 ul of 10 mM Tris-HCl (pH 7.5) and T7-T25 primers were added. For Samples No. 1 and No. 3, 40 pMoles of T7-T25 were added; for Samples No. 2 and No. 4, 400 pMoles of T7-T25 were added. Third strand synthesis was then carried out by the addition of MuLV, MuLV buffer and dNTPS as described in step 5 of Example 8.

4) Transcription

Figure 31:
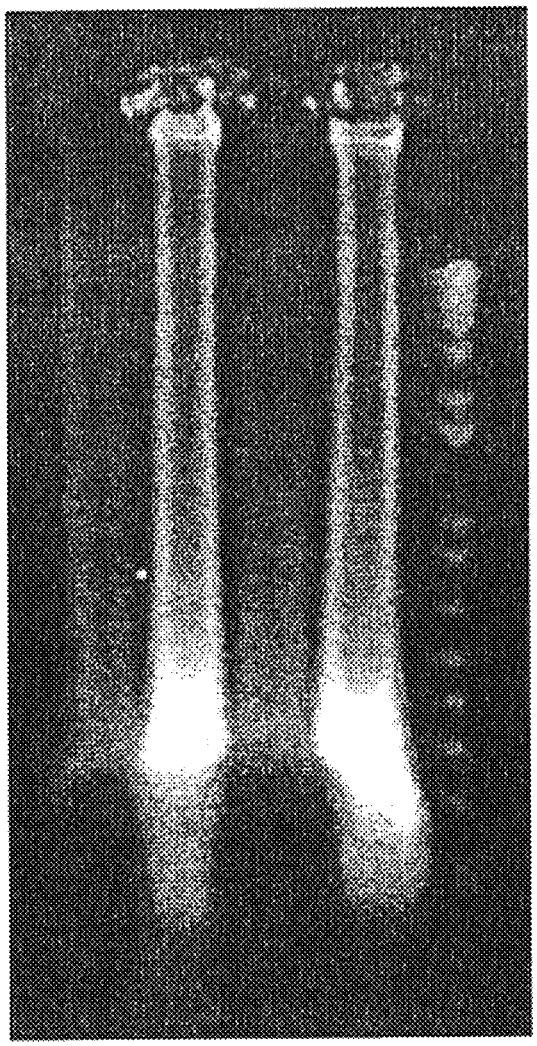
FIG. 31 is a gel analysis that shows RNA transcription after a series of reactions one of which was 2nd strand synthesis by thermostable DNA polymerases as described in Example 9 below.

Transcription was carried out as described previously without the addition of radioactive precursors. Analysis of the reaction from each sample was carried out by gel electophoresis as described previously and shown in FIG. 31.

5) Conclusions

This example demonstrated that thermostable polymerases could be used for $2^{nd}$ strand synthesis in the methods described above. This example also demonstrated that by increasing the amount of primers and the number of cycles the amount of RNA copies derived from the original library of nucleic acids was increased.

Example 10

Levels of Transcription Derived from Sequential Rounds of $2^{nd}$ Strand Synthesis 1) Preparation of Beads, Binding of RNA to Beads and First strand synthesis were carried out as described in Example 8 except the amount of analytes and reagents for each reaction was increased two-fold. Preparation of $1^{st}$ strands for $2^{nd}$ strand synthesis was carried out as described previously for sample 3 in Example 6.

2) Second Strand Synthesis

Second strand synthesis was carried out as described for Sample No. 3 in Example 8. Separation and isolation of the $2^{nd}$ strand products was carried out as described in Example 8 and set aside as Sample No. 1. Fresh reagents were then added to the beads and another round of $2^{nd}$ strand synthesis was carried out. The products of this second reaction were separated from the beads and designated Sample No. 2. The beads were then used once more for a third round of synthesis. The products of this reaction were set aside as Sample No. 3.

3) Third Strand Synthesis

Samples No. 1, No. 2 and No. 3 were used as templates for $3^{rd}$ strand synthesis in individual reactions with the reagents and condition previously described in Example 8. As mentioned above, the starting material in the present example was twice the amount used in example 8 and as such the amounts of all reagents were doubled for this reaction as well. For example, 80 pMoles of T7-T25 primers were used. Purification of the products from each reaction was carried out as described in Example 8.

4) Transcription

Transcription reactions were carried out as with the Bio-Array High Yield Transcription Kit (T7) (ENZO Diagnostics, NY). The DNA was used in a 20 ul final reaction volume which was incubated for 2 hours at 37° C. Gel analysis was then used to evaluate the amount of synthesis that was a result of each round of $2^{nd}$ strand synthesis described above. For purposes of contrast, various amounts of the transcription reaction (4 ul and 10 ul) were analyzed and in addition equivalent amounts of the DNA template that were not used in transcription reactions were also included. The results of this are shown in FIG. 32.

5) Conclusion

This example demonstrated that the $2^{nd}$ strands made in each round of $2^{nd}$ strand synthesis were substantially equal in their ability to be used to synthesize a library with functional production centers. FIG. 32 also shows the contrast between the amount of transcript and the original DNA templates used for this synthesis thereby demonstrating the high levels of synthesis from each template.

Example 11

Use of Reverse Transcriptases from Various Sources

Preparation of Beads, Binding of RNA to Beads and $1^{st}$ strand synthesis were carried out as described in Example 6 except that Reverse Transcriptases from various sources were used for $1^{st}$ strand synthesis reactions. $2^{nd}$ strand synthesis was carried out as described in Example 6 for sample No. 2, i.e Terminal Transferase addition followed by binding and extension of T7-C9 primers. A list of the various Reverse Transcriptases and their sources is given below.

| | |
|---|---|
| 1) Superscript II [RNaseH(−) MuLV] | (Life Technologies, Rockville, MD) |
| 2) RNase H (+) MuLV | (Life Technologies, Rockville, MD) |
| 3) RNase H (+) MuLV | (New England Biolabs, Beverly, MA) |
| 4) Enhanced AMV | (Sigma, St. Louis, MO) |
| 5) AMV | (Life Technologies, Rockville, MD) |
| 6) AMV | (Sigma, St. Louis, MO) |
| 7) Omniscript | (Qiagen |
| 8) Display THERMO-RT | Display Systems Biotech, |
| 9) Powerscript [RNaseH(−) MuLV] | (Clontech laboratories, |

Figure 33:
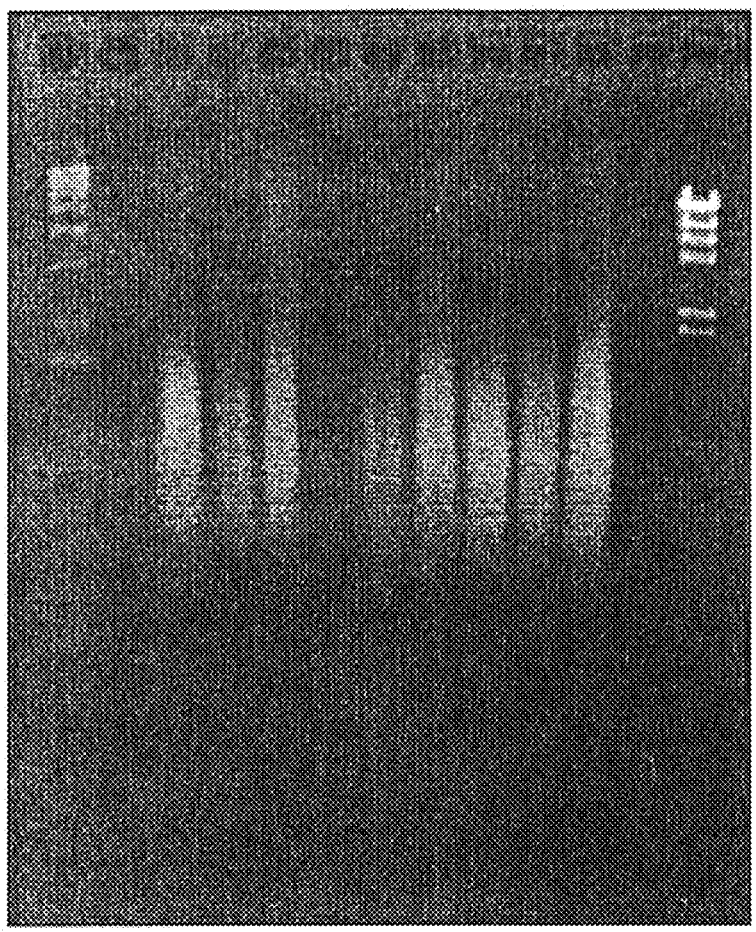
FIG. 33 is also a gel analysis of amplification of a library of analytes using various reverse transcriptases for 1st stand synthesis.

Each $2^{nd}$ stand synthesis was carried out in the buffer provided by the manufacturer for each Reverse Transcriptase with the exception of the New England Biolabs version of RNase H (+) MuLV which was used in the buffer provided for the Life Technologies version of RNase H (+) MuLV. Further processing and transcription reactions were as previously described in Example 6. The results of this experiment re shown in FIG. 33.

CONCLUSIONS

A variety of different Reverse Transcriptases could be used in conjunction with the methods of the present invention.

Many obvious variations will no doubt be suggested to those of ordinary skill in the art in light of the above detailed description and examples of the present invention. All such variations are fully embraced by the scope and spirit of the invention as more particularly defined in the claims that now follow.

---

What is claimed is:

1. A process for detecting or quantifying more than one nucleic acid of interest in a library comprising the steps of:
   a) providing:
      (i) an array of fixed or immobilized nucleic acids identical or complementary in part or whole to sequences of said nucleic acids of interest;
      (ii) a library of nucleic acid analytes which may contain the nucleic acids of interest sought to be detected or quantified;
      (iii) a first set of primers and a second set of primers, wherein the first set of primers comprises at least one production center;
      (iv) polymerizing means for synthesizing nucleic acid copies of said nucleic acid analytes using the first set of primers and the second set of primers;
      (v) a set of oligonucleotides or polynucleotides complementary to at least one segment or sequence of said second set of primers;
      (vi) ligating means for ligating said set of oligonucleotides or polynucleotides (v); and
      (vii) synthesizing means for synthesizing nucleic acid copies under isothermal or isostatic conditions from a production center;
   b) contacting said library of nucleic acid analytes with said first set of primers to form more than one first bound entity, each comprising a first set primer hybridized to a nucleic acid analyte;
   c) using said polymerizing means, extending said bound first set primers of the first bound entities using said nucleic acid analytes of the first bound entities as templates to form first copies of said analytes;
   d) using said ligating means, ligating said set of oligonucleotides or polynucleotides a)(v) to the 3' end of said first copies formed in step c) to form more than one ligated product;
   e) contacting said ligated products with said second set of primers to form more than one second bound entity, each comprising a second set primer hybridize to one of the ligated products;
   f) using said polymerizing means, extending said bound second set primers of the second bound entities using said ligated products of the second bound entities as templates to form more than one complex comprising said ligated products and said extended second set primers;
   g) using said synthesizing means, synthesizing under isothermal or isostatic conditions from a production center in said first set of primers incorporated in said complexes one or more nucleic acid copies;
   h) hybridizing said nucleic acid copies formed in step g) to said array of nucleic acids provided in step a) (i); and
   i) detecting or quantifying any of said hybridized copies obtained in step h).

2. The process of claim 1, wherein said array of fixed or immobilized nucleic acids comprises members selected from the group consisting of DNA, RNA and analogs thereof.

3. The process of claim 1, wherein said array comprises PNA.

4. The process of claim 2, wherein said array comprises nucleic acids modified on any one of the sugar, phosphate or base moieties.

5. The process of claim 1, wherein the nucleic acids of said array are fixed or immobilized to a solid support.

6. The process of claim 5, wherein said solid support is non-porous.

7. The process of claim 6, wherein said non-porous solid support comprises glass or plastic.

8. The process of claim 5, wherein said solid support is transparent, translucent, opaque or reflective.

9. The process of claim 5, wherein the nucleic acids of said array are directly fixed or immobilized to said solid support.

10. The process of claim 5, wherein the nucleic acids of said array are indirectly fixed or immobilized to said solid support.

11. The process of claim 1, wherein said library of nucleic acid analytes is derived from a biological source selected from the group consisting of organs, tissues and cells.

12. The process of claim 1, wherein said library of nucleic acids analytes is derived from genomic DNA, episomal DNA, unspliced RNA, mRNA, rRNA, snRNA, or a combination of any of the foregoing.

13. The process of claim 1, wherein said first set of primers are complementary to inherent universal detection targets (UDTs) present in the nucleic acid analytes of the library.

14. The process of claim 13, wherein said inherent UDTs are selected from the group consisting of 3' poly A segments, consensus sequences, and a combination of both.

15. The process of claim 14, wherein said inherent UDTs comprise a consensus sequences selected from the group consisting of signal sequences for poly A addition, splicing elements, multicopy repeats, and a combination of any of the foregoing.

16. The process of claim 1, wherein said production center is selected from the group consisting of a primer binding sites, an RNA promoters, and a combination thereof.

17. The process of claim 16, wherein said production center comprises a phage RNA promoter.

18. The process of claim 17, wherein said phage RNA promoter is selected from the group consisting of T3, T7 and SP6.

19. The process of claim 1, wherein said hybridized nucleic acid copies further comprise one or more signaling entities attached thereto or incorporated therein.

20. The process of claim 19, wherein said signaling entities generate a signal directly or indirectly.

21. The process of claim 20, wherein said signal generation is direct signal generation and said signaling entities are selected from the group consisting of a fluorescent compound, a phosphorescent compound, a chemiluminescent compound, a chelating compound, an electron dense compound, a magnetic compound, an intercalating compound, an energy transfer compound and a combination of any of the foregoing.

22. The process of claim 20, wherein said indirect signal generation uses means selected from the group consisting of an antibody, an antigen, a hapten, a receptor, a hormone, a ligand, an enzyme and a combination of any of the foregoing.

23. The process of claim 22, wherein said enzyme catalyzes a reaction selected from the group consisting of a fluorogenic reaction, a chromogenic reaction and a chemiluminescent reaction.

24. The process of claim 1, wherein said polymerizing means comprise a polymerase selected from the group consisting of *E. coli* DNA Pol I, Klenow fragment of *E. coli* DNA Pol I, Bst DNA polymerase, Bca DNA polymerase, Taq DNA polymerase, Tth DNA Polymerase, T4 DNA polymerase, ALV reverse transcriptase, MuLV reverse transcriptase, RSV reverse transcriptase, HIV-1 reverse transcriptase, HIV-2 reverse transcriptase, Sensiscript and Omniscript.

25. The process of claim 1, wherein said ligating means comprise T4 DNA ligase.

26. The process of claim 1, further comprising the step of separating the first copies obtained from step c) from their templates and repeating step b).

27. The process of claim 1, further comprising the step of separating the extended second set of primers obtained from step f) from their templates and repeating step e).

28. The process of claim 1, wherein step g) is carried out repeatedly.

29. The process of claim 1, wherein said synthesizing means for synthesizing nucleic acid copies under isothermal or isostatic conditions from a production center synthesize nucleic acid copies by one or more of RNA transcription, strand displacement amplification and secondary structure amplification.

30. The process of claim 5, wherein said solid support is porous.

31. The process of claim 10, wherein the nucleic acids of said array are indirectly fixed or immobilized to said solid support by means of a chemical linker or linkage arm.

32. The process of claim 30, wherein said porous solid support is selected from the group consisting of polyacrylamide and agarose.

* * * * *

UNITED STATES PATENT AND TRADEMARK OFFICE
CERTIFICATE OF CORRECTION

PATENT NO. : 9,617,584 B2  Page 1 of 1
APPLICATION NO. : 14/812293
DATED : April 11, 2017
INVENTOR(S) : Elazar Rabbani et al.

It is certified that error appears in the above-identified patent and that said Letters Patent is hereby corrected as shown below:

In Claim 15, Column 90, Line 27, "a consensus sequences" should be "a consensus sequence"

In Claim 16, Column 90, Line 34, "sites, an RNA promoters" should be "site, an RNA promoter"

Signed and Sealed this
Tenth Day of April, 2018

Andrei Iancu
*Director of the United States Patent and Trademark Office*